US010858412B2

(12) United States Patent
Mumm

(10) Patent No.: US 10,858,412 B2

(45) Date of Patent: Dec. 8, 2020

(54) ANTIBODY VARIABLE DOMAIN REGIONS FUSED TO IL-10 VARIANT MOLECULES

(71) Applicant: Deka Biosciences, Inc., Bethesda, MD (US)

(72) Inventor: John Mumm, Bethesda, MD (US)

(73) Assignee: DEKA BIOSCIENCES, INC., Bethesda, MD (US)

( * ) Notice: Subject to any disclaimer, the term of this patent is extended or adjusted under 35 U.S.C. 154(b) by 0 days.

(21) Appl. No.: 16/811,718

(22) Filed: Mar. 6, 2020

(65) Prior Publication Data

US 2020/0283488 A1 Sep. 10, 2020

Related U.S. Application Data

(60) Provisional application No. 62/814,669, filed on Mar. 6, 2019, provisional application No. 62/899,504, filed on Sep. 12, 2019, provisional application No. 62/962,332, filed on Jan. 17, 2020.

(51) Int. Cl.

| | |
|---|---|
| ***C07K 14/54*** | (2006.01) |
| ***C07K 16/22*** | (2006.01) |
| ***A61K 39/00*** | (2006.01) |
| ***A61K 38/00*** | (2006.01) |
| ***A61P 29/00*** | (2006.01) |

(52) U.S. Cl.

CPC .......... *C07K 14/5428* (2013.01); *A61P 29/00* (2018.01); *C07K 16/22* (2013.01); *A61K 38/00* (2013.01); *A61K 2039/505* (2013.01); *C07K 2319/30* (2013.01)

(58) Field of Classification Search

None

See application file for complete search history.

(56) References Cited

PUBLICATIONS

Qin et al., Combination of localized radiation therapy andERB-IL-10 generates abscopal effect by activating CD8+ T cells in tumor microenvironment. Int. J. Radiation Oncol.*Biol.*Phys., 99, Supplement, Oct. 1, 2017, p. S162. (Year: 2017).*

* cited by examiner

*Primary Examiner* — Elly-Gerald Stoica

(74) *Attorney, Agent, or Firm* — Arent Fox LLP

(57) ABSTRACT

The application relates to compositions or formulations comprising variant IL-10 molecules, fusion proteins, and chimeric proteins thereof useful for the treatment of cancer, inflammatory diseases or disorders, and autoimmune diseases or disorders.

11 Claims, 28 Drawing Sheets

Specification includes a Sequence Listing.

IL-10 Variant Sequences

Variant 0 (DVLP0): Add leader for production (Seq ID No. 9)

1 MDMRVPAQLL GLLLLWLRGA RCGTDQCDNF PQMLRDLRDA FSRVKTFFQT DEVDNLLLK
61 ESLLEDFKGY LGCQALSEMI QFYLEEVMPQ AENQDPEAKD HVNSLGENLK LRLRLRRCH
121 RFLPCENKSK AVEQIKNAFN KLQEKGIYKA MSEFDIFINY IEAYMTIKAR

Variant 1 (DVLP1): CMV linker (Seq ID No. 10)

1 MDMRVPAQLL GLLLLWLRGA RCGTDQCDNF PQMLRDLRDA FSRVKTFFQT KDEVDNLLLK
61 ESLLEDFKGY LGCQALSEMI QFYLEEVMPQ AENQDPEAKD HVNSLGENLK TLRLRLRQCP
121 LLGCGDKAVE QIKNAFNKLQ EKGIYKAMSE FDIFINYIEA YMTIKAR

Variant 2 (DVLP2): CMV Linker position 43 to L (Seq ID No. 11)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEAKD HVNSLGENLK TLRLRLRQCP
121 LLGCGDKAVE QIKNAFNKLQ EKGIYKAMSE FDIFINYIEA YMTIKAR

Variant 3 (DVLP3): CMV Linker position 87 to I (Seq ID No. 12)

1 MDMRVPAQLL GLLLLWLRGA RCGTDQCDNF PQMLRDLRDA FSRVKTFFQT KDEVDNLLLK
61 ESLLEDFKGY LGCQALSEMI QFYLEEVMPQ AENQDPEIKD HVNSLGENLK TLRLRLRQCP
121 LLGCGDKAVE QIKNAFNKLQ EKGIYKAMSE FDIFINYIEA YMTIKAR

Variant 4 (DVLP4) : CMV Linker position 43 to L and 87 to I (Seq ID No.13)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEIKD HVNSLGENLK TLRLRLRQCP
121 LLGCGDKAVE QIKNAFNKLQ EKGIYKAMSE FDIFINYIEA YMTIKAR

FROM FIG. 6A

Variant 5 (DVLP5): Position 43 to L (Seq ID No. 14)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEAKD HVNSLGENLK TLRLRLRRCH
121 RFLPCENKSK AVEQIKNAFN KLQEKGIYKA MSEFDIFINY IEAYMTIKAR

Variant 6 (DVLP6): Position 87 to I (Seq ID No. 15)

1 MDMRVPAQLL GLLLLWLRGA RCGTDQCDNF PQMLRDLRDA FSRVKTFFQT KDEVDNLLLK
61 ESLLEDFKGY LGCQALSEMI QFYLEEVMPQ AENQDPEIKD HVNSLGENLK TLRLRLRRCH
121 RFLPCENKSK AVEQIKNAFN KLQEKGIYKA MSEFDIFINY IEAYMTIKAR

Variant 7 (DVLP7): Position 43 to L and 87 to I (Seq ID No. 16)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEIKD HVNSLGENLK TLRLRLRRCH
121 RFLPCENKSK AVEQIKNAFN KLQEKGIYKA MSEFDIFINY IEAYMTIKAR

Variant 8 (DVFM8): IL-10 variant monomers EBV Monomer with FLAG tag (Seq ID No. 17)

1 MDMRVPAQLL GLLLLWLRGA RCGTDQCDNF PQMLRDLRDA FSRVKTFFQT KDEVDNLLLK
61 ESLLEDFKGY LGCQALSEMI QFYLEEVMPQ AENQDPEAKD HVNSLGENLK TLRLRLRRCH
121 RFLPCENGGG SGGKSKAVEQ IKNAFNKLQE KGIYKAMSEF DIFINYIEAY MTIKARDYKD DDDK

Variant 9 (DVFM9): EBV Monomer with FLAG tag and position 43 to L (Seq ID No. 18)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEAKD HVNSLGENLK TLRLRLRRCH
121 RFLPCENGGG SGGKSKAVEQ IKNAFNKLQE KGIYKAMSEF DIFINYIEAY MTIKARDYKD DDDK

Variant 10 (DVFM10): EBV Monomer with FLAG tag and position 87 to I (Seq ID No. 19)

1 MDMRVPAQLL GLLLLWLRGA RCGTDQCDNF PQMLRDLRDA FSRVKTFFQT KDEVDNLLLK

FROM FIG. 6B

61 ESLLEDFKGY LGCQALSEMI QFYLEEVMPQ AENQDPEIKD HVNSLGENLK TLRLRLRRCH
121 RFLPCENGGG SGGKSKAVEQ IKNAFNKLQE KGIYKAMSEF DIFINYIEAY MTIKARDYKD DDDK

Variant 11 (DVFM11): EBV Monomer with FLAG tag and position 43 to L 87 to I (Seq ID No. 20)

1 MDMRVPAQLL GLLLLWLRGA RCGTDQCDNF PQMLRDLRDA FSRVKTFFQT KDELDNLLLK
61 ESLLEDFKGY LGCQALSEMI QFYLEEVMPQ AENQDPEIKD HVNSLGENLK TLRLRLRRCH
121 RFLPCENGGG SGGKSKAVEQ IKNAFNKLQE KGIYKAMSEF DIFINYIEAY MTIKARDYKD DDDK

Human IL-10 (DVFM12): IL-10 Monomer with FLAG tag (Seq ID No. 21)

1 MDMRVPAQLL GLLLLWLRGA RCGTQSENSC THFPGNLPNM LRDLRDAFSR VKTFFQMKDQ
61 LDNLLLKESL LEDFKGYLGC QALSEMIQFY LEEVMPQAEN QDPDIKAHVN SLGENLKTLR
121 LRLRRCHRFL PCENGGGSGG KSKAVEQVKN AFNKLQEKGI YKAMSEFDIF INYIEAYMTM
181 KIRNDYKDDD DK

Human IL-10 (DVF13): IL-10 dimer with FLAG tag / IL-10 variant FLAG TAGGED controls (Seq ID No. 22)

1 MDMRVPAQLL GLLLLWLRGA RCGTQSENSC THFPGNLPNM LRDLRDAFSR VKTFFQMKDQ
61 LDNLLLKESL LEDFKGYLGC QALSEMIQFY LEEVMPQAEN QDPDIKAHVN SLGENLKTLR
121 LRLRRCHRFL PCENKSKAVE QVKNAFNKLQ EKGIYKAMSE FDIFINYIEA YMTMKIRNDY KDDDDK

Variant 14 (DVF14):EBV Dimer with FLAG tag (Seq ID No. 23)

1 MDMRVPAQLL GLLLLWLRGA RCGTDQCDNF PQMLRDLRDA FSRVKTFFQT KDEVDNLLLK
61 ESLLEDFKGY LGCQALSEMI QFYLEEVMPQ AENQDPEAKD HVNSLGENLK TLRLRLRRCH
121 RFLPCENKSK AVEQIKNAFN KLQEKGIYKA MSEFDIFINY IEAYMTIKAR DYKDDDDK

Fusion Protein: Anti-HIV VH-Anti-Ebola VL-EBV IL-10 Position 43 to L (Chain 1) (Seq ID No. 24)

1 QVQLVQSGAE VKKPGASVKI SCKASGYNFT TYAMHWVRQA PGQGLEWMGW INGGNGDTRY
61 SQKFRGRVTI SRDTSASTAY MELHSLTSED TALFYCARES GDYYSEISGA LDWGQGTLVT

FROM FIG. 6C

121 VSSGGGGSEI VMTQSPGTLS LSPGERATLS CRASQSVPRN YIGWFQQKPG QAPRLLIYGA
181 SSRAAGFPDR FSGSGSGTDF TLTITRLEPE DFAMYYCHQY DRLPYTFGQG TKLEIKGGGG
241 SGGGGSGGGG STDQCDNFPQ MLRDLRDAFS RVKTFFQTKD ELDNLLLKES LLEDFKGYLG
301 CQALSEMIQF YLEEVMPQAE NQDPEAKDHV NSLGENLKTL RLRLRRCHRF LPCENKSKAV
361 EQIKNAFNKL QEKGIYKAMS EFDIFINYIE AYMTIKAR

Fusion Protein: EBV IL-10 Position 43 to L-Anti-Ebola VH-Ant-HIV VL (Chain 2) (Seq ID No. 25)

1 TDQCDNFPQM LRDLRDAFSR VKTFFQTKDE LDNLLLKESL LEDFKGYLGC QALSEMIQFY
61 LEEVMPQAEN QDPEAKDHVN SLGENLKTLR LRLRRCHRFL PCENKSKAVE QIKNAFNKLQ
121 EKGIYKAMSE FDIFINYIEA YMTIKARGGG GSGGGGSGGG GSQVQLQQWG AGLLKPSETL
181 SLTCAVYGGS FTTTYWNWIR QPPGKGLEWI GEVNYSGNAN YNPSLKGRVA ISVDTSKNQF
241 SLRLNSVTAA DTAIYYCTSR IRSHIAYSWK GDVWGKGTTV TVSSGGGGSS YELTQPPSVS
301 VSPGQTARIT CSGDVLPKKY AYWYQQKSGL APVLVIYEDN RRPSGIPERF SGSSSGTMAT
361 LTISGAQVED EGDYYCSSTD SSGDHYVFGT GTKVTVL

Fusion Protein: Anti-HIV VH-Anti-Ebola VL-EBV IL-10 Position 87 to I (Chain 1) (Seq ID No. 26)

1 QVQLVQSGAE VKKPGASVKI SCKASGYNFT TYAMHWVRQA PGQGLEWMGW INGGNGDTRY
61 SQKFRGRVTI SRDTSASTAY MELHSLTSED TALFYCARES GDYYSEISGA LDWGQGTLVT
121 VSSGGGGSEI VMTQSPGTLS LSPGERATLS CRASQSVPRN YIGWFQQKPG QAPRLLIYGA
181 SSRAAGFPDR FSGSGSGTDF TLTITRLEPE DFAMYYCHQY DRLPYTFGQG TKLEIKGGGG
241 SGGGGSGGGG STDQCDNFPQ MLRDLRDAFS RVKTFFQTKD EVDNLLLKES LLEDFKGYLG
301 CQALSEMIQF YLEEVMPQAE NQDPEIKDHV NSLGENLKTL RLRLRRCHRF LPCENKSKAV
361 EQIKNAFNKL QEKGIYKAMS EFDIFINYIE AYMTIKAR

Fusion Protein: EBV IL-10 Position 87 to I-Anti-Ebola VH-Ant-HIV VL (Chain 2) (Seq ID No. 27)

1 TDQCDNFPQM LRDLRDAFSR VKTFFQTKDE VDNLLLKESL LEDFKGYLGC QALSEMIQFY
61 LEEVMPQAEN QDPEIKDHVN SLGENLKTLR LRLRRCHRFL PCENKSKAVE QIKNAFNKLQ

FROM FIG. 6D

121 EKGIYKAMSE FDIFINYIEA YMTIKARGGG GSGGGGSGGG GSQVQLQQWG AGLLKPSETL
181 SLTCAVYGGS FTTTYWNWIR QPPGKGLEWI GEVNYSGNAN YNPSLKGRVA ISVDTSKNQF
241 SLRLNSVTAA DTAIYYCTSR IRSHIAYSWK GDVWGKGTTV TVSSGGGGSS YELTQPPSVS
301 VSPGQTARIT CSGDVLPKKY AYWYQQKSGL APVLVIYEDN RRPSGIPERF SGSSSGTMAT
361 LTISGAQVED EGDYYCSSTD SSGDHYVFGT GTKVTVL

Fusion Protein: Anti-HIV VH-Anti-Ebola VL-EBV IL-10 Position 43 to L and 87 to I (Chain 1) (Seq ID No. 28)

1 QVQLVQSGAE VKKPGASVKI SCKASGYNFT TYAMHWVRQA PGQGLEWMGW INGGNGDTRY
61 SQKFRGRVTI SRDTSASTAY MELHSLTSED TALFYCARES GDYYSEISGA LDWGQGTLVT
121 VSSGGGGSEI VMTQSPGTLS LSPGERATLS CRASQSVPRN YIGWFQQKPG QAPRLLIYGA
181 SSRAAGFPDR FSGSGSGTDF TLTITRLEPE DFAMYYCHQY DRLPYTFGQG TKLEIKGGGG
241 SGGGGSGGGG STDQCDNFPQ MLRDLRDAFS RVKTFFQTKD ELDNLLLKES LLEDFKGYLG
301 CQALSEMIQF YLEEVMPQAE NQDPEIKDHV NSLGENLKTL RLRLRRCHRF LPCENKSKAV
361 EQIKNAFNKL QEKGIYKAMS EFDIFINYIE AYMTIKAR

Fusion Protein: EBV IL-10 Position 43 to L and 87-Anti-Ebola VH-Anti-HIV VL (Chain 2) (Seq ID No. 29)

1 TDQCDNFPQM LRDLRDAFSR VKTFFQTKDE LDNLLLKESL LEDFKGYLGC QALSEMIQFY
61 LEEVMPQAEN QDPEIKDHVN SLGENLKTLR LRLRRCHRFL PCENKSKAVE QIKNAFNKLQ
121 EKGIYKAMSE FDIFINYIEA YMTIKARGGG GSGGGGSGGG GSQVQLQQWG AGLLKPSETL
181 SLTCAVYGGS FTTTYWNWIR QPPGKGLEWI GEVNYSGNAN YNPSLKGRVA ISVDTSKNQF
241 SLRLNSVTAA DTAIYYCTSR IRSHIAYSWK GDVWGKGTTV TVSSGGGGSS YELTQPPSVS
301 VSPGQTARIT CSGDVLPKKY AYWYQQKSGL APVLVIYEDN RRPSGIPERF SGSSSGTMAT
361 LTISGAQVED EGDYYCSSTD SSGDHYVFGT GTKVTVL

Figure 6E

EBV-IL10 (SEQ ID No. 3)

```
Thr Asp Gln Cys Asp Asn Phe Pro Gln Met Leu Arg Asp Leu Arg Asp Ala Phe Ser Arg
1               5                   10                  15                  20
Val Lys Thr Phe Phe Gln Thr Lys Asp Glu Val Asp Asn Leu Leu Leu Lys Glu Ser Leu
                25                  30                  35                  40
Leu Glu Asp Phe Lys Gly Tyr Leu Gly Cys Gln Ala Leu Ser Glu Met Ile Gln Phe Tyr
                45                  50                  51                  60
Leu Glu Glu Val Met Pro Gln Ala Glu Asn Gln Asp Pro Glu Ala Lys Asp His Val Asn
                65                  70                  75                  80
Ser Leu Gly Glu Asn Leu Lys Thr Leu Arg Leu Arg Leu Arg Arg Cys His Arg Phe Leu
                85                  90                  95                  100
Pro Cys Glu Asn Lys Ser Lys Ala Val Glu Gln Ile Lys Asn Ala Phe Asn Lys Leu Gln
                105                 110                 115                 120
Glu Lys Gly Ile Tyr Lys Ala Met Ser Glu Phe Asp Ile Phe Ile Asn Tyr Ile Glu Ala
                125                 130                 135                 140
Tyr Met Thr Ile Lys Ala Arg
                145
```

Thr Asp Gln Cys Asp Asn Phe Pro Gln Met Leu Arg Asp Leu Arg Asp Ala Phe Ser Arg
1 5 10 15 20
Val Lys Thr Phe Phe Gln Thr Lys Asp Glu Leu Asp Asn Leu Leu Leu Lys Glu Ser Leu
25 30 35 40
Leu Glu Asp Phe Lys Gly Tyr Leu Gly Cys Gln Ala Leu Ser Glu Met Ile Gln Phe Tyr
45 50 51 60
Leu Glu Glu Val Met Pro Gln Ala Glu Asn Gln Asp Pro Glu Ala Lys Asp His Val Asn
65 70 75 80
Ser Leu Gly Glu Asn Leu Lys Thr Leu Arg Leu Arg Leu Arg Arg Cys His Arg Phe Leu
85 90 95 100
Pro Cys Glu Asn Lys Ser Lys Ala Val Glu Gln Ile Lys Asn Ala Phe Asn Lys Leu Gln
105 110 115 120
Glu Lys Gly Ile Tyr Lys Ala Met Ser Glu Phe Asp Ile Phe Ile Asn Tyr Ile Glu Ala
125 130 135 140
Tyr Met Thr Ile Lys Ala Arg
145

```
Thr Asp Gln Cys Asp Asn Phe Pro Gln Met Leu Arg Asp Leu Arg Asp Ala Phe Ser Arg
1               5                   10                  15                  20
Val Lys Thr Phe Phe Gln Thr Lys Asp Glu Val Asp Asn Leu Leu Leu Lys Glu Ser Leu
                25                  30                  35                  40
Leu Glu Asp Phe Lys Gly Tyr Leu Gly Cys Gln Ala Leu Ser Glu Met Ile Gln Phe Tyr
                45                  50                  51                  60
Leu Glu Glu Val Met Pro Gln Ala Glu Asn Gln Asp Pro Glu Ile Lys Asp His Val Asn
                65                  70                  75                  80
Ser Leu Gly Glu Asn Leu Lys Thr Leu Arg Leu Arg Leu Arg Arg Cys His Arg Phe Leu
                85                  90                  95                  100
Pro Cys Glu Asn Lys Ser Lys Ala Val Glu Gln Ile Lys Asn Ala Phe Asn Lys Leu Gln
                105                 110                 115                 120
Glu Lys Gly Ile Tyr Lys Ala Met Ser Glu Phe Asp Ile Phe Ile Asn Tyr Ile Glu Ala
                125                 130                 135                 140
Tyr Met Thr Ile Lys Ala Arg
                145
```

```
Thr Asp Gln Cys Asp Asn Phe Pro Gln Met Leu Arg Asp Leu Arg Asp Ala Phe Ser Arg
1               5                   10                  15                  20
Val Lys Thr Phe Phe Gln Thr Lys Asp Glu Leu Asp Asn Leu Leu Leu Lys Glu Ser Leu
                25                  30                  35                  40
Leu Glu Asp Phe Lys Gly Tyr Leu Gly Cys Gln Ala Leu Ser Glu Met Ile Gln Phe Tyr
                45                  50                  51                  60
Leu Glu Glu Val Met Pro Gln Ala Glu Asn Gln Asp Pro Glu Ile Lys Asp His Val Asn
                65                  70                  75                  80
Ser Leu Gly Glu Asn Leu Lys Thr Leu Arg Leu Arg Leu Arg Arg Cys His Arg Phe Leu
                85                  90                  95                  100
Pro Cys Glu Asn Lys Ser Lys Ala Val Glu Gln Ile Lys Asn Ala Phe Asn Lys Leu Gln
                105                 110                 115                 120
Glu Lys Gly Ile Tyr Lys Ala Met Ser Glu Phe Asp Ile Phe Ile Asn Tyr Ile Glu Ala
                125                 130                 135                 140
Tyr Met Thr Ile Lys Ala Arg
                145
```

Figure 21D

ANTIBODY VARIABLE DOMAIN REGIONS FUSED TO IL-10 VARIANT MOLECULES

CROSS REFERENCE TO RELATED APPLICATIONS

This application claims priority to U.S. Provisional Patent Application No. 62/814,669, filed Mar. 6, 2019, U.S. Provisional Patent Application No. 62/899,504, filed Sep. 12, 2019, and U.S. Provisional Patent Application No. 62/962,332, filed Jan. 17, 2020, the disclosures of each are herein incorporated by reference in their entireties.

INTRODUCTION

The application relates to variant forms of Interleukin 10 (IL-10) that include modifications to the IL-10 receptor binding region and/or the domains responsible for the inter-domain angles that exists in the IL-10 molecule. By modifying one or both of these domains in IL-10, the inventors have surprisingly found that the resulting biological function of the IL-10 receptor may be tuned or modulated to elicit a specific biological response. The application also relates to a half-life extended IL-10 or IL-10 variant molecule that include non-protein based serum extension moieties as well as protein based extension modalities. The Application also relates to fusion proteins comprising the IL-10 variant molecules.

BACKGROUND

IL-10 has been described as cytokine synthesis inhibitory factor, due to its capacity to inhibit both (i) pro-inflammatory cytokine secretion by monocytes/macrophages in response to lipopolysaccharide, and (ii) interleukin 2 (IL-2) secretion and proliferation of $CD4^+$ T cells. When viral analogues of IL-10 were discovered and reported to share similar or identical functions to human IL-10, it was presumed that these viral analogs of IL-10 enhanced viral virulence by adopting the function of a suppressive cytokine found in the human genome.

Further investigation of the suppressive effects of IL-10 was made possible by the generation of the IL-10 knockout mice that develop chronic enterocolitis. The data generated from these mice clearly illustrated that IL-10 knockout mice develop severe inflammation throughout the gastrointestinal track, predominantly through chronic inflammatory cytokine secretion by monocytes/macrophages and $CD4^+$ T cells, which is consistent with initial in vitro observations.

Collectively the data implied that IL-10 exerted a dominant role in suppressing inflammation. In particular, patients lacking functional IL-10 receptors, or the ability to produce IL-10 exhibited an increased predisposition to developing inflammation associated diseases of the gastrointestinal track.

Multiple clinical trials were conducted to evaluate the anti-inflammatory function of IL-10 in context of psoriasis, rheumatoid arthritis, and Crohn's disease. In general, recombinant human IL-10 (rHuIL-10) treatment was found to be safe but lacking in efficacy. In particular, treating Crohn's patients with rHuIL-10 lead to an inverse dose response, where low doses appeared to moderately inhibit inflammation and the suppressive effect was lost at high doses. Rigorous analysis of the final Crohn's study revealed that patients dosed with 10 and 20 μg/kg rHuIL-10 exhibited increased serum concentrations of interferon gamma (IFNγ) and Neopterin. IFNγ is known to worsen the pathogenesis of inflammatory bowel disease, and Crohn's disease. The data suggests that at high doses, treatment with IL-10 induces IFNγ, which, in turn, will exacerbate inflammatory disease.

Further analysis of IL-10 effects in healthy humans suggests that administration of IL-10 before exposure to the pro-inflammatory factor lipopolysaccharide (LPS) inhibits production of pro-inflammatory cytokines. However, administering rHuIL-10 after exposure to LPS enhanced the secretion of pro-inflammatory cytokines. Since LPS is a product of both normal and foreign gut bacteria in patients with Inflammatory Bowel Disease (IBD), these patients will never be "free" of LPS and therefore will never be in a state where IL-10 treatment could be applied prior to LPS. Thus, these data suggests that Crohn's and patients with other inflammatory diseases will never see the therapeutic benefits of IL-10 treatment.

Adding further confusion to the role of IL-10 is the accumulating data indicating that IL-10 activates the immune system to induce anti-tumor responses. Initial data suggested that IL-10 activated NK cells, but further investigation uncovered that IL-10 treatment inhibits tumor growth in a $CD8^+$ T cell and IFNγ dependent manner. Continued investigation revealed that IL-10 treatment inhibits $FoxP3^+CD4^+$ T regulatory cell proliferation, and enhanced Kupffer cell scavenging, which are all functions suggesting that IL-10 is a potent immune stimulant, rather than a suppressor. Lastly, these stimulatory activities where confirmed in clinical studies of oncology patients treated with PEGylated IL-10.

Collectively, these data indicates that IL-10 treatment of patients suffering from autoimmune associated inflammation failed to elicit a therapeutic benefit, suggesting that IL-10 is not a pan-immune suppressant. In keeping with this, treating cancer patients with (PEG) IL-10 lead to potent and therapeutically useful immune activation, specifically the induction of dose dependent serum IFNγ, similar to Crohn's patients treated with IL-10, implying that IL-10 is a potent immune stimulant.

Unresolved then is why viruses would acquire the IL-40 sequence. Further analysis of both the Epstein Barr Virus (EBV-IL10) and Cytomegalovirus (CMV-IL10) homologs suggest these viruses have altered the native IL-10 sequence in two predominant ways. The EBV-IL10 appears to retain a similar tertiary angle of homodimer interaction leading to a specific angle of ligand receptor interaction, while substantially decreasing it's affinity for the IL-10 receptor. The CMV-IL10 exhibits an increased affinity for the IL-10 receptor while substantially altering the angle of interaction with the IL-10 receptors. While the EBV-IL10 and CMV-IL10 sequences respectively retain approximately 80% and 27% homology to native IL-10, each of the viral homologs have completely different IL-10 receptor affinities, different angles of receptor engagement, with each viral homologues appearing to exert highly similar anti-inflammatory functions to native IL-10. It is therefore unclear how the affinity for the IL-10 receptors and/or the angle of receptor interaction affects the subsequent downstream transduction of the IL-10 signal.

SUMMARY OF VARIOUS PREFERRED EMBODIMENTS

The present application generally relates to novel IL-10 variant molecules that modulate IL-10 receptor signal transduction. Thus, the application relates to IL-10 variant molecules that incorporate modifications to the structure of an IL-10 molecule, resulting in novel IL-10 variant molecules having altered IL-10 receptor binding affinities and/or altered IL-10 inter-domain angles. The inventor surprisingly discovered that modifying IL-10 in key domains impacting IL-10 receptor affinity and/or IL-10 inter-domain angles resulted in the creation of IL-10 receptor agonists that may be used in treating immune diseases, inflammatory diseases or conditions, as well as in treating cancer. Moreover, the IL-10 variant molecules may also have increased serum half-life by incorporating the variant IL-10 molecules as part of a fusion protein, such as various antibody domains (Fc or variable domains), without impeding the monomers of IL-10 or the IL-10 variants from forming an IL-10 homodimer.

In certain embodiments, the IL-10 variant molecule is modified human IL-10. In other embodiments, the IL-10 variant molecule is modified mouse IL-10. In preferred embodiments, the IL-10 variant molecule is a modified viral homolog of IL-10. In a more preferred embodiment, the viral IL-1 homolog is CMV-IL10. In a most preferred embodiment, the viral IL-10 homolog is EBV-IL10.

In further embodiments, the IL-10 variant molecule incorporates at least one or more amino acid additions, deletions or substitutions within the receptor binding region. In yet other embodiments, the IL-10 variant molecule incorporates at least one or more amino acid additions, deletions or substitutions in a region responsible for forming the inter-domain angle of IL-10. In a preferred embodiment, the IL-10 variant molecule incorporates one or both of the modifications to the receptor binding domain and/or the region responsible for the inter-domain angle. In a most preferred embodiment, the IL-10 variant molecule incorporates one or both modifications in an EBV-IL10 protein molecule.

In various embodiments, the IL-10 variant molecule, when compared to wild-type IL-10, has enhanced affinity to the IL-10 receptor or receptor complex. In other embodiments, the IL-10 variant molecule, when compared to the wild-type IL-10, has diminished affinity to the IL-10 receptor or receptor complex. In other embodiments, the IL-10 variant molecule forms a narrower or constrained inter-domain angle, when compared to the wild-type IL-10, more preferably EBV-IL10. In another embodiment, the IL-10 variant molecule forms a wider or relaxed inter-domain angle, when compared to the wild-type IL-10, more preferably EBV 1-10.

In yet further embodiments, the EBV IL-10 variant molecules incorporate at least one or more amino acid additions, deletions or substitutions within the receptor binding region located in the helix A, the AB loop, and/or the helix F ("site 1") of EBV IL-10. The modifications to the receptor binding domain region may, in certain embodiments, increase or enhance the affinity to the IL-10 receptor or receptor complex. In certain other embodiments, modifications to the receptor binding region may diminish or decrease the affinity to the IL-10 receptor or receptor complex.

In further embodiments, the EBV IL-10 variant molecules incorporate at least one or more amino acid additions, deletions or substitutions within the EBV IL-10 regions responsible for inter-domain angle formation. In preferred embodiments, the modifications may occur in the DE loop of EBV IL-10. The modifications in the DE loop result in EBV IL-10 variant molecules that have a constrained inter-domain angle or a relaxed inter-domain angle.

In other aspects, the IL-10 variant molecules are chimeric or fusion molecules. In one embodiment, the chimeric or fusion protein will comprise one or more domains from different proteins or mutations within a single protein giving the characteristics of another protein. In a preferred embodiment, the chimeric or fused protein will include a first portion comprising an IL-10 variant molecule as described herein fused to another molecule including, but not limited to albumin, enzymes, glycosyltransferases, galactosyltransferases, IgG hinge regions (such as an Fc region), one or more variable domains (such as but not limited to a variable heavy chain or a variable light chain) of one or more antibodies, cytokines (such as IL-6, IL-4, IL-1, IL-2, IL-3, IL-5, IL-7, IL-8, IL-9, IL-12, IL-15, GM-CSF, G-CSF, interferons-α, -β, -γ, TGF-β, and tumor necrosis factors-α, -β), labels, agents, chemotherapeutic agents, radioisotopes, and half-life extenders (such as hydroxyl ethyl starch (HESylation), polysialic acids, heparosan polymers, elastin-like polypeptides and hyaluronic acid). In still another embodiment, the IL-10 variant molecule is fused to one or more antibody heavy or light chain variable regions. The fusion proteins may include one or more linkers that covalently linked the different parts of the fusion protein. The fusion protein may form a non-covalently bound complex with another fusion protein of the same type. Such a fusion protein will allow monomers of IL-10 or monomers of the variant IL-10 molecule to associate together into a functional homodimer of IL-10 or variant IL-10.

In other embodiments, the variant IL-10 molecule is part of an engineered fusion protein. The fusion protein will comprise at least one monomer of an IL-10 or an IL-10 variant molecule conjugated at a first terminal end of the fusion protein to a linker or spacer, wherein the one or more spacers are used to link the various parts of the fusion protein, which is then conjugated to at least one other molecule conjugated at the other terminal end, wherein the molecule is selected from at least one cytokine or monomer thereof, a therapeutic agent, a label, a serum half-life extension molecule, or a protein (such as but not limited to a receptor, ligand, or various portions of an antibody). In a preferred embodiment, the fusion protein comprises a monomer of IL-10 or a monomer of an IL-10 variant molecule conjugated, via linkers or spacers, to at least one heavy and/or light chain variable region. In a most preferred embodiment, the fusion protein comprises a monomer of EBV IL-10 or a monomer of an EBV IL-10 variant molecule conjugated, via linkers or spacers, to at least one heavy and/or light chain region. In a most preferred embodiment, a monomer of EBV IL-10 or EBV IL-10 variant molecule thereof is conjugated to one heavy chain variable region and one light chain variable region, where the monomers together form a dimer complex. The monomer of EBV IL-10 or monomer of EBV IL-10 variant molecule maybe conjugated to either the amino terminal or carboxy terminal end of a heavy or light chain variable region.

In certain embodiments, a therapeutic amount of the IL-10 variant molecule, fusion protein or chimeric protein thereof of the application is administered to a subject suffering from an inflammatory disease or condition, such as but not limited to inflammatory bowel disease (IBD), Crohn's disease, Ulcerative colitis, nonalcoholic steatohepatitis (NASH), and nonalcoholic fatty liver disease (NAFLD). In another embodiment, a therapeutic amount of the IL-10 variant molecule, fusion protein or chimeric protein thereof of the application is administered to a subject suffering from cancer. Treatment of subjects having more than one pathological condition is also envisioned. In a more preferred embodiment, the IL-10 variant molecule is an EBV-IL10 variant, fusion protein or chimeric protein thereof. In yet another embodiment, the IL-10 variant molecule, fusion protein or chimeric protein thereof is used in combination therapy. For example, the IL-10 variant molecule, fusion protein or chimeric protein thereof may be administered to a subject in conjunction with other therapies or treatments. In yet other embodiments, a therapeutic amount of the IL-10 variant molecule, fusion protein or chimeric protein thereof of the application is administered to a subject suffering from lipid based diseases, such as but not limited to elevated levels cholesterol.

In various embodiments, the IL-10 variant molecule or fusion protein thereof of the present application is delivered as an isolated and purified protein. The delivery may be in the form of a subcutaneous bolus injection or in the form of multiple microinjections into the dermis and subcutaneous tissue. In yet another embodiment, the IL-10 variant molecule may be delivered as a nucleic acid vector comprising a sequence encoding the IL-10 variant, fusion protein or chimeric protein thereof. The nucleic acid vector can be a plasmid or a viral particle carrying a viral vector. In one embodiment, the IL-10 variant molecules may be delivered to a subject by genetic medicine techniques generally known to those of skill in the art.

In other embodiments, the IL-10 variant molecule may also be administered as part of a combination therapy regimen. In one embodiment, the IL-10 variant molecule can be administered in combination with Bispecific T-Cell Engagers (BITES), immunotherapies currently available for the treatment of cancer, IBD, Crohn's disease, NAFLD, NASH, and autoimmune diseases, for example.

In another embodiment, the nucleic acid vector is an adeno-associated virus (AAV) vector having one or more. AAV inverted terminal repeat (ITR) sequence elements and control elements for directing expression of the sequence encoding the IL-10 variant molecule in a target cell, which AAV vector can be administered either as a plasmid ("naked" DNA) or as packaged in an AAV particle. In another embodiment, the nucleic acid vector is a vaccinia virus vector. A variety of vaccinia viral vectors derived from different strains may be used to introduce the variant IL-10 molecules of the present application, such as WR strain (ATCC VR-119), the Wyeth strain (ATCC VR-325), the Lederle-Chorioallantoic strain (ATCC VR-325), the CL strain (ATCC VR-117), and others; all of these strains are available from the American Type Culture Collection (Manassas, Va.).

In another embodiment, any of the IL-10 variant molecules described herein, include but not limited to PEGylated IL-10 variant molecules, may be delivered to a subject by any method described herein or generally known in the art.

These and other embodiments of the subject application will readily occur to those of skill in the art in view of the disclosure herein.

BRIEF DESCRIPTION OF THE DRAWINGS

FIGS. 6A-6E show specific amino acid sequences for various IL-10 variant molecules and fusion proteins comprising EBV-IL-10.

FIG. 8A (DV05) is an IL-10 variant comprising a single point mutation at amino acid position 31 (V31L V31L) of SEQ ID No. 3. FIG. 8B (DV06) is an IL-10 variant comprising a single point mutation at amino acid position 75 (A75I A75I) of SEQ ID No. 3. FIG. 8C (DV07) is an IL-10 variant comprising a two point mutations at amino acid positions 31 and 75 (V31L and A75I) of SEQ ID No. 3.

FIGS. 9(*a*)-(*c*) represent a fusion protein complex (i.e., a diabody) where each fusion protein comprises a VH and VL regions obtained from two different antibodies linked to a monomer of IL-10 (which may also be substituted with an IL-10 variant molecule) via a carboxy terminal linker or an amino terminal linker with (a) a single mutation—e.g., amino acid position 31—impacting IL-10 receptor binding; (b) a single mutation—e.g. amino acid position 75—impacting IL-10 receptor binding; and (c) two mutations—e.g. amino acid positions 31 and 75—impacting IL-10 receptor binding. FIGS. 9(*d*)-(*f*) represent a fusion protein complex (i.e., a minibody) where each fusion protein comprises a single VH or VL region obtained from one antibody linked to a monomer of IL-10 (which may also be substituted with an IL-10 variant molecule) via a carboxy terminal linker or an amino terminal linker with (d) a single mutation—e.g., amino acid position 31—impacting IL-10 receptor binding; (e) a single mutation—e.g., amino acid position 75—impacting IL-10 receptor binding; and (f) two mutations—e.g., amino acid positions 31 and 75—impacting IL-10 receptor binding.

FIGS. 10(*a*)-(*c*) represents a single fusion protein (i.e., minibody) where the monomers of IL-10 (which may also be substituted with an IL-10 variant molecule) are each linked via a carboxy terminal linker or an amino terminal linker to either a VH or VL from the same antibody and the VH and VL are linked together.

The monomers of IL-10 comprise (a) a single mutation—e.g., amino acid position 31—impacting IL-10 receptor binding; (b) a single mutation—e.g., amino acid position 75—impacting IL-10 receptor binding; and (c) two mutations—e.g., amino acid positions 31 and 75—impacting IL-10 receptor binding. FIGS. 10(*d*)-(*f*) represents a single fusion protein where monomers of IL-10 (which may also be substituted with an IL-10 variant molecule) are linked together and each monomer of IL-10 is further linked via a carboxy terminal linker or an amino terminal linker to a single VH or VL region obtained from one antibody. The IL-10 monomers comprise (d) a single mutation—e.g., amino acid position 31) impacting IL-10 receptor binding; (e) a single mutation—e.g., amino acid position 75—impacting IL-10 receptor binding; and (f) two mutations—e.g., amino acid positions 31 and 75) impacting IL-10 receptor binding.

FIG. 14A compares the suppression of TNF (induced by LPS in isolated monocytes/macrophages using human IL-1 ("wt"), DH:DV07 and DHDE:DV07. FIG. 14B compares the secretion of IFNγ in isolated T-cell in response to human IL-10 ("wt"), EBV IL-10, DH:DV07 and DHDE:DV07.

FIG. 17A is a dosing study of the non-targeting small format with a dosing of 5 days on, 2 days off, as compared pegylated IL-10 (0.75 mg/kg daily). FIG. 17B is a dosing study of the non-targeting small (1 mg/kg, 0.5 mg/kg, 0.25 mg/kg) and large (0.2 mg/kg) formats with dosing three times a week compared to pegylated recombinant human IL-10 (0.75 mg/kg daily).

FIG. 18A are the results from a daily dosing study of targeted IL-10 fusion proteins, large format (0.25 mg/kg), small format (0.25 mg/kg), and non-targeted IL-10 fusion protein small format (0.25 mg/kg) as compared to pegylated recombinant human IL-10 (0.75 mg/kg). FIG. 18B are the results from a three times a week dosing study of large format targeted IL-10 fusion protein (1 mg/kg, 0.25 mg/kg, and 0.25 mg/kg daily) as compared to large format non-targeted IL-10 fusion protein (DhDe:DV07 at 0.2 mg/kg) and pegylated IL-10 (0.75 mg/kg daily). FIG. 18C are the results from a three times a week dosing study of small format targeted IL-10 fusion protein (1 mg/kg, 0.25 mg/kg) as compared to small format non-targeted IL-10 fusion protein (Debo:DV07 at 1 mg/kg) and pegylated IL-10 (0.75 mg/kg daily)

Figure 19B:
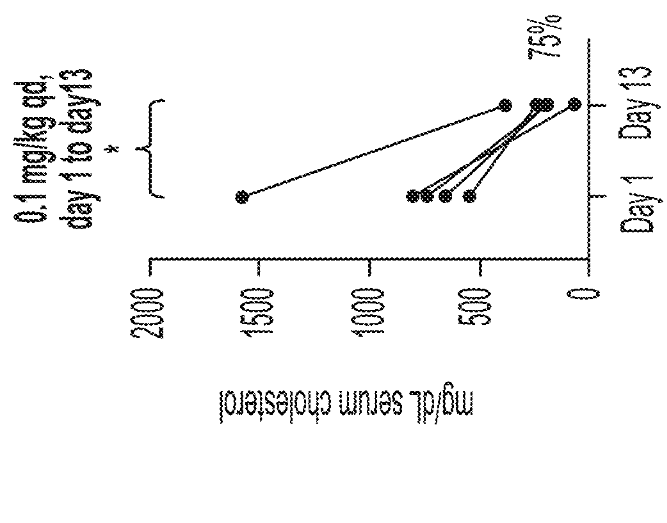
Figure 19A:
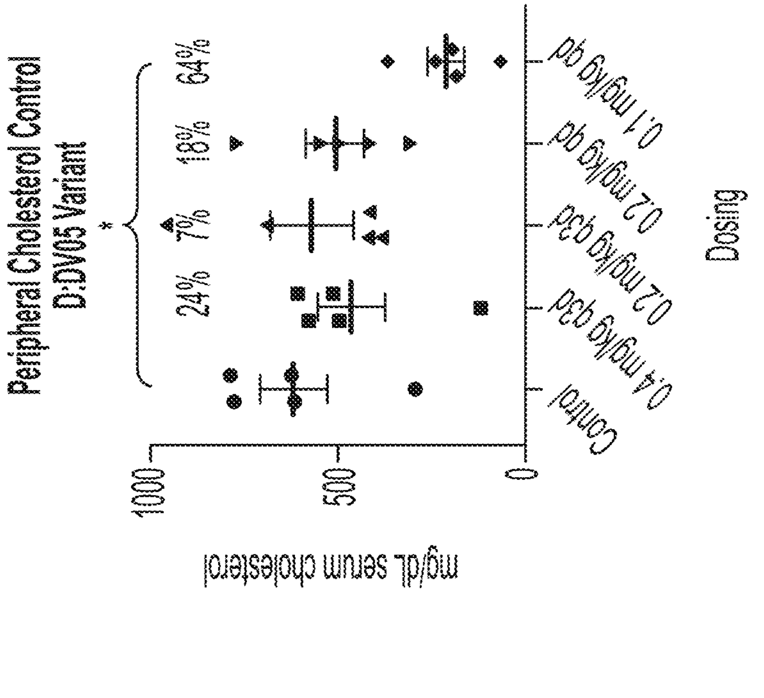

FIGS. 19A-19B are results from an in vivo cholesterol study using a diabody with an EBV IL-10 variant with a V31L mutation comprising variable regions from anti-CD3c and anti-EGFR.

Figure 20A:
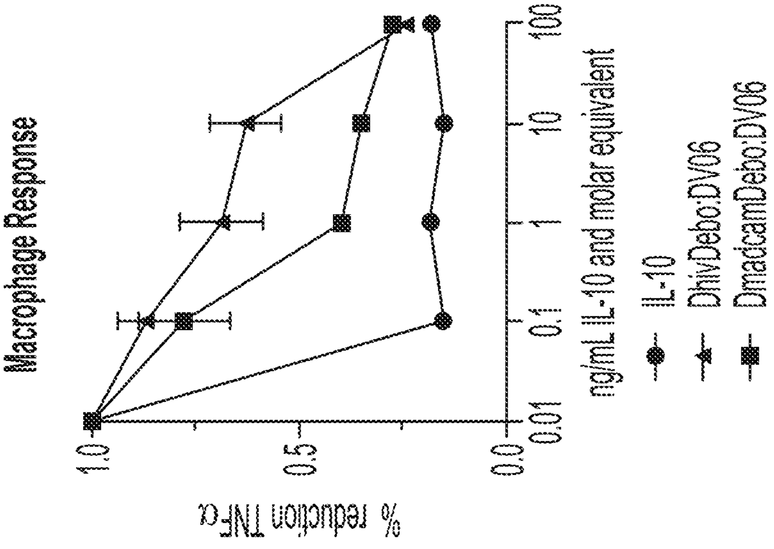
Figure 20B:
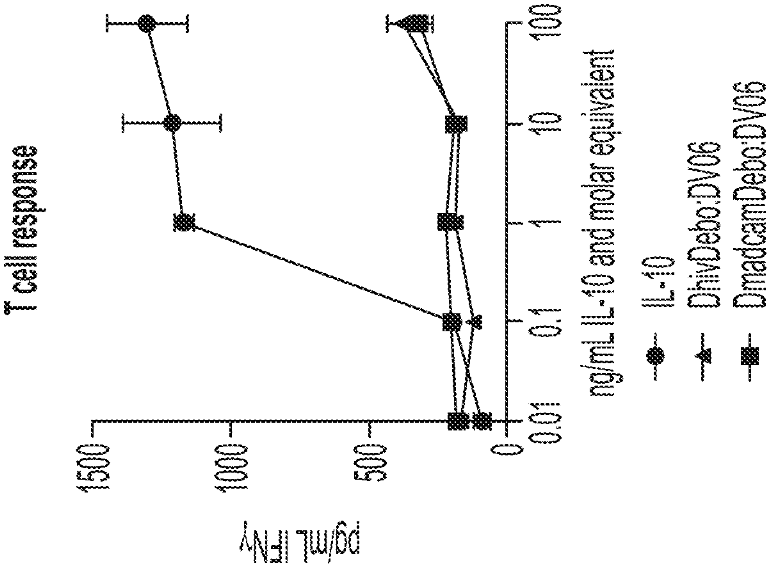

FIGS. 20A-20B are results from an in vitro comparative study on two IL-10 variant fusion proteins on macrophage and T-cells. The assays examine the in vitro effectiveness of two forms of a DV06 fusion protein in comparison to human IL-10. FIG. 20A is a monocyte/macrophage assay using DhivDebo:DV06 (SEQ ID Nos: 26 and 27) and DmadcamDEbo:DV06 (SEQ ID Nos: 41 and 42). FIG. 20B is a T-cell response assay as measured by IFN-gamma using DhivDebo:DV06 (SEQ ID Nos: 26 and 27) and DmadcamDEbo:DV06 (SEQ ID Nos: 41 and 42).

FIGS. 21A-21D are EBV IL-10 amino acid sequences. FIG. 21A is EBV IL-10. FIG. 21B is DV05 including a V31L substitution. FIG. 21C is a DV06 including a A75I substitution. FIG. 21D is DV07 including both V31L and A75I substitutions.

DETAILED DESCRIPTION OF VARIOUS PREFERRED EMBODIMENTS

Before describing the various embodiments application in detail, it is to be understood that this application is not limited to particular formulations or process parameters as such may, of course, vary. It is also to be understood that the terminology used herein is for the purpose of describing various embodiments only, and is not intended to be limiting.

Although a number of methods and materials similar or equivalent to those described herein can be used in the practice of the various described embodiments, the preferred materials and methods are described herein.

Unless otherwise indicated, the embodiments described herein employ conventional methods and techniques of molecular biology, biochemistry, pharmacology, chemistry, and immunology, well known to those skilled in the art. Many of the general techniques for designing and fabricating the IL-10 variants, including but not limited to human, CMV and/or EBV forms of IL-10, as well as the assays for testing the IL-10 variants, are well known methods that are readily available and detailed in the art. See, e.g., Sambrook, et al., Molecular Cloning: A Laboratory Manual (2nd Edition, 1989); Methods In Enzymology (S. Colowick and N. Kaplan eds., Academic Press, Inc.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition). N-terminal aldehyde based PEGylation chemistry is also well known in the art.

The following terms will be used to describe the various embodiments discussed herein, and are intended to be defined as indicated below.

As used herein in describing the various embodiments, the singular forms “a”, “an” and “the” include plural referents unless the content clearly dictates otherwise.

The term “about”, refers to a deviance of between 0.0001-5% from the indicated number or range of numbers. In one embodiment, the term “about”, refers to a deviance of between 1-10% from the indicated number or range of numbers. In one embodiment, the term “about”, refers to a deviance of up to 25% from the indicated number or range of numbers. In a more specific embodiment, the term “about” refers to a difference of 1-25% in terms of nucleotide sequence homology or amino acid sequence homology when compared to a wild-type sequence.

The term “interleukin-10” or “IL-10” refers to a protein comprising two subunits non-covalently joined to form a homodimer, where IL-10 is an intercalated dimer of two six helix bundle (helix A-F). As used herein, unless otherwise indicated “interleukin-10” and “IL-10” can refer to human IL-10 (“hIL-10”; Genbank Accession No. NP_000563; or U.S. Pat. No. 6,217,857) protein (SEQ ID No: 1) or nucleic acid (SEQ ID No: 2); mouse IL-10 (“mIL-10”; Genbank Accession No: M37897; or U.S. Pat. No. 6,217,857) protein (SEQ ID No: 7) or nucleic acid (SEQ ID No: 8); or viral IL-10, (“vIL-10”). Viral IL-10 homologs maybe derived from EBV or CMV (Genbank Accession Nos. NC_007605 and DQ367962, respectively). The term EBV-IL10 refers to the EBV homolog of IL-10 protein (SEQ ID No: 3) or the nucleic acid (SEQ ID No: 4). The term CMV-IL10 refers to the CMV homolog of IL-10 protein (SEQ ID No: 5) or the nucleic acid (SEQ ID No: 6). The term monomeric IL-10, as used herein, refers to the individual subunits of IL-10 or variant IL-10 that, when non-covalently joined, form a homodimer of IL-10 or variant IL-10. The terms “wild-type,” “wt” and “native” are used interchangeably herein to refer to the sequence of the protein (e.g. IL-10, CMV-IL1 or EBV-IL10) as commonly found in nature in the species of origin of the specific IL-10 in question. For example, the term “wild-type” or “native” EBV-IL10 would thus correspond to an amino acid sequence that is most commonly found in nature.

The term “derive,” “derived,” “derive from,” or “derived from,” is used herein to identify the original source of a molecule, such as a viral form of IL-10 molecule, but is not meant to limit the method in which the molecule is prepare, manufactured, fabricated, or made. This would include methods, such as but not limited to, chemical or recombinant means.

The term “derivative” is intended to include any suitable modification of the reference molecule of interest or of an analog thereof, such as sulfation, acetylation, glycosylation, phosphorylation, polymer conjugation (such as with polyethylene glycol), hesylation, or other addition of foreign moieties, so long as the desired biological activity (e.g., anti-inflammation and/or no T cell stimulation) of the reference molecule or the variant is retained.

The terms “variant,” “analog” and “mutein” refer to biologically active derivatives of the reference molecule, that retain a desired activity, such as, for example, anti-inflammatory activity. Generally, the terms “variant,” “variants,” “analog” and “mutein” as it relates to a polypeptide refers to a compound or compounds having a native polypeptide sequence and structure with one or more amino acid additions, substitutions (that are conservative in nature), and/or deletions, relative to the native molecule. As such, the terms “IL-10 variant”, “variant IL-10,” “IL-10 variant molecule,” and grammatical variations and plural forms thereof are all intended to be equivalent terms that refer to an IL-10 amino acid (or nucleic acid) sequence that differs from wild-type IL-10 anywhere from 1-25% in sequence identity or homology. Thus, for example, an EBV IL-10 variant molecule is one that differs from wild-type EBV IL-10 by having one or more amino acid (or nucleotide sequence encoding the amino acid) additions, substitutions and/or deletions. Thus in one form; an EBV IL-10 variant is one that differs from the wild type sequence of SEQ ID No.:3 by having about 1% to 25% difference in sequence homology, which amounts to about 1-42 amino acid difference.

The term "fusion protein" refers to a combination or conjugation of two or more proteins or polypeptides that results in a novel arrangement of proteins that do not normally exist naturally. The fusion protein is a result of covalent linkages of the two or more proteins or polypeptides. The two or more proteins that make up the fusion protein may be arranged in any configuration from amino-terminal end to carboxy-terminal end. Thus for example, the carboxy-terminal end of one protein may be covalently linked to either the carboxy terminal end or the amino terminal end of another protein. Exemplary fusion proteins may include combining a monomeric IL-10 or monomeric variant IL-10 molecule with one or more antibody variable domains. The fusion proteins may also form dimers or associated with other fusion proteins of the same type, which results in a fusion protein complex. The complexing of the fusion protein may in some cases activate or increase the functionality of a fusion protein when compared to a non-complexed fusion protein. For example, a monomeric IL-10 or monomeric variant IL-10 molecule with one or more antibody variable domains may have limited or decreased capacity to bind to an IL-10 receptor; however, when the fusion protein is complexed, the monomeric forms of IL-10 or variant IL-10 molecule become a homodimer and the variable domains associate into a functional diabody.

A "functional variant" is an IL-10 variant molecule that includes modifications (e.g., additions, substitutions, and/or deletions) that do not destroy the biological activity of the reference molecule. These variants may be "homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions. The functional variant will retain biological activity that is enhanced, diminished or substantially the same as the native molecule. Specifically, the term "variant" IL-10 molecule, which is interchangeable with the terms "engineered" IL-10 molecule or IL-10 variant molecule or IL-10 variant, refers to an IL-10 molecule or protein that includes one or both modifications to the IL-10 receptor binding domain(s) and/or to the regions responsible for forming an inter-domain angle or inter-homodimeric angle in the IL-10 molecule or protein. A variant IL-10 "fusion protein" or "diabody" or "fusion" generally refers to the formation of a fusion protein (or a fusion protein complex) comprising variant IL-10 (in either monomeric form or in homodimeric form) and at least one other protein. As used herein a variant IL-10 "or a fusion protein thereof" may be used throughout this description to describe such a variant IL-10 fusion protein.

An "analog" or "analogs" may include substitutions that are conservative in nature. For example, conservative substitutions might include in kind type substitutions such as, but not limited to (1) an acidic substitution between aspartate and glutamate; (2) a basic substitution between any one of lysine, arginine, or histidine; (3) a non-polar substitution between any one of alanine, valine, leucine, isoleucine, proline, phenylalanine, methionine, or tryptophan; and (4) a uncharged polar substitution between any one of glycine, asparagine, glutamine, cysteine, serine threonine, or tyrosine. Phenylalanine, tryptophan, and tyrosine are sometimes classified as aromatic amino acids. It is also possible that an isolated replacement of leucine with isoleucine or valine, an aspartate with a glutamate, a threonine with a serine, or a similar conservative replacement of an amino acid with a structurally related amino acid may be made so long as the desired and specific biological activity is intact. For example, the polypeptide of interest may include up to about 1-10 conservative or non-conservative amino acid substitutions, or even up to about 15-25 conservative or non-conservative amino acid substitutions, or any integer between 1-50, so long as the desired function of the molecule remains intact. One of skill in the art may readily determine regions of the molecule of interest that can tolerate change well known in the art.

A "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. Preferably, the analog or mutein will retain some biological activity that is enhanced, diminished or substantially the same as the native molecule. Methods for making polypeptide analogs and muteins are well known in the art.

The term "homolog," "homology," "homologous" or "substantially homologous" refers to the percent identity between at least two polynucleotide sequences or at least two polypeptide sequences. Sequences are homologous to each other when the sequences exhibit at least about 50%, preferably at least about 75%, more preferably at least about 80%-85%, preferably at least about 90%, and most preferably at least about 95%-98% sequence identity over a defined length of the molecules.

The term "sequence identity" refers to an exact nucleotide-by-nucleotide or amino acid-by-amino acid correspondence. The sequence identity may range from 100% sequence identity to 50% sequence identity. A percent sequence identity can be determined using a variety of methods including but not limited to a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the identification of percent identity.

The term "fragment" is intended to include a portion molecule of the full-length amino acid or polynucleotide sequence and/or structure. A fragment of a polypeptide may include, for example, a C-terminal deletion, an N-terminal deletion, and/or an internal deletion of the native polypeptide. Active or functional fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as anti-inflammatory activity. As it relates to antibodies, an antibody fragment refers to a portion of an intact antibody comprising an antigen binding site or variable region (heavy chain and/or light chain regions) of the intact antibody. These may include, for example, the Fab, Fab', Fab'-SH, $(Fab')_2$, Fv fragments, diabodies, single chain Fv (ScFv), single chain polypeptides with one light chain variable domain, a fragment having three CDRs of the light chain variable domain or heavy chain variable domain.

The term "substantially purified" generally refers to isolation of a substance such that the substance comprises the majority percent of the sample in which it resides. A substantially purified component comprises 50%, preferably 80%-85%, more preferably 90-95% of the sample. Likewise the term "isolated" is meant, when referring to a polypeptide or a polynucleotide, that the indicated molecule is separate and discrete from the whole organism with which the molecule is found in nature or is present in the substantial absence of other biological macro-molecules of the same type.

The terms "subject," "individual" or "patient" are used interchangeably herein and refer to a vertebrate, preferably a mammal. Mammals include, but are not limited to, murine, rodent, simian, human, farm animals, sport animals, and certain pets.

The term "administering" includes routes of administration which allow the active ingredient of the application to perform their intended function.

A "therapeutically effective amount" as it relates to, for example, administering the EBV-IL-10 variants or fusion proteins thereof described herein, refers to a sufficient amount of the EBV-IL-10 variant or fusion proteins thereof to promote certain biological activities. These might include, for example, suppression of myeloid cell function, enhanced Kupffer cell activity, and/or lack of any effect on $CD8^+$ T cells or enhanced $CD8^+$ T-cell activity as well as blockade of mast cell upregulation of Fc receptor or prevention of degranulation. Thus, an "effective amount" will ameliorate or prevent a symptom or sign of the medical condition. Effective amount also means an amount sufficient to allow or facilitate diagnosis.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

A "chemotherapeutic" agent is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL® Bristol-Myers Squibb Oncology, Princeton, N.J.) and doxetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda® Roche, Switzerland; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above. The term "conjugate," "conjugated," "conjugation," or "conjugating" as used in this application refers to linking of two or more parts of a molecule together. The linking occurs by means of a covalent bond (such as peptide bond).

IL-10 Variant Proteins

The IL-10 variant molecule of the present application includes modifications to any form of IL-10. These modifications to the IL-10 molecule include additions, deletions, and/or substitution of one or more amino acids in regions and/or domains implicated in IL-10 receptor binding and/or those involved in imparting an inter-domain or inter-homodimeric angle in the IL-10 molecule. Exemplary IL-10 sequences that may be of use in constructing the variant IL-10 molecules of the present application include, but are not limited to, homologues from Epstein-Barr virus ("EBV"; see, e.g., Moore et al., Science (1990) 248:1230-1234; Hsu et al., Science (1990) 250:830-832; Suzuki et al., J. Exp. Med. (1995) 182:477-486), cytomegalovirus ("CMV"; see, e.g., Lockridge et al., Virol. (2000) 268:272-280; Kotenko et al., Proc. Natl. Acad. Sci. USA (2000) 97:1695-1700), and equine herpesvirus (see, e.g., Rode et al., Virus Genes (1993) 7:111-116), the OrF virus (see, e.g., Imlach et al., J. Gen. Virol. (2002) 83:1049-1058 and Fleming et al., Virus Genes (2000) 21:85-95). Other representative IL-10 sequences include sequences described in NCBI accession numbers NM010548, AF307012, M37897, M84340 (mouse sequences); U38200 (equine); U39569, AF060520 (feline sequences); U00799 (bovine); U11421, Z29362 (ovine sequences); L26031, L26029 (macaque sequences); AF294758 (monkey); U33843 (canine); AF088887, AF068058 (rabbit sequences); AF012909, AF120030 (woodchuck sequences); AF026277 (possum); AF097510 (guinea pig); U11767 (deer); L37781 (gerbil); AB107649 (llama and camel).

In one embodiment, the IL-10 variant molecules described herein are obtained by modifying the wild-type protein of human (SEQ ID NO.:1), CMV (SEQ ID NO.: 5), EBV (SEQ ID NO.:3) IL-10 sequences, or mouse (SEQ ID No: 7). Representative examples of various IL-10 variant molecules are provided in SEQ ID Nos. 9-23.

Modifications, relative to wild-type IL-10, comprise additions, deletions, and/or substitutions of one or more amino acids in the regions responsible for (i) IL-10 receptor binding and/or (ii) the formation of the inter-domain or inter-homodimeric angle of the IL-10 molecule.

Variant IL-10 Molecules: IL-10 Receptor Binding Regions

The regions responsible for receptor binding include any amino acid portion located within regions that are directly involved or responsible for the binding of IL-10 to the IL-10 receptor 1 (IL10R1) and/or IL-10 receptor 2 (IL10R2). These regions may include, for example, discontinuous portions of the IL-10 molecule previously discussed and mapped in the art (see, e.g., Yoon 2005; Josephson 2001). For example, modifications to any region, such as, but not limited to, helix A, helix F, and AB loop, responsible for forming the contact points and clefts associated with IL-10 binding to the 1-10 receptor are envisioned in this application. In a preferred embodiment, the modification (e.g., addition, deletion, and/or substitution) to the receptor binding domain includes amino acid 31 and/or 75 of SEQ ID No. 3. In a particularly preferred embodiment, the modifications include substituting the valine at position 31 to a leucine (V31L, herein termed “DV05”) in SEQ ID No. 3, substituting the alanine at position 75 to an isoleucine (A75I, herein termed “DV06”) in SEQ ID No. 3, or both the V31L and A75I substitutions (herein termed “DV07”) in SEQ ID No. 3. In one aspect, DV05 is SEQ ID No: 55, DV06 is SEQ ID No: 57, and DV07 is SEQ ID No: 59.

Figure 1:
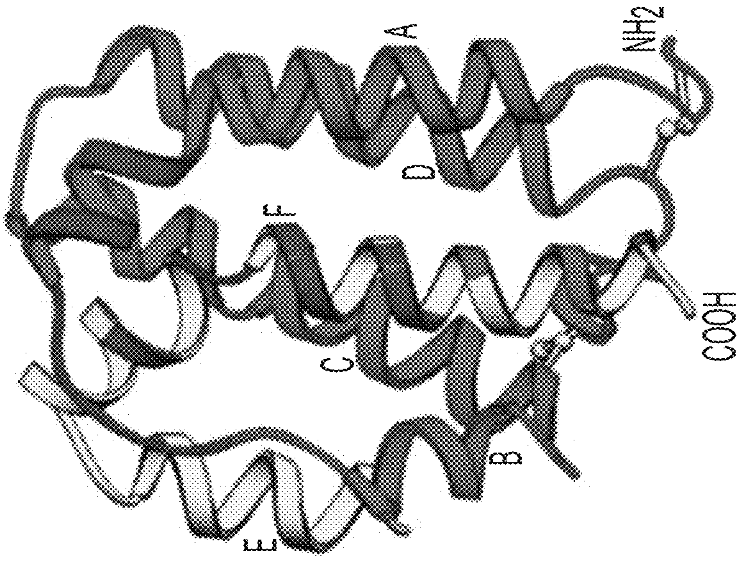
FIG. 1 shows a ribbon diagram (Josephson et al, *Immunity,* 15, p. 35-46) of a monomeric IL-10 molecule. Portions highlighted in red indicates site I receptor contact interface and green indicates site II receptor contact interface.

In one embodiment, the modifications to the receptor binding domain include any one or more of the site Ia and/or site Ib interface contact points discussed by Josephson et al (*Immunity,* 2001, 15, p. 35-46, FIG. 1). In one embodiment of the application, the site Ia interface contact points include one or more amino acids located in the bend of helix F and in the AB loop. In another embodiment, the site Ib interface contact points include one or more amino acids located in the N-terminus of helix A and the C-terminus of helix F. In another embodiment, any one or more amino acids located on IL-10 responsible for receptor binding will include any one or more of 1-10 amino acids within helix A and 1-7 amino acids within AB loop. In another embodiment, the receptor binding region may include one or more modifications of the following amino acids or 1-10 amino acids centered around thereof, wherein the amino acids are Glu-142, Lys-138, Asp-144, Gln-38, Ser-141, Asp-44, Gln-42, Gln-38, Arg-27, Glu-151, Arg-24, Pro-20, Ile-158, or any combination thereof.

In one aspect, the modifications to the receptor binding domain include any one or more of the site IIa and/or site IIb interface contact points discussed by Josephson et al (Immunity, 2001, 15, p. 35-46, FIG. 1). In one embodiment of the application, the site Ha interface contact points include one or more amino acids located in the DE loop. In another embodiment, the receptor binding region may include one or more modifications of the following amino acids or 1-10 amino acids centered around thereof, wherein the amino acids are Ser-11, Thr-13, Asn-18, Arg-104, Arg-107, or any combination thereof. In one embodiment, the variant IL-10 molecule will comprise 1-100 (or any integer therein) amino acid additions, deletions, and/or substitutions that impact the receptor binding domain, wherein such additions, deletions, and/or substitutions either increase or decrease binding affinity of the variant IL-O molecule to the IL-10 receptor.

Variant IL-1 Molecules: Inter-Domain Angle Modifications.

The regions responsible for the formation of the inter-domain (or inter-homodimeric, which is used interchangeably) angle of the IL-10 molecule include any amino acid portion located within regions that are directly involved or responsible for the formation of specific interdomain angles of IL-10 homodimers. Wild-type IL-10 forms an “L-shaped” dimer when two monomeric units of IL-10 intertwine in anti-parallel fashion. The resulting interdomain angle for human IL-10 and EBV-1L10 is reported to be approximately 89 and 97 degrees, respectively. In order to tune the signal transduction of the IL-10 receptor, in one embodiment, the present application seeks to modify the amino acids within the DE loop, portions of helix D or helix E responsible for the formation of the L-shaped dimer in each monomer responsible for the formation of the inter-domain angle. In another embodiment, the regions responsible for the inter-domain angle includes the about 12 amino acid linker region located between helix D and helix E of the IL-10 protein. Modifications, by addition, deletion, or substitution, result in a constrained or relaxed IL-10 inter-domain angle when compared to either human IL-10 or EBV-IL10. When the monomeric IL-10 molecule is modified, resulting in a constrained/tight/closed or relaxed/loose/opened IL-10 inter-domain angle when homodimerized, the modified IL-10 molecule will produce a variant IL-10 molecule that has an altered inter-domain angle that engages and modulates its cognate receptor (IL-10 receptor). In another embodiment, the substitution includes introducing a proline within the amino acid segment located between the D helix and E helix of EBV-IL10 and/or between the C helix and the D helix.

Thus, in an embodiment, the variant IL-10 molecule will comprise one or more additions, deletions, and/or substitutions that exhibit an altered inter-molecular angle or altered inter-domain angle, when compared to the wild-type IL-10. The altered inter-molecular angle or altered inter-domain angle can dimerize with an identical or different variant IL-10 molecule to result in a variant IL-10 molecule that engages the IL-10 receptor with a different angle of engagement when compared to the wild-type IL-10 molecule. The variant IL-10 molecule’s different angle of engagement results in an ability to modulate or “tune” the signal transduction of the IL-10 receptor to either activate or suppress inflammation and/or immune responses. In a preferred embodiment, the variant IL-10 molecule is an EBV-IL10. In another preferred embodiment, the variant IL-10 molecule uses the EBV-IL10 molecule as a basis for modification. In yet another embodiment, the variant IL-10 molecule is a hybrid molecule taking portions and domains from other IL-10 molecules (such as but not limited to human IL-10, mouse IL-10, and/or CMV-IL10).

In another preferred embodiment, the variant IL-10 molecule produces a relaxed inter-domain angle that will suppress inflammatory cell (myeloid lineage cells) response, and not drive the activation of lymphocytic cells, such as T-cells. When coupled with modifications to the receptor binding domain, preferably modifications that result in lowered or unchanged receptor affinity, the variant IL-10 molecules with the relaxed inter-domain angle will be effective in suppressing myeloid cells (monocytes, macrophages, neutrophil, granulocyte, mast cells, Kupffer cells) cytokine secretion in response to pro-inflammatory stimuli. This configuration of the variant IL-10 molecule is useful, for example in treating inflammatory diseases such as, but not limited to IBD, Crohn's disease, psoriasis, rheumatoid arthritis, NAFLD, and NASH.

In another preferred embodiment, the variant IL-10 molecule produces a constrained inter-domain angle that will enhance the activation of immune cells, such as T-cells. When coupled with modifications to the receptor binding domain, preferably modifications that result in higher receptor affinity, the variant IL-10 molecules with the constrained inter-domain angle will be effective in enhancing, for example $CD8^+$ T-cells, NK cells, and Kupffer cell scavenging. This configuration of the variant IL-10 molecule is useful, for example, in treating a variety of solid and hematological cancers including metastatic cancers.

The regions responsible for the formation of the inter-domain angle may be continuous or discontinuous portions located within the IL-10 molecule. In one embodiment, the inter-domain angle for the IL-10 variant molecule will have a degree change*of 1-25 degrees, in another preferred embodiment, the degree change is 1-10 degrees, in a more preferred embodiment, the degree change is 1-5 degrees, in a most preferred embodiment, the degree change is less than 5 degrees. In one embodiment, the variant IL-10 molecule will comprise 1-100 (or any integer therein) amino acid additions, deletions, and/or substitutions that impact the inter-domain angle.

In one embodiment of the application, the variant IL-10 molecules will be designed and created with the assistance of computer-based modeling to predict the region or regions most responsible for IL-10 receptor binding and/or the inter-domain angles. The computer-based modeling will assist in providing a faster and more efficient means of predicting the regions that will benefit the most from the modifications to the receptor binding domain and/or the inter-domain angles.

In another embodiment, the molecule of the present application include derivatives of the variant IL-10 molecules. These might include modifications to the variant molecule to include entities that increase the size, half-life, and bioavailability of the variant molecules.

Variant IL-10 Molecules: PEG Modifications

In one embodiment, the variant IL-10 molecules may include the addition of polyethylene glycol (PEG). PEGylated IL-0 variants will include the attachment of at least one PEG molecule. Without being bound to any particular theory, attachment of PEG to the IL-10 variant might protect against proteolysis, decrease immunogenicity, facilitate destabilization of the IL-10 variant on the receptor to maintain its suppressive effects on myeloid cells and prevent activation of T cells.

In its most common form, PEG is a linear or branched polyether terminated with hydroxyl groups and having the general structure:

$$HO—(CH_2CH_2O)_n—CH_2CH_2—OH$$

Methods of coupling PEG to variant IL-10 molecules of the present application will follow those techniques/protocols already established in the art. For example, conjugating or coupling PEG requires activating the PEG by preparing a derivative of the PEG having a functional group at one or both termini. The most common route for PEG conjugation of proteins has been to activate the PEG with functional groups suitable for reaction with lysine and N-terminal amino acid groups. In particular, the most common reactive groups involved in coupling of PEG to polypeptides are the alpha or epsilon amino groups of lysine.

The reaction of a PEGylation linker with a variant IL-10 molecule leads to the attachment of the PEG moiety predominantly at the following sites: the alpha amino group at the N-terminus of the protein, the epsilon amino group on the side chain of lysine residues, and the imidazole group on the side chain of histidine residues. In some embodiments, because the variant IL-10 molecules are recombinant proteins that possess a single alpha and a number of epsilon amino and imidazole groups, numerous positional isomers can be generated depending on the linker chemistry.

Two widely used first generation activated monomethoxy PEGs (mPEGs) were succinimidyl carbonate PEG (SC-PEG; see, e.g., Zalipsky, et al. (1992) Biotechnol. Appl. Biochem 15:100-114; and Miron and Wilcheck (1993) Bioconjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on IFNα has been shown to be a hydrolytically unstable imidazolecarbamate linkage (see, e.g., Lee and McNemar, U.S. Pat. No. 5,985,263, which are incorporated by reference in their entirety).

Second generation PEGylation technology has been designed to avoid these unstable linkages as well as the lack of selectivity in residue reactivity. Use of a PEG-aldehyde linker targets a single site on the N-terminus of a polypeptide and/or protein subunit through reductive amination. IL-10 may be PEGylated using different types of linkers and pH to arrive at a various forms of a PEGylated molecule (see, e.g., U.S. Pat. Nos. 5,252,714, 5,643,575, 5,919,455, 5,932,462, 5,985,263, 7,052,686, which are all incorporate by reference in their entirety).

IL-10 Mimetic Molecules

In another embodiment, the present application includes mimetic molecules that mirror the biological function of the IL-10 variant molecules. These mimetics include, but are not limited to, peptides, small molecules, modified hormones, and antibodies that have structures and or functions that are same or substantially the same as those produced from the variant IL-10 molecules. IL-10 mimetic molecules that may form the basis for modification to replicate or mirror the IL-10 variant molecules include those described in US20080139478, US20120238505, and/or US20150218222, all of which are incorporated by reference in their entirety.

IL-10 Hybrid Molecules and IL-10 Fusion Proteins

In another embodiment, the present application includes IL-10 variant molecules that are hybrid molecules composed of portions obtained from human IL-10, EBV-IL10, and/or CMV-IL10. For example, different domains within each of human IL-10, EBV-IL10 and/or CMV-IL10 may be combined together to create a hybrid molecule, such that the combination adopts all or portions of the receptor binding domain and/or the domains responsible for the interdomain angle in IL-10.

In one other embodiment, the variant IL-10 molecule is part of an engineered fusion protein. The linker or spacer can be a random amino acid sequence (such as SSGGGGS (SEQ ID No.: 30, GGGGSGGGGSGGGGS (SEQ ID No.: 31) or SSGGGGSGGGGSGGGGS (SEQ ID No. 54)), constant region of an antibody, a scFv or a diabody. The constant region can be derived from, but not limited to IgG1, IgG2, IgG3, IgG4, IgA, IgM, IgD, or IgE. The linker or spacer can be preferably the constant heavy (CH) region 1, CH2, or CH3. In a more preferred embodiment, the linker of spacer is a random amino acid sequence of SEQ ID Nos: 30 and/or 31. In another aspect, the linker or spacer may further comprise at least two interchain disulfide bonds.

The fusion protein may also include at least one monomer of IL-10 or IL-10 variant molecule conjugated at the fusion protein's N-terminal end, the C-terminal end, or both. In another embodiment, the fusion protein comprising IL-10 or IL-10 variant may also include at least one cytokine conjugated at the terminal end opposite of the IL-10 or variant IL-10 and includes IL-2, IL-7, IL-15, IL-26, IL-27, IL-28, IL-29, IL-10, IL-10 variant molecule, IFN-alpha, TGF-beta, basic-FGF, EGF, PDGF, IL-4, IL-11, or IL-13 or any combination thereof. In some preferred embodiments, the fusion protein comprises two monomeric forms of IL-10 or IL-10 variant molecules conjugated at the N-terminal end of the fusion protein and two IL-10 or IL-10 variant molecules conjugated at the C-terminal end of the fusion protein; the fusion protein comprises two monomeric forms of IL-10 or IL-10 variant molecules conjugated at the N-terminal end of the fusion protein and at least one IL-2 molecules conjugated at the C-terminal end of the fusion protein; the fusion protein comprises two IL-10 or IL-10 variant molecules conjugated at the N-terminal end of the fusion protein and at least one IL-15 molecules conjugated at the C-terminal end of the fusion protein. In another embodiment, the C-terminal end of the fusion protein may have at least two different cytokines selected from IL-2, IL-7, IL-15, IL-26, IL-27, IL-28, IL-29, IL-10, IL-10 variant molecule, IFN-alpha, TGF-beta, basic-FGF, EGF, PDGF, IL-4, IL-11, or IL-13.

In another embodiment, the fusion protein is fabricated using a single chain variable fragment (scFv), a diabody, Fab, or any antibody fragment as the base scaffold onto which one monomer or two monomers of IL-10, one monomer or two monomers of a IL-10 variant molecule, IL-2, IL-7, IL-15, IL-26, IL-27, IL-28, IL-29, IFN-alpha, TGF-beta, basic-FGF, EGF, PDGF, IL-4, IL-11, or IL-13, or combinations thereof are conjugated.

In one particularly preferred embodiment, the fusion protein comprises at least one variable region, having a variable heavy chain (VH) and/or variable light chain (VL), linked to an IL-10 or 1-10 variant molecule. In this configuration, the fusion protein comprises an IL-10 monomer or variant IL-10 monomer linked to at least one variable region of an antibody. In one aspect, this fusion protein is a linear contiguous sequence comprising an IL-10 monomer or IL-10 monomer variant molecule linked to a VH, linked to a VL, linked to an IL-10 monomer The variable region of the antibody can be a variable heavy (VH) chain region, a variable light (VL) chain region, or both. A first fusion protein comprises a protein sequence having a linear contiguous configuration such that an IL-10 monomer or a variant IL-10 monomer is conjugated to a variable region's (VH or VL or both) carboxy terminal end. A second fusion protein may comprise a protein sequence having a linear contiguous configuration such that an IL-10 monomer or a variant IL-10 monomer is linked to a variable region's (VH or VL or both) amino terminal end. A representative example of the first fusion protein described above may include the following configuration:

a) $_{NH2}$(Ab1VL)$_{COOH}$-(linker)-$_{NH2}$(monoIL10)$_{COOH}$

A representative example of the second fusion protein described above may include the following configuration:

b) $_{NH2}$(monoIL10)$_{COOH}$-(linker)-$_{NH2}$(Ab$_1$VH)$_{COOH}$

Together, the first (a) and second (b) fusion proteins form a functional protein complex in an anti-parallel manner, whereby the terminally linked monomers of IL-10 or variant IL-10 form a functional homodimer and the variable regions together are capable of forming a functional antigen binding site ("ABS") (see e.g., FIGS. 9(*a*)-(*f*)).

In an alternative embodiment, the IL-10 monomer or variant IL-10 monomer may be conjugated to at least two variable regions from the same antibody or from two different antibodies. In this configuration, the at least two variable regions are a VH and VL. An example of such a configuration would include a first fusion protein with a linear contiguous protein sequence of a VH region of a first antibody linked at its carboxy terminal end to an amino terminal end of a VL region of the second antibody subsequently linked to the amino terminal end of a monomer of IL-10 or a monomer of an IL-10 variant molecule. An alternative configuration would include a second fusion protein with a linear contiguous protein sequence of a monomer IL-10 or a monomer of an IL-10 variant molecule linked at its carboxy terminal end to an amino terminal end of a VH region of the second antibody subsequently linked to an amino terminal end of a VL region of the first antibody. A representative example of the first fusion protein described above may include the following configuration:

a) $_{NH2}$(Ab$_1$-VH)$_{COOH—}$-(linker)-$_{NH2}$(Ab$_2$VL)$_{COOH}$-(linker)-$_{NH2}$(monoIL10)$_{COOH}$ A representative example of the second fusion protein described above may include the following configuration:

b) $_{NH2}$(monoIL10)$_{COOH}$-(linker)-$_{NH2}$(Ab$_2$VH)$_{COOH}$-(linker)-$_{NH2}$(Ab$_1$-VL)$_{COOH}$ Together, the first (a) and second (b) fusion proteins form a functional protein complex in an anti-parallel manner, whereby the terminally linked monomers of IL-10 or variant IL-10 form a functional homodimer and the variable regions together are capable of forming an ABS (see e.g., FIGS. 9(*a*)-(*c*)).

In yet another embodiment, the fusion protein comprises two monomers of IL-10 or two monomers of variant IL-10 that are fused together and one or more VH and VL regions. Each monomer is individually linked to one or more VH region and/or VL region of an antibody. When more than one VH and/or VL region is used in this fusion protein configuration, the VH and VL regions may be from the same antibody or from at least two different antibodies. In one particular configuration of this fusion protein, the VH or VL region is linked to the amino terminal end of a first monomer which is then linked by its carboxy end to the amino terminal end of a second monomer which is then linked to the amino terminal end of a VL or VH. Optionally, additional VH or VL regions may be linked to the amino or carboxy terminal ends, wherein the VH or VL regions may be from the same antibody or from a different antibody. Representative examples of the fusion protein described above may include the following configurations (see e.g., FIGS. 10(*d*)-(*f*)):

$_{NH2}$(Ab$_1$-VH)$_{COOH—}$-(linker)-$_{NH2}$(monoIL10)$_{COOH}$-(linker)-$_{NH2}$(monoIL10)$_{COOH—}$(linker)-$_{NH2}$(Ab$_1$-VL)$_{COOH}$ The fusion protein described above will be capable of folding in a manner that allows the monomers of IL-10 to form a homodimer and the variable domains (VH and VL) of an antibody to form a functional ABS.

In another embodiment, the fusion protein comprises two monomers of IL-10 or two monomers of variant IL-10 located at the opposing terminal ends of the fusion protein and at least one VH and VL region, wherein the VH and VL regions are linked together. In this configuration, the VH and VL regions are fused together and each monomer is individually linked to either a VL region or a VH region of a first antibody. In this configuration, the IL-10 monomers or the monomers of variant IL-10 are each individually linked to either a VH or VL of a first antibody.

A representative example of the fusion protein described above may include the following configurations (see, e.g., FIGS. 10(*a*)-(*c*)):

a) $_{NH2}$(monoIL10)$_{COOH}$-(linker)-$_{NH2}$(Ab$_1$-VH)$_{COOH}$-(linker)-$_{NH2}$(Ab$_1$-VL)$_{COOH}$-(linker)-$_{NH2}$(monoIL10)$_{COOH}$ b) $_{NH2}$(monoIL10)$_{COOH}$-(linker)-$_{NH2}$(Ab$_1$-VL)$_{COOH}$-(linker)-$_{NH2}$(Ab$_1$-VH)$_{COOH}$-(linker)-$_{NH2}$(monoIL10)$_{COOH}$ The monomer of IL-1 or the monomer of a variant IL-10 may be linked to the VH or VL sequence through a linker sequence. The linker can be a carboxy terminal linker linking a carboxy end of a variable chain region (VH or VL) to an amino terminal end of a monomer of IL-1 or a monomeric IL-10 variant molecule. Alternatively, the linker can be an amino terminal linker whereby the carboxy terminal end of a monomeric IL-10 or a monomeric IL-10 variant molecule is linked to the amino terminal end of a variable chain region (VH or VL).

Thus, in one form, the fusion protein comprises a monomeric IL-1 molecule or a variant IL-10 molecule linked to two variable regions from at least two different antibodies, wherein the two variable regions are configured as a VH region from a first antibody linked to a VL region from a second antibody or a VL from the first antibody linked to a VH from the second antibody. The fusion protein according to this form may include monomeric IL-10 molecule or a variant thereof including at least one amino acid substitution that increases or decreases affinity to an IL-10 receptor. The amino acid substitution impacting IL-10 receptor binding may occur in a human, CMV or EBV IL-10. The amino acid substitution may preferably be in an EBV IL-10 and include amino acid substitution at position 31, 75, or both. The amino acid substitutions may include any one or more of a V31L or A75I substitution or both. In addition to the amino acid substitutions impacting IL-10 receptor binding affinity, the IL-10 variant may also include modifications that impact the inter-domain angle. In another embodiment, the fusion protein comprises a configuration selected from: (a) a VH region of the first antibody linked at its carboxy terminal end to an amino terminal end of a VL region of the second antibody subsequently linked to a carboxy terminal end of a monomer of IL-10 or a variant thereof; or (b) an IL-10 molecule or a variant thereof linked at its carboxy terminal end to an amino terminal end of a VH region of the second antibody subsequently linked to an amino terminal end of a VL region of the first antibody. These fusion protein configurations include, in one preferred embodiment a sequence of SEQ ID Nos.: 24-28, 29, and 33-53. These fusion proteins sequences are capable of forming a complex wherein the monomers of IL-10 or monomers of variant IL-10 are capable of forming a homodimer. Such a complex may include and/or configured as a diabody complex.

In another form, the fusion protein may be fashioned as an immunoconjugate comprising a first fusion protein comprising at its amino terminal end a heavy chain variable region (VH) of a first antibody linked to a light chain variable region (VL) of a second antibody further linked to a monomer of IL-10; and a second fusion protein comprising at its amino-terminal end a monomer of IL-10 linked to a VH of the second antibody further linked to a VL of the first antibody, wherein the VH and VL of the first and second antibodies associate into a diabody and the monomers of IL-10 form a functional dimeric IL-10 molecule. In another preferred embodiment, an immunoconjugate complex comprises a first fusion protein comprising at its amino terminal end a VH region of a first antibody and a monomeric IL-10 molecule linked by its amino terminal end; and a second fusion protein comprising at its amino terminal end a monomer of IL-10 linked to a VL of the first antibody, wherein the VH region of the first antibody associates with the VL region of first antibody thereby allowing the monomeric IL-10 molecules on each peptide chain to form a functional IL-10 dimer. The monomer(s) of IL-10 or monomer(s) variant IL-10 may include, as described above, amino acid modifications that impact IL-10 receptor binding and/or inter-domain angle. In another preferred embodiment, an immunoconjugate complex comprises a first fusion protein comprising at its amino terminal end a VH region of a first antibody linked to a monomeric IL-10 molecule; and a second fusion protein comprising at its amino terminal end a monomer of IL-10 linked to a VL of the first antibody, wherein the VH region of the first antibody associates with the VL region of first antibody thereby allowing the monomeric IL-10 molecules on each peptide chain to form a functional IL-10 dimer. In yet another embodiment, the immunoconjugate comprises at its amino terminal end a monomer of a first IL-10 (or IL-10 variant molecule) monomer linked to a VH region of a first antibody linked to a VL region of the first antibody linked to a monomer of a second IL-10 (or IL-10 variant molecule), wherein the two IL-10 monomers are able to associate together to form a functional dimer of IL-10. The VH and VL regions described are capable of forming an antigen binding site that specifically target an antigen (e.g., receptor, protein, nucleic acid, etc.). Thus, there are two chains, Chain 1 and Chain 2 which together for a fusion protein complex that creates a functioning IL-10 (or IL-10 variant molecule) homodimer. Representative fusion protein chains (i.e., Chain 1 and Chain 2) include the following:

| Chain 1 | Chain 2 |
|---|---|
| SEQ ID No: 24 | SEQ ID No: 25 |
| SEQ ID No: 26 | SEQ ID No: 27 |
| SEQ ID No: 28 | SEQ ID No: 29 |
| SEQ ID No: 35 | SEQ ID No: 36 |
| SEQ ID No: 38 | SEQ ID No: 39 |
| SEQ ID No: 41 | SEQ ID No: 42 |
| SEQ ID No: 46 | SEQ ID No: 47 |
| SEQ ID No: 48 | SEQ ID No: 49 |
| SEQ ID No: 50 | SEQ ID No: 51 |

The fusion proteins include a VH and VL pair from at least one antibody. The VH and VL pair act as a scaffolding onto which monomers of IL-10 or variants thereof may be attached such that may be able to homodimerize into a functioning IL-10 molecule. A person of skill in the art will therefore appreciate that the VH and VL scaffolding used in the fusion protein can be selected based on the desired physical attributes needed for proper IL-10 or IL-10 variant protein dimerization and/or the desire to maintain VH and VL targeting ability. Likewise, a person of skill will also understand that the CDR regions within the VH and VL pair may also be substituted with other CDR regions to obtain a specifically targeted fusion protein. It is also envisioned that if the fusion protein is not intended to target any specific antigen, a VH and VL pair may be selected as the scaffolding that does not target any particular antigen (or is an antigen in low abundance in vivo), such as the VH and VL pair from an anti-HIV and/or anti-Ebola antibody. The fusion protein may comprises a range of 1-4 variable regions. The variable regions may be from the same antibody or from at least two different antibodies. The antibody variable chains can be obtained or derived from a plurality of antibodies (e.g., those targeting proteins, cellular receptors, and/or tumor associated antigens, etc.). In another embodiment, the variable regions are obtained from antibodies that target antigens associated with various diseases (e.g., cancer) or those that are not typically found or rarely found in the serum of a healthy subject, for example variable regions from antibodies directed to EGFR, PDGFR, VEGFR, Her2Neu, FGFR, GPC3, or other tumor associated antigens, MadCam, ICAM, VCAM, or other inflammation associated cell surface proteins, HIV and/or Ebola. Thus, in one embodiment, the variable regions are obtained or derived from anti-EGFR, anti-MadCam, anti-HIV (Chan et al, J. Virol, 2018, 92(18): e006411-19), anti-ICAM, anti-VCAM, or anti-Ebola (US Published Application 2018/0180614, incorporated by reference in its entirety, especially mAbs described in Tables 2, 3, and 4) antibodies, for example. In another embodiment, the variable regions are obtained or derived from antibodies capable of enriching the concentration of cytokines, such as IL-10, to a specific target area so as to enable IL-10 to elicit its biological effect. Such an antibody might include those that target overexpressed or upregulated receptors or antigens in certain diseased regions or those that are specifically expressed in certain impacted areas. For example, the variable regions might be obtained from antibodies specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; and SR-J1 to name a few. A monomer of IL-10 (e.g., human, CMV, or EBV) or variant IL-10 molecule (described herein) is conjugated to either the amino terminal end or the carboxy terminal end of a variable region (VH or VL), such that the IL-10 or variant IL-10 molecule is able to dimerize with one another.

The fusion protein or fusion protein complex may also have an antigen targeting functionality. The fusion protein or fusion protein complex will comprise VH and VL regions that are able to associate together to form an antigen binding site or ABS. In some configurations, the IL-10 or IL-10 variant molecule or monomers thereof will be covalently linked to the end comprising the antigen binding site. These targeting fusion proteins may comprise at least one functioning variable region or paired VH and VL at one end of the fusion protein such that the fusion protein retains the capacity to target an antigen as well as having a functioning homodimer of an IL-10 or IL-10 variant molecule (see, FIGS. 9(*a*)-(*f*) and 10(*a*)-(*f*)). The variable regions may be further modified (e.g., by addition, subtraction, or substitution) by altering one or more amino acid that reduce antigenicity in a subject. The VH and VL pair form a scaffolding onto which CDR regions obtained for a plurality of antibodies can be grafted. Such antibody CDR regions include those antibodies known and described above. For example, the CDR regions from any antibody may be grafted onto a VH and VL pair such as those described in SEQ ID Nos: 37, 44, or 45 or those fusion proteins that are capable of forming a fusion protein complex such as those described in SEQ ID Nos: 46 and 47; 48 and 49; or 50 and 51. The CDR regions in the above described VH and VL scaffolding will include the following number of amino acid positions available for CDR engraftment/insertion:

| | |
|---|---|
| Heavy chain CDR1 | 3-7 amino acids |
| Heavy chain CDR2 | 7-11 amino acids |
| Heavy chain CDR3 | 7-11 amino acids |
| Light chain CDR1 | 9-14 amino acids |
| Light chain CDR2 | 5-9 amino acids |
| Light chain CDR3 | 7-11 amino acids |

In another aspect, the fusion protein described above may be represented by one of the following general formula:

1) $IL10\text{-}L^1\text{-}X^1\text{-}L^1\text{-}X^2\text{-}L^1\text{-}IL10$ (Formula I);

2) $(Z)_n\text{-}X^1\text{-}L^2\text{-}Y^2\text{-}L^1\text{-}IL10$ (Formula II);

3) $IL10\text{-}L^1\text{-}Y^1\text{-}L^2\text{-}X^2\text{-}(Z)_n$ (Formula III);

4) $X^1\text{-}L^2\text{-}X^2\text{-}L^1\text{-}IL10$ (Formula IV);

5) $IL10\text{-}L^1\text{-}X^1\text{-}L^2\text{-}X^2$ (Formula V);

6) $X^1\text{-}L^1\text{-}IL10$ (Formula VI); and

7) $IL10\text{-}L^1\text{-}X^2$ (Formula VII)

wherein

"IL-10" is human IL-10 (SEQ ID No: 1); EBV IL-10 (SEQ ID No: 3), DV05 (SEQ ID No:14, 18, or 55), DV06 (SEQ ID No: 15, 19, or 57), or DV07 (SEQ ID No: 16, 20, or 59), in a preferred embodiment, "IL-10" consists of DV05, DV06, or DV07, more preferably "IL-10" consists of SEQ ID Nos: 55, 57, or 59;

"$L^1$" is a linker of SEQ ID No: 31 or 54;

"$L^2$" is a linker of SEQ ID No: 30;

"$X^1$" is a VH region obtained from a first antibody specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; SR-J1; HIV, or Ebola;

"$X^2$" is a VL region obtained from the same antibody as $X_1$;

"$Y^1$" is VH region obtained from a second antibody specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, 37 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; SR-J1; HIV, or Ebola;

"$Y^2$" is a VL region obtained from the same antibody as $Y_1$;

wherein X and Y are obtained from the same or different antibody;

"Z" is a cytokine selected from IL-6, IL-4, IL-1, IL-2, IL-3, IL-5, IL-7, IL-8, IL-9, IL_15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13;

"n" is an integer selected from 0-2.

In an embodiment, the substituents of Formula I-VI, above, is preferably selected from the following: IL-10 is preferably DV05, DV06, or DV07, more preferably IL-10 consists of a DV05, DV06, or DV07 or most preferably IL-10 consists of SEQ ID No: 55, 57, or 59; $X_1$ and X2 are preferably an anti-EGFR, anti-PDGFR, anti-FGFR, anti-VEGF, anti-Her2Neu, anti-GPC3, anti-MAdCAM, anti-ICAM-1, -2, -3, -4, anti-VCAM, anti-HIV, or anti-Ebola; Y1 and Y2 are preferably anti-EGFR, anti-MAdCAM, anti-ICAM-1, -2, -3, -4, anti-VCAM, anti-HIV, or anti-Ebola; Z is selected from IL-2, IL-7, or IL-15; and n is 1. In a most preferred embodiment, the fusion proteins are anyone of SEQ ID Nos: 33-53, 61, 63, 65, or 67. Those of skill in the art will understand that the presence of a Histidine tag is used in the purification process of the fusion protein and maybe left intact or removed from the final product. Those of skill in the art will also understand that the VH and VL framework regions of any of the antibodies described above may be substituted with other complementary-determining regions (CDR) regions. For example, if the VH and VL regions are from an anti-Ebola antibody, the six CDR regions (i.e., CDRs 1-3 of both the VH and VL) may be substituted with the 6 CDR regions of an anti-EGFR antibody (e.g., cetuximab). Thus, in one preferred embodiment, the fusion protein is SEQ ID Nos: 33-34, 52, or 53. In another preferred embodiment, the fusion protein is one having the scaffolding represented by SEQ ID Nos: 37; 44; 45; 46-47; 48-49; or 50-51, where any 6 CDR regions from any antibody may be grafted. In other preferred embodiments, the CDR regions from the VH and VL regions of an anti-Ebola antibody may be grafted with the CDR regions from an anti-MAdCAM, anti-VCAM, or anti-ICAM-1, -2, -3, -4 antibody, wherein in a preferred embodiment the CDR regions may be grafted into a fusion protein of SEQ ID No: 37. The fusion proteins as described in the formulas II and III; formulas IV and V; and formulas VI and VII, above are designed to associate together to forma biologically active homodimer of IL-10 (or variant thereof). The fusion proteins described above are designed to either be non-targeting or targeting depending on the pair of VH and VL regions selected and/or the CDR regions engrafted into the VH and VL. The term "non-targeting" is meant to describe a VH and VL region that is not able to target to a specific antigen located in vivo because the antigen is not present or the antigen binding site (ABS) has been disabled or modified to eliminate the ABS functionality.

The fusion proteins described above may be further conjugated to accessory proteins/molecules. An accessory protein as used herein describes a protein that is conjugated to the fusion protein or fusion protein complex such that it is linked to the side that is opposite that of the IL-10 monomer or variant IL-10 monomer molecule. The addition of the accessory protein effectively create a multifunctional molecule that incorporates both IL-10 or IL-10 variant molecule functionality and the functionality of the accessory protein. Attachment of the accessory proteins (e.g., cytokines IL-2, IL-7, IL-12, IL-15, etc.) may be attached, for example, to the fusion protein comprising the VH and VL scaffolding at the N-terminal end of VH region. For example, as it applies to fusion proteins or fusion protein complexes for treating oncology, the accessory protein includes, but is not limited to, IL-10, IL-10 variant molecule IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13 or any combination thereof. As it applies to fusion proteins or fusion protein complexes for treating inflammatory diseases, the accessory protein includes, but is not limited to TGFβ. As it applies to fusion proteins or fusion protein complexes for treating autoimmune diseases (such as but not limited to fatty liver disease), the accessory molecule includes, but is not limited to obticholic acid, aramchol, elafibranor, liraglutide, selonsertib, or simtuzumab. The accessory proteins defined above, when described using formulas I-V above may be attached to the substituent X1 or Y1, at the N-terminal side of the VH portion of the scaffolding.

The fusion proteins described above may also include additional amino acid sequences that aid in the recovery or purification of the fusion proteins during the manufacturing process. These may include various sequence modifications or affinity tags, such as but not limited to protein A, albumin-binding protein, alkaline phosphatase, FLAG epitope, galactose-binding protein, histidine tags, and any other tags that are well known in the art. See, e.g., Kimple et al (Curr. Protoc. Protein Sci., 2013, 73:Unit 9.9, Table 9.91, incorporated by reference in its entirety). In one aspect, the affinity tag is an histidine tag having an amino acid sequence of HHHHHH (SEQ ID No.: 32). The histidine tag may be removed or left intact from the final product. In another embodiment, the affinity tag is a protein A modification that is incorporated into the fusion protein (e.g., into the VH region of the fusion proteins described herein), such as those described in SEQ ID Nos: 34 or 44-53. A person of skill in the art will understand that any fusion protein sequence described herein can be modified to incorporate a protein A modification by inserting amino acid point substitutions within the antibody framework regions as described in the art.

In yet another embodiment, the various fusion proteins described above may be used in a method of treating cancer, treating or preventing IBD or Crohn's disease, autoimmune disease, NAFLD, or NASH.

IL-10 Variant Polynucleotides

Also within the scope of the present application includes polynucleotide sequences that encode for the variant IL-10 molecules and the various fusion proteins and/or immunocytokines described above. Upon localization of key IL-10 receptor binding regions and/or regions for inter-domain angle in the variant IL-10 molecules of the present application, the DNA modifications necessary to effect the desired modifications into amino acid sequences are within the skill set of a person of skill in the art. Such modifications will employ conventional recombinant DNA techniques and methods. For example, the addition or substitution of specific amino acid sequences may be introduced into an IL-10 sequence at the nucleic acid (DNA) level using site-directed mutagenesis methods employing synthetic oligonucleotides, which methods are also well known in the art.

In another embodiment, the polynucleotides encoding the variant IL-10 sequence can be made using standard techniques of molecular biology. For example, polynucleotide sequences coding for the above-described variant molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, Nature (1981) 292:756; Nambair et al., Science (1984) 223:1299; and Jay et al., J. Biol. Chem. (1984) 259:6311.

In one embodiment, the IL-10 variant molecule or fusion proteins thereof is a nucleic acid molecule encoding any of SEQ ID No: 9-29, 33-53, 55, 57, or 59. In another embodiment, the IL-10 variant molecule is DV05, DV06, or DV07 of SEQ ID No: 56, 58, or 60, respectively. The nucleic acid molecule encoding DV05, DV06, or DV07 may include insertions, deletions, or substitutions (e.g., degenerate code) that do not alter the functionality of the IL-10 variant molecule. The nucleotide sequences encoding the IL-10 variant and fusion proteins described herein may differ from the sequences of SEQ ID Nos: 1, 3, 5, 7, 9-29, 33-53, 55, 57, 59, 61, 63, 65, or 67 due to the degeneracy of the genetic code and may be 70-99%, preferably 70%, 75%, 80%, 85%, 90%, 95%, 96%, 97%, 98%, or 99%, homologous to the aforementioned sequences. Nucleotide sequence encoding the IL-10 variant and fusion proteins of SEQ ID Nos: 1, 3, 5, 7, 9-29, 33-53, 55, 57, 59, 61, 63, 65, or 67 may also be 70%-99%, preferably 70%, 75%, 80%, 85%, 90%, 95%, 96%, 97%, 98%, or 99%, homologous to due to the insertions, deletions, or substitutions of at least one nucleotide. Also envisaged in the present application are nucleotide sequences that have 70-99%, preferably 70%, 75%, 80%, 85%, 90%, 95%, 96%, 97%, 98%, or 99%, sequence homology to SEQ ID Nos: 2, 4, 6, 8, 56, 58, 60, 62, 64, 66, and 68, due to insertion, addition, deletion, or substitution of at least one nucleotide. Moreover, the nucleotide sequences encoding the IL-10 variant and fusion proteins described herein may further comprise well known sequences that aid in, for example, the expression, production, or secretion of the proteins. Such sequences may include, for example a leader sequence, signal peptide, and/or translation initiation sites/sequence (e.g. Kozak consensus sequence). The nucleotide sequences described herein may also include one of more restriction enzyme sites that allow for insertion into various expression systems/vectors.

In another embodiment, the polynucleotides are harbored in vectors comprising the desired IL-10 sequences or artificially synthesized using oligonucleotide synthesis techniques known in the art, such as site-directed mutagenesis and polymerase chain reaction (PCR) techniques. See, e.g., Sambrook, supra. In another embodiment, the nucleotide sequences encoding the variant IL-10 molecules are obtained through a process of annealing complementary overlapping synthetic oligonucleotides produced in an automated polynucleotide synthesizer, followed by ligation and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239:1534-1536), and enzymatic filling-in of gapped oligonucleotides using T4 DNA polymerase (Queen et al., Proc. Nat. Acad. Sci. USA (1989) 86:10029-10033) can be used to provide molecules for use in the subject methods.

A variety of suitable expression vectors may be used and are well known to a person skilled in the art, which can be used for expression and introduction of the variant IL-10 molecules and fusion proteins. These vectors include, for example, pUC-type vectors, pBR-type vectors, pBI-type vectors, pGA-type, pBinl9, pBI121, pGreen series, pCAMBRIA series, pPZP series, pPCV001, pGA482, pCLD04541, pBIBAC series, pYLTAC series, pSB11, pSB1, pGPTV series, and viral vectors and the like can be used.

The vectors harboring the IL-10 variant molecules may also include other vector componentry required for vector functionality. For example, the vector may include signal sequences, tag sequences, protease identification sequences, selection markers and other sequences regulatory sequences, such as promoters, required for proper replication and expression of the variant IL-10 molecules. The particular promoters utilized in the vector are not particularly limited as long as they can drive the expression of the variant IL-10 molecule in a variety of host cell types. Likewise, the type of Tag promoters are not be limited as long as the Tag sequence makes for simplier or easier purification of expressed variant IL-10 molecule easier. These might include, for example, 6-histidine, GST, MBP, HAT, HN, S, TF, Trx, Nus, biotin, FLAG, myc, RCFP, GFP and the like can be used. Protease recognition sequences are not particularly limited, for instance, recognition sequences such as Factor Xa, Thrombin, HRV, 3C protease can be used. Selected markers are not particularly limited as long as these can detect transformed rice plant cells, for example, neomycin-resistant genes, kanamycin-resistant genes, hygromycin-resistant genes and the like can be used.

The resulting DNA constructs carrying the desired IL-10 variants or fusion protein can then be used directly in gene therapy or can be used to produce recombinant IL-10 variant or fusion proteins. In one embodiment, the variant IL-10 molecules or fusion protein of the present application can be delivered by any method know in the art, including direct administration of the mutant IL-10 protein and gene therapy with a vector encoding the mutant IL-10 protein. Gene therapy may be accomplished using plasmid DNA or a viral vector, such as an adeno-associated virus vector, an adenovirus vector, a retroviral vector, etc. In some embodiments, the viral vectors of the application are administered as virus particles, and in others they are administered as plasmids (e.g. as "naked" DNA).

Other methods for the delivery of the nucleotide sequences include those which are already known in the art. These would include the delivery of the nucleotide sequences, such as but not limited to DNA, RNA, siRNA, mRNA, oligonucleotides, or variants thereof, encoding the IL-10 or IL-10 variant molecules by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer. The nucleotide sequences encoding IL-10 variant molecules may be delivered to a subject by direct injection, infusion, patches, bandages, mist or aerosol, or by thin film delivery. The nucleotide (or the protein) may be directed to any region that is desired for targeted delivery of a cytokine stimulus. These would include, for example, the lung, the GI tract, the skin, liver, brain though intracranial injection, deep seated metastatic tumor lesions via ultrasound guided injections.

Testing IL-10 Variants

In one embodiment, the variant IL-10 molecules or fusion proteins thereof will be screened for novel functions not previously generated using IL-10 homodimer sequences that suppress inflammatory cytokine secretion by macrophages but do not activate T cells. In one of the preferred embodiments, the variant IL-10 molecule or fusion proteins thereof will be based on an EBV-IL10 backbone that possess an anti-inflammatory response but lacks the ability to stimulate T-cells. These variant EBV-IL10 molecules or fusion proteins thereof will include modifications to the receptor binding domains and the previously unexplored linkage regions that alter the primary, secondary and tertiary structure to constrain or broaden the angle between the IL-10 homodimers. In another embodiment, IL-10 variant molecules comprising modifications to the linkage region or the regions responsible for inter-domain angle formation, will possess enhanced CD8+ T-cell function. In another embodiment, the IL-10 variant molecules or fusion proteins thereof comprising modifications to the linkage region or the regions responsible for inter-domain angle formation, will possess suppressed myeloid function but enhanced Kupffer cells function.

Once the variant IL-10 molecules or fusion proteins thereof are constructed and expressed, a person of skill in the art will be capable of performing screening assays on the IL-10 variant molecules or fusion proteins thereof to determine whether the molecules possess the desired biological functions imparted by the modifications to the IL-10 receptor binding regions and/or the inter-domain angle. A plurality of screening assays are known and available to those of skill in the art to test for the desired biological function. In one embodiment, the desired biological function includes, but are not limited to, reduced anti-inflammatory response, reduce T-cell stimulation, enhanced T-cell function, enhanced Kupffer cell functionality and reduced mast cell degranulation.

For example, it is known that IL-10 exposure primes T cells to generate and secrete more IFNγ upon T cell receptor stimulation. Simultaneously, IL-10 exposure prevents the secretion of TNFα, IL-6 and other pro-inflammatory cytokines secreted from monocytes/macrophages in response to LPS. IL-10 also suppresses $FoxP3^+CD4^+$ $T_{reg}$ proliferation. In one embodiment, those IL-10 variants molecules or fusion proteins thereof that maximize monocyte/macrophage suppression but lack T cell effects, including both stimulatory and suppressive responses, will be positively selected. In one embodiment, screening for IL-10 variant molecules or fusion proteins thereof that possess increased anti-inflammatory effects will be positively selected for the treatment of autoimmune, anti-inflammatory disease or both. In another embodiments, IL-10 variant molecules or fusion proteins thereof that enhance Kupffer cell scavenging and lack $T_{reg}$ suppression will also be selected to develop for treatment of Non-alcoholic Steatotic Hepatitis (NASH) and/or Non-alcoholic Fatty Liver Disease (NAFLD). In yet another embodiments, IL-10 variants that maximize T cell biology, including both stimulatory and suppressive responses, and also possesses enhanced Kupffer cell scavenging, will be selected to develop for the treatment of cancer.

The literature is replete with descriptions for assay the effect of cytokines on cells of the immune system, such as T cells, monocytes/macrophages, Kupffer cells, $T_{reg}$ cells, and mast cells, for example. The present application will apply these assay systems for testing the biological response employing similar assays by contacting the variant IL-10 molecules or fusion proteins thereof of the present application.

Various methods are described in the prior art for assaying the effectiveness of eliciting a T cell response. Any one of these methods are applicable for testing the variant IL-10 molecules described herein. For example, Chan et al. (2015) describes one such method that is applicable to the variant IL-10 molecules. $CD8^+$ T cells are isolated from peripheral blood mononuclear cells (PBMCs) using anti-CD8 microbeads. The isolated $CD8^+$ T cells are activated using anti-CD3 and anti-CD28 antibodies. For example, the activation may occur using plates coated with at least about 5 to 20 micro grams/mL of anti-CD3 antibody and at least about 1 to 5 micro grams/mL anti-CD28 antibody over a period of about 3 days. Following activation, the T cells are collected, plated, and treated with EBV-IL10 variants or fusion proteins thereof for a period of about 3-5 days. Commercially available PEGylated recombinant human IL-10 or EBV-IL10 may be used as a control. Following treatment with the EBV-IL10 variants, T cells were treated with soluble anti-CD3. Following treatment with anti-CD3, the cell culture media is collected and assayed by ELISA for secretion of interferon gamma (IFNγ).

Various methods are described in the prior art for assaying monocytes/macrophages stimulation by cytokines. Any one of these methods are applicable for testing the variant IL-10 molecules described herein. For example, Conway et al (2017) describes one such method that is applicable to the variant IL-10 molecules. Human monocytes are isolated from buffy coats of fresh donor blood using a Ficoll gradient, followed by hypertonic density centrifugation in Percoll. After 30-min cultivation in RPMI supplemented with 5% human serum and 1% L-glutamine, the monocytes became adherent and are washed with SMEM Spinner medium to remove contaminating lymphocytes. Solutions and materials were tested to ensure the absence of LPS. After 4 days of cultivation, the monocytes/macrophages are contacted or incubated with 10 ng/ml LPS and different concentrations of variant IL-10 molecules for a period of at least 24 h. Culture supernatants are harvested, and TNF-α, and IL-1β concentrations are determined by ELISA.

Various methods are described in the prior art for assaying Kupffer cell response to cytokines. Any one of these methods are applicable for testing the variant IL-10 molecules described herein. For example, Chan et al (2016) describes one such method that is applicable to the variant IL-10 molecules. Kupffer cells are plated in 24-well or 96-well plates and incubated overnight in hepatocyte incubation medium (phenol-red free RPMI, pen/strep, Cell Maintenance Supplement B (Invitrogen)). Cells were washed and exposed for 24 hours to variant IL-10 molecules. Cells are washed once and exposed to 15-20 μl DiI-LDL, DiI-VLDL, DiI-OxLDL or DiI-AcLDL, 2 μl DMSO, 15 μl Cytochalasin D, where uptake is measured after 4 hours. All cells are washed once in 1×PBS and lysed with 110 μl cell lysis buffer. 45 μl of cell lysate is transferred to clear bottom black walled plates where fluorescence is read at 575 nm.

Various methods are described in the prior art for assaying the effectiveness of stimulating T regulatory cell response using cytokines. Any one of these methods are applicable for testing the variant 1-10 molecules described herein. For example, Chan et al (2016) describes one such method that is applicable to the variant IL-10 molecules. $CD4^+$ T cells are isolated with $CD4^+$ microbeads and cultured for 5-6 days in AIMV media containing various concentrations of the variant IL-10 molecule and 2 micrograms/mL immobilized anti-CD3 and 1 mg/mL anti-CD28. Cells are analyzed for FoxP3 expression by flow cytometric analysis to determine if TGF-β or IL-2 is induced in the FOX $P3^+$ $CD4^+$ T regulatory cells.

Various methods are described in the prior art for assaying the effectiveness of proliferating mast cells in response to cytokine stimulation. The murine mast cell line MC/9 is a common cell line use for manufacturing release testing of IL-10 molecules. Specifically, IL-10 and IL-10 variant molecules induce dose titratable proliferation of mast cells. Conversely, IL-10 inhibits Fc expression by mast cells, suggesting IL-10 exerts both stimulatory and suppressive effects on these cells. Any one of these methods are applicable for testing the variant IL-10 molecules described herein. For example, Thompson-Snipes et al (1991) describes one such method that is applicable to the variant IL-10 molecules. MC/9 mast cells are plated in flat-bottomed 24-well plates containing 1 ml of RPMI 1640, 10% FCS, 50 mM 2-ME, and varying concentrations of variant cytokines. After culturing for 3 days, cell are counted using a cell counter to determine the impact of the variant IL-10 molecules on mast cell proliferation.

It is known that IL-10 plays a role in inhibiting mast cell expression of the IgE receptor, FcεRI, and IgE-mediated cytokine production. Thus, methods have been described in the prior art for testing IL-10's impact on mast cells. These methods are applicable for testing the IL-10 variant molecules described herein. For example, Kennedy Norton et al (2008) describes one such method. Human mast cells were isolated from donor skin samples and cultured in medium containing stem cell factor (SCF) in the presence or absence of IL-10. FcεRI expression was determined by flow cytometry using of anti-FcεRI specific antibodies followed by FITC-labeled anti-mouse $F(ab')_2$.

Compositions and Formulations Comprising IL-10 Variant Molecules

The IL-10 variant molecules or fusion proteins thereof of the present application may also be formulated in a pharmaceutical composition comprising a therapeutically effective amount of the variant IL-10 molecule and a pharmaceutical carrier and/or pharmaceutically acceptable excipients. The pharmaceutical composition may be formulated with commonly used buffers, excipients, preservatives, stabilizers, The pharmaceutical composition will be formulated for administration to a patient in a therapeutically effective amount sufficient to provide the desired therapeutic result. Preferably, such amount has minimal negative side effects. In one embodiment, the amount of variant IL-10 molecule or fusion protein thereof administered will be sufficient to treat inflammatory diseases or condition. In another embodiment, the amount of variant IL-10 molecule or fusion proteins thereof administered will be sufficient to treat cancer. The amount administered may vary from patient to patient and will need to be determined by considering the subject's or patient's disease or condition, the overall health of the patient, method of administration, the severity of side-effects, and the like. In a preferred embodiment, the pharmaceutical composition will include a variant IL-10 molecule or fusion protein thereof that includes one or both of a modification to the receptor binding domain and/or the inter-domain angle of the IL-10. In another embodiment, the variant IL-10 molecule is a PEGylated form of the variant IL-10 molecule. In yet a more preferred embodiment, the pharmaceutical composition comprises the variant IL-10 molecule incorporated as a fusion protein or immunocytokine and pharmaceutical excipients.

An effective amount for a particular patient may vary depending on factors such as the condition being treated, the overall health of the patient, the method route and dose of administration and the severity of side effects. The appropriate dose administered to a patient is typically determined by a clinician using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

The dose administered to the patient may also be optimized based on the addition of certain serum half-life extension modifications to the IL-10 or variant IL-10 molecule (see, e.g., pegylated IL-10, discussed in detail, for example, in U.S. Pat. Nos. 9,943,568, 10,010,588, and 10,143,726, has been known to improve circulation half-life of IL-10). The fusion protein, immunoconjugates, fusion protein, minobodies, and diabodies comprising IL-10 or variant IL-10, disclosed herein, are also able to extend circulation half-life, while simultaneously retaining high affinity binding to the IL-10 receptor. Thus, in one embodiment, various diseases, disorders, or conditions associated with IL-10 or that may be improved by administering a fusion protein, a complex of fusion proteins, immunoconjugate, or a diabody comprising IL-10 or a variant IL-10, may be administered to a patient in need thereof. In one preferred embodiment, diseases, disorders, or conditions associated with IL-10 may be treated or prevented by administering to a patient in need thereof a therapeutically effective amount of an immunoconjugate complex, fusion protein, or diabody with an EBV IL-10 or a variant thereof (including a variant impacting IL-10 receptor biding affinity), wherein the immunoconjugate complex, fusion protein, or diabody has a molecular weight of about 60 to 155 kDa, wherein the therapeutically effective amount is in the range of about 0.5 microgram/kilogram to 100 micrograms/kilogram. The immunoconjugate, fusion protein, or diabody described herein may be administered daily, three times a week, twice a week, weekly, bimonthly, or monthly. The EBV IL-10 portion and the variable regions of the immunoconjugate, fusion protein, or diabody may be any configuration or combination of those structures discussed herein. The half-life extended molecules described herein will be effective in treating a variety of diseases including, but not limited to, cancer, inflammatory diseases, autoimmune diseases (e.g., nonalcoholic steatohepatitis (NASH) or nonalcoholic fatty liver disease (NAFLD)), and elevated cholesterol.

Methods for co-administration or treatment with a second therapeutic agent, e.g., a cytokine, steroid, chemotherapeutic agent, antibiotic, anti-inflammatory agents, or radiation, are well known in the art. These might include combination treatments with other therapeutic agents, such as but not limited to one or more the following: interferon-β, for example, IFNβ-1α and IFN-β-1β; a protein that simulates myelin basic protein; corticosteroids; IL-1 inhibitors; TNF inhibitors; anti-TNFα antibodies, anti-IL-6 antibodies, IL-1br-Ig fusion, anti-IL-23 antibodies, antibodies to CD40 ligand and CD80; antagonists of IL-12 and IL-23, e.g., antagonists of a p40 subunit of IL-12 and IL-23 (e.g., inhibitory antibodies against the p40 subunit); IL-22 antagonists; small molecule inhibitors, e.g., methotrexate, leflunomide, sirolimus (rapamycin) and analogs thereof, e.g., CCI-779; Cox-2 and cPLA2 inhibitors; NSAIDs; p38 inhibitors; TPL-2; Mk-2; NFkβ inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkβ antagonists.

Additionally, the combination treatment useful for administration with the IL-10 variant molecules or fusion proteins thereof may include TNF inhibitors include, e.g., chimeric, humanized, effectively human, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; and TNF enzyme antagonists, e.g., TNFα converting enzyme (TACE) inhibitors. Other combination treatment with anti-inflammatory agents/drugs that includes, but not limited to standard non-steroidal anti-inflammatory drugs (NSAIDs) and cyclo-oxygenase-2 inhibitors. NSAID may include aspirin, celecoxib, diclofenac, diflunisal, etodolac, ibuprofen, indomethacin, ketoprofen, ketorolac, nabumetone, naproxen, oxaprozin, piroxicam, salsalate, sulindac, and/or tolmetin. The cyclo-oxygenase-2 inhibitor employed in compositions according to the application could, for example, be celecoxib or rofecoxib.

Additional therapeutic agents that can be co-administered and/or co-formulated with IL-10 variant molecules or fusion proteins thereof include one or more of: interferon-β, for example, IFN β-1α and IFN β-1β; COPAXONE®; corticosteroids; IL-1 inhibitors; TNF antagonists (e.g., a soluble fragment of a TNF receptor, e.g., p55 or p75 human TNF receptor or derivatives thereof, e.g., 75 kdTNFR-IgG; antibodies to CD40 ligand and CD80; and antagonists of IL-12 and/or IL-23, e.g., antagonists of a p40 subunit of IL-12 and IL-23 (e.g., inhibitory antibodies that bind to the p40 subunit of IL-12 and IL-23); methotrexate, leflunomide, and a sirolimus (rapamycin) or an analog thereof, e.g., CCI-779. Other therapeutic agents may include Imfimzi or Atezolizumb.

For purposes of treating NASH, for example, the IL-10 variant molecules or fusion proteins thereof may be combined with cholesterol lowering agents, such as statins and non-statin drugs. These agents include, but are not limited to simvastatin, atorvastatin, rosuvastatin, lovastatin, pravastatin, gemfibrozil, fluvastatin, cholestyramine, fenofibrate, cholesterol absorption inhibitors, bile acid-binding resins or sequestrants, and/or microsomal triglyceride transfer protein (MTP) inhibitors.

An effective amount of therapeutic will impact the level of inflammation or disease or condition by relieving the symptom. For example, the impact might include a level of impact that is at least 10%; at least 20%; at least about 30%; at least 40%; at least 50%; or more such that the disease or condition is alleviated or fully treated.

The pharmaceutical compositions comprising variant IL-10 molecule or fusion proteins thereof is mixed with a pharmaceutically acceptable carrier or excipient. Various pharmaceutical carriers are known in the art and may be used in the pharmaceutical composition. For example, the carrier can be any compatible, non-toxic substance suitable for delivering the variant IL-10 molecule compositions of the application to a patient. Examples of suitable carriers include normal saline, Ringer's solution, dextrose solution, and Hank's solution. Carriers may also include any poloxamers generally known to those of skill in the art, including, but not limited to, those having molecular weights of 2900 (L64), 3400 (P65), 4200 (P84), 4600 (P85), 11,400 (F88), 4950 (P103), 5900 (P104), 6500 (P105), 14,600 (F108), 5750 (P123), and 12,600 (F127). Carriers may also include emulsifiers, including, but not limited to, polysorbate 20, polysorbate 40, polysorbate 60, and polysorbate 80, to name a few. Non-aqueous carriers such as fixed oils and ethyl oleate may also be used. The carrier may also include additives such as substances that enhance isotonicity and chemical stability, e.g., buffers and preservatives, see, e.g., Remington's Pharmaceutical Sciences and U.S. Pharmacopeia: National Formulary, Mack Publishing Company, Easton, Pa. (1984). Formulations of therapeutic and diagnostic agents may be prepared by mixing with physiologically acceptable carriers, excipients, or stabilizers in the form of lyophilized powders, slurries, aqueous solutions or suspensions, for example.

Compositions of the application can be administered orally or injected into the body. Formulations for oral use can also include compounds to further protect the variant IL-10 molecules from proteases in the gastrointestinal tract. Injections are usually intramuscular, subcutaneous, intradermal or intravenous. Alternatively, intra-articular injection or other routes could be used in appropriate circumstances. Parenterally administered variant IL-10 molecules are preferably formulated in a unit dosage injectable form (solution, suspension, emulsion) in association with a pharmaceutical carrier and/or pharmaceutically acceptable excipients. In other embodiments, compositions of the application may be introduced into a patient's body by implantable or injectable drug delivery system.

Therapeutic Uses of IL-10 Variants

In one embodiment, the present application provides methods of treating, alleviating, or reducing symptoms associated with inflammation, inflammatory disease, or autoimmune disease. The present application also provides for IL-10, IL-10 variant molecules, fusion proteins or chimeric molecules thereof, for use as a medicament for inflammation, inflammatory disease, or autoimmune disease, cancer, or oncology. The present application also contemplates the use of IL-10, IL-10 variant molecules, fusion proteins or chimeric molecules thereof for use in the treatment of inflammation or inflammatory disease, or autoimmune disease, cancer, or oncology. These would include, for example, IBD, Crohn's disease, ulcerative colitis, NASH, NAFLD, hypercholesterolemia, or cancer to name a few. The method contemplates administering a therapeutically effective amount of one or more of the variant IL-10 molecule or fusion proteins thereof described herein. In one embodiment, the application includes a method of treating inflammatory diseases or autoimmune diseases comprising administering a therapeutically effective amount of a variant IL-10 molecule comprising one or more modification associated with the receptor binding domain and/or the region responsible for forming the inter-domain angle. In one preferred embodiment, the method includes administering a variant EBV-IL10 molecule or fusion proteins thereof. In one preferred embodiment, the variant IL-10 molecules or fusion proteins thereof useful for treating inflammatory disease includes variant molecules that have constrained inter-domain angles, as compared to the wild-type IL-10 molecules and/or also exhibit lower receptor affinity. In other embodiments, the variant IL-10 molecules or fusion proteins thereof useful for treating inflammatory disease includes variant molecules that have relaxed inter-domain angles, as compared to the wild-type IL-10 molecules and/or also exhibit lower receptor affinity. PEGylated forms of the variant IL-10 molecules are also envisioned as part of the present application for inflammatory disease or inflammation.

The inflammatory diseases or autoimmune diseases of the present application include any disease or condition associated with unwanted or undesirable inflammation and immune reaction. These diseases include, but are not limited to, inflammatory bowel disease (IBD), Crohn's disease, psoriasis, rheumatoid arthritis, Non-Alcoholic Fatty Liver Disease (NAFLD) or Nonalcoholic steatohepatitis (NASH).

In other embodiments, the diseases or conditions include neurodegenerative disorders such as Parkinson's disease, amyelotrophic lateral sclerosis (ALS), fatal familial insomnia, Rasmussen's encephalitis, Down's syndrome, Huntington's disease, Gerstmann-Straussler-Scheinker disease, tuberous sclerosis, neuronal ceroid lipofuscinosis, subacute sclerosing panencephalitis, Lyme disease; tse tse's disease (African Sleeping Sickness), HIV dementia, bovine spongiform encephalopathy ("mad cow" disease); Creutzfeldt Jacob disease; Herpes simplex encephalitis, Herpes Zoster cerebellitis, general paresis (syphilis), tuberculous meningitis, tuberculous encephalitis, optic neuritis, granulomatous angiitis, temporal arthritis, cerebral vasculitis, Spatz-Lindenberg's disease, methamphetamine-associated vasculitis, cocaine-associated vasculitis, traumatic brain injury, stroke, Lance-Adams syndrome, post-anoxic encephalopathy, radiation necrosis, limbic encephalitis, Alzheimer's disease, progressive supranuclear palsy, striatonigral degeneration, corticocobasal ganglionic degeneration, primary progressive aphasia, frontotemporal dementia associated with chromosome 17, spinal muscular atrophy, HIV-associated myelopathy, HTLV-1-associated myelopathy (Tropical Spastic Paraparesis), tabes dorsalis (syphilis), transverse myelitis, post-polio syndrome, spinal cord injury, radiation myelopathy, Charcot-Marie-Tooth, HIV-associated polyneuropathies, campylobacter-associated motor axonopathies, chronic inflammatory demyelinating polyneuropathy, diabetic amyotrophy avulsion, phantom limb, complex regional pain syndrome, diabetic neuropathies, paraneoplastic neuropathies, myotonic dystrophy, HTLV-1-associated myopathy, trichinosis, inflammatory myopathies (polymyositis, inclusion body myositis, dermatomyositis), sickle cell disease, alpha-1-antitrypsin deficiency, tuberculosis, subacute bacterial endocarditis, chronic viral hepatitis, viral cardiomyopathy, Chaga's disease, malaria, Coxsackie B infection, macular degeneration, retinitis pigmentosa, vasculitis, inflammatory bowel disease, rheumatoid arthritis, bullous pemphigus, Churg-Strauss syndrome, myocardial infarction, toxic epidermal necrolysis, shock (e.g., acute anaphylactic shock), type-1 diabetes, autoimmune thyroiditis, lymphoma, ovarian cancer, Lupus (systemic lupus erythematosus), asthma, progeria, sarcoidosis, type-2 diabetes and metabolic syndrome. Other diseases or conditions associated with inflammation, which are embodiments of the application, include inflammatory lung disorders such as bronchitis, oxidant-induced lung injury and chronic obstructive airway disease; inflammatory disorders of the eye including corneal dystrophy, ocular hypertension, trachoma, onchocerciasis, retinitis, uveitis, sympathetic ophthalmitis and endophthalmitis; chronic inflammatory disorders of the gum including periodontitis; chronic inflammatory disorders of the joints including arthritis, septic arthritis and osteoarthritis, tuberculosis arthritis, leprosy arthritis, sarcoid arthritis; disorders of the skin including sclerodermatitis, sunburn, psoriasis and eczema; encephalomyelitis and viral or autoimmune encephalitis; autoimmune diseases including immune-complex vasculitis, and disease of the heart including ischemic heart disease, heart failure and cardiomyopathy. Other non-limiting examples of diseases that may benefit from variant IL-10 molecules or fusion proteins thereof include adrenal insufficiency; hypercholesterolemia; atherosclerosis; bone disease associated with increased bone resorption, e.g., osteoporosis, pre-eclampsia, eclampsia, uremic complications; chronic liver failure, and other disorders associated with inflammation such as cystic fibrosis, tuberculosis, cachexia, ischemia/reperfusion, hemodialysis related conditions, glomerulonephritis, restenosis, inflammatory sequelae of viral infections, hypoxia, hyperbaric oxygen convulsions and toxicity, dementia, Sydenham's chorea, Huntington's disease, epilepsy, Korsakoff's disease, imbecility related to cerebral vessel disorder, NO mediated cerebral trauma and related sequelae, ischemic brain edema (stroke), migraine, emesis, immune complex disease, allograft rejection, infections caused by invasive microorganisms; and aging.

Figure 8A:
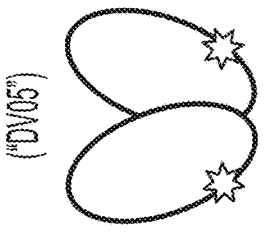
FIGS. 8A-8C are schematic representations of various IL-10 variants, such as variants made in EBV IL-10.
Figure 8B:
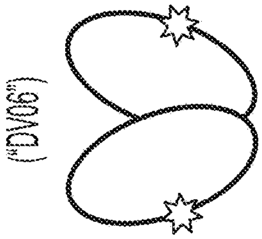
Figure 8C:
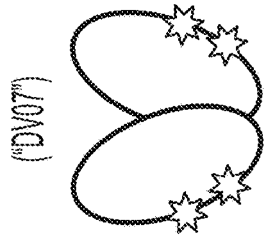
Figure 8D:
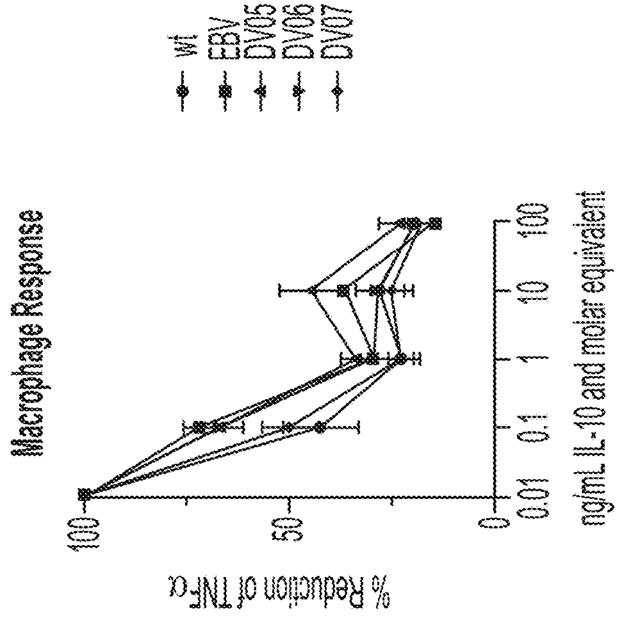
FIG. 8D assays monocytes/macrophage response to various forms of IL-10, including wild type human IL-10, EBV-IL-10, DV05, DV06, and DV07. All forms, including the IL-10 variants—DV05, DV06, DV07—suppress TNFα secretion in response to LPS.
Figure 8E:
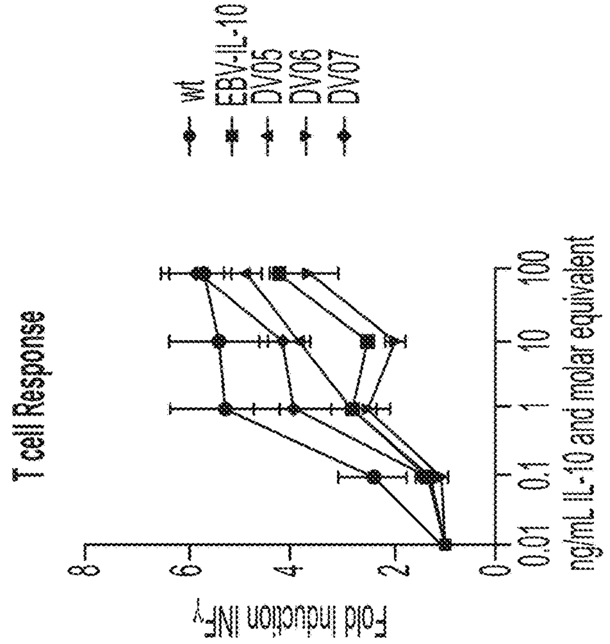
FIG. 8E assays T-cell response to various forms of IL-10—wild type human IL-10, EBV IL-10, DV05, DV06, and DV07—and not all forms induce IFN-gamma.

An IL-10 variant or fusion protein thereof most effective for treating anti-inflammatory diseases or conditions include those having the lowered capacity of stimulating T-cells. Thus, modifying the receptor binding domain through an amino acid substitutions at position 75 has been shown by the inventor of the present application to induce the least amount of T cell stimulation. In particular, EBV IL-10 harboring a A75I substitution in SEQ ID No.: 3 (or SEQ ID No. 57) has been shown to decrease T-cell stimulation (see, e.g., FIG. 8E, denoted as DV06). Thus one particularly preferred embodiment contemplates the use of diabodies and monobodies with IL-10 variant molecules harboring a DV06 based mutation (substitution at amino acid position 75 of SEQ ID No.: 3, or SEQ ID No. 57). In a more preferred embodiment, methods of inflammatory disease will utilize a fusion protein or fusion protein complex comprising SEQ ID Nos: 26-27; 37; 40; 41-42, 43, 48-49 or a combination thereof.

Figure 16C:
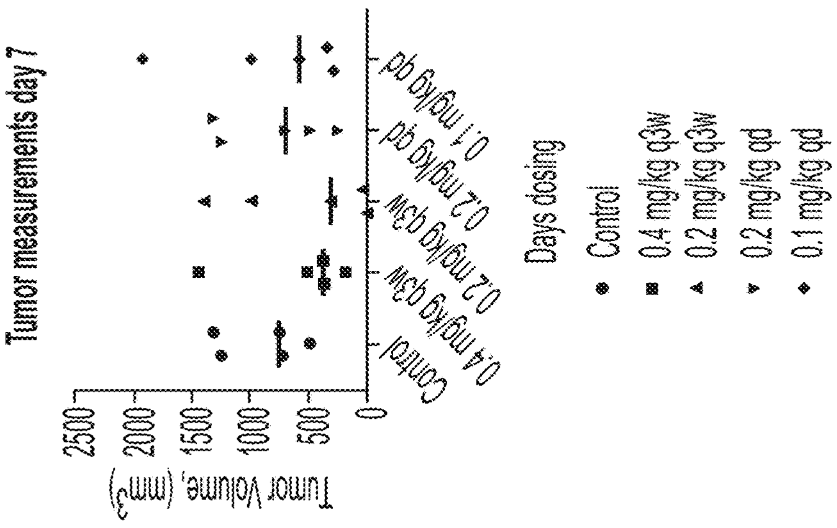
FIGS. 16A-16C are results from an in vivo tumor study using D:DV07 (with V31L and A75I mutations comprising variable regions from anti-CD3t and anti-EGFR). In vivo tumor volume were assessed following the administration of a dosing formulation buffer ("control"), 0.4 mg/kg three times a week (q3w), 0.2 mg/kg three times a week (q3w), 0.2 mg/kg two days off (qd), 0.1 mg/kg two days off (qd).
Figure 16B:
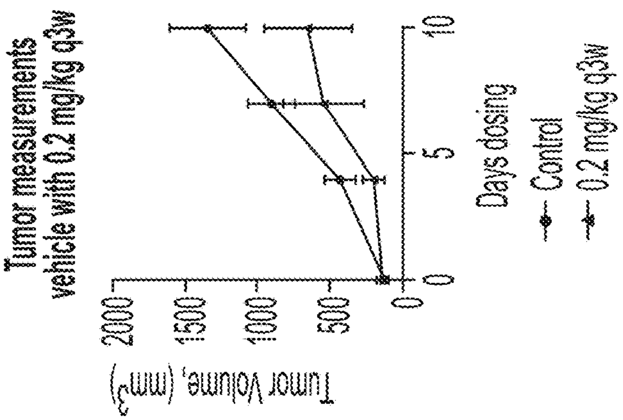
Figure 16A:
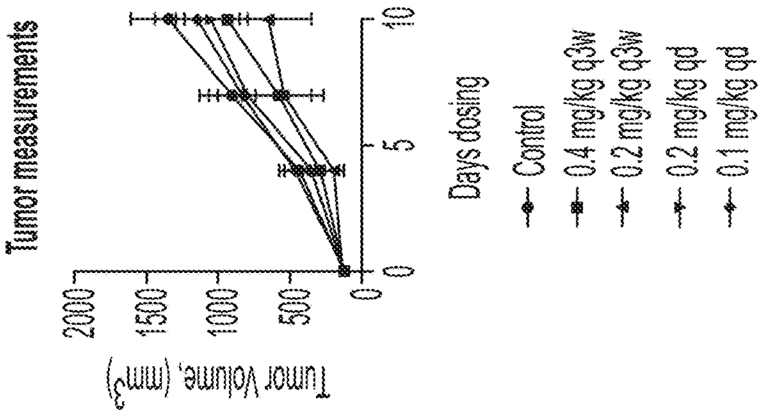

In another embodiment of the application, the method of treating includes administering the IL-10 or variant IL-10 molecule or fusion proteins thereof to treat or reduce symptoms associated with cancer. The method contemplates administering a therapeutically effective amount of one or more of the IL-10 or variant IL-10 molecule or fusion proteins thereof described herein. In one embodiment, the application includes a method of treating or reducing symptoms associated with cancer comprising administering a therapeutically effective amount of a variant IL-10 molecule comprising one or more modification associated with the receptor binding domain and/or the region responsible for forming the inter-domain angle. In one preferred embodiment, the method includes administering a variant EBV-IL10 molecule or fusion proteins thereof. The variant IL-10 molecules or fusion proteins thereof useful for treating cancer include variant molecules that have constrained inter-domain angles, as compared to the wild-type IL-10 molecules and/or also exhibit higher receptor affinity. The variant IL-10 molecules or fusion proteins thereof useful for treating or reducing symptoms associated with cancer include variant molecules that have relaxed inter-domain angles, as compared to the wild-type IL-10 molecules and/or also exhibit higher receptor affinity. PEGylated forms of the variant IL-10 molecules are also envisioned as part of the present application for treating cancer. One particular example of a fusion protein capable of reducing in vivo tumor volume includes an IL-10 variant harboring two substitutions at amino acid positions 31 and 75 of SEQ ID No.: 3, which includes specific substitutions of V31L and A75I, termed DV07 (e.g., SEQ ID No.:59). FIGS. 16A-C demonstrates that at varying doses, a fusion protein comprising the DV07 EBV IL-10 molecule conjugated on a diabody structure, termed D:DV07, reduced tumor volume over a time course of 7 and 10 days. Thus one particularly preferred embodiment contemplates the use of diabodies and monobodies with IL-10 variant molecules harboring a DV07 based mutation (substitutions at amino acid positions 31 and 75 of SEQ ID No.: 3; or SEQ ID No: 59). In a more preferred embodiment, methods of treating cancer or oncology or tumors will utilize a fusion protein or fusion protein complex comprising SEQ ID Nos: 28-29; 33; 34; 35-36; 38-39; 46-47, 61, 63, 65, or 67; or a combination thereof.

Cancer or proliferative disorder treatable by the variant IL-10 molecules or fusion proteins thereof described herein include various forms of cancer, including but not limited to, cancer of the uterus, cervix, breast, prostate, testes, penis, gastrointestinal tract, e.g., esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, e.g. gliomas, ganglia, central nervous system (CNS) and peripheral nervous system (PNS), and immune system, e.g., spleen or thymus. The present application provides methods of treating, e.g., immunogenic tumors, non-immunogenic tumors, dormant tumors, virus-induced cancers, e.g., epithelial cell cancers, endothelial cell cancers, squamous cell carcinomas, papillomavirus, adenocarcinomas, lymphomas, carcinomas, melanomas, leukemias, myelomas, sarcomas, teratocarcinomas, chemically-induced cancers, metastasis, and angiogenesis. The application also contemplates reducing tolerance to a tumor cell or cancer cell antigen, e.g., by modulating activity of a regulatory T cell ($T_{reg}$) and or a $CD8^+$ T cell. In a preferred embodiment, the IL-10 variant molecules are particularly useful in treating patients or subjects with liver metastatic disease.

In yet other embodiments, the methods of treating or reducing symptoms associated with inflammatory disease or cancer include administering variant IL-10 molecules or fusion proteins thereof or derivatized forms thereof (e.g., PEGylation) in combination with other therapeutic agents. These therapeutic agents include, without limitation, cytokine or cytokine antagonist, such as IL-12, IL-2, IL-15, interferon-alpha, or anti-epidermal growth factor receptor, doxorubicin, epirubicin, an anti-folate, e.g., methotrexate or fluoruracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, *vinca* alkaloid, taxane, e.g., paclitaxel and docetaxel, a cell cycle inhibitor, e.g., a cyclin-dependent kinase inhibitor, a monoclonal antibody against another tumor antigen, a complex of monoclonal antibody and toxin, a T cell adjuvant, bone marrow transplant, or antigen presenting cells, e.g., dendritic cell therapy.

In other embodiments, the present application also embodies methods of treating lipid-related disorders, such as hypercholesterolemia and hypertriglyceridemia, and/or improving lipid parameters such as total cholesterol, high density lipoprotein (HDL) cholesterol, low density lipoprotein (LDL) cholesterol, very low density lipoprotein (VLDL) cholesterol, triglycerides, and non-HDL cholesterol, comprising administering the variant IL-10 molecules or derivatized form thereof (e.g., PEGylation).

An IL-10 variant or fusion protein thereof most effective for treating lipid-related diseases or disorders include those having the least suppressive capacity on macrophages. Thus, modifying the receptor binding domain through an amino acid substitutions at position 31 (coupled with an increased inter-domain angle of the homodimer) has been shown by the inventor of the present application to induce the least amount of macrophage response. In particular, EBV IL-10 harboring a V31L substitution in SEQ ID No.: 3 has been shown to decrease macrophage response (see, e.g., FIG. 8A, denoted as DV05, or SEQ ID No. 55). Thus one particularly preferred embodiment contemplates the use of diabodies and monobodies with IL-10 variant molecules harboring a DV05 based mutation (substitution at amino acid positions 31 SEQ ID No.: 3, or SEQ ID No. 55). In a more preferred embodiment, methods of treating lipid based diseases or disorders will utilize a fusion protein or fusion protein complex comprising SEQ ID Nos: 24-25; 50-51; or 45.

In yet another embodiment of the application, the IL-10 variant molecules or fusion proteins thereof, viral IL-10 (including EBV or CMV IL-10), or wild-type IL-10, any of which may optionally include a PEGylation or HESylation, is used in a method of targeting mast cells, by reducing mast cell degranulation. In a preferred embodiment, the method of targeting mast cells comprise contacting viral IL-10 or IL-10 variant molecules to treat seasonal allergies or acute anaphylactic response. In another aspect, the IL-10 variant molecules, viral IL-10 (including EBV or CMV IL-10), or wild-type IL-10 is used in a method to reduce IgE responsiveness.

In yet another embodiment, the IL-10 variant molecules or fusion proteins thereof of the present application are preferably useful in the described methods (e.g., anti-inflammatory and/or cancer) when the patient population is screened. In one embodiment, those patients that exhibit a profile wherein there is an elevated or high IFNγ response are most susceptible or ideal for use of the IL-10 variant molecules to treat cancer. In another embodiment, those patients that exhibit a profile wherein there is a decreased or low IFNγ response are most susceptible or ideal for use of the IL-10 variant molecules to treat anti-inflammation.

The broad scope of this application is best understood with reference to the following examples, which are not intended to limit the application to any specific embodiments. All citations herein are incorporated herein by reference to the same extent as if each individual publication or patent application was specifically and individually indicated to be incorporated by reference.

Many modifications and variations of this application can be made without departing from its spirit and scope, as will be apparent to those skilled in the art. The specific embodiments described herein are offered by way of example, and the application is to be limited by the terms of the appended claims, along with the full scope of equivalents to which such claims are entitled; and the application is not to be limited by the specific embodiments that have been presented herein by way of example. Further, all references, patents and patent applications cited in the foregoing specification are incorporated herein by reference.

EXAMPLES

The following examples are merely illustrative of the various embodiments of the application and should not be construed in any manner to limit the scope of the application.

Example 1

EBV-IL-10 variants or fusion proteins thereof are constructed by alteration of the primary sequence through standard molecule biology cloning techniques. The alterations in the primary sequence are designed to alter the affinity of the receptor binding domains as well as open or close the interdomain angles. The receptor affinity can be altered by changing amino acids at and around positions 31 and/or 75 in the mature secreted sequence. The interdomain angles can be altered, for instance, but not limited to, introducing a proline in the non-alpha helical sequences between helix C and D, and D and E. Prolines drive a kink in the linear direction of a primary amino acid sequence potentially altering subsequent interdomain angles driven by the secondary and tertiary structures of the D and E helix. Similarly, introduction of amino acids with bulky side chains such as tryptophan, can introduce less significant alterations to the linear structure of primary amino acid backbones, resulting in less profound changes to secondary and tertiary structures.

Example 2

The following examples provides a description of how variant IL-10 molecules or fusion proteins thereof are assessed in macrophages.

Human blood from healthy patient populations or from patients suffering from an inflammatory disease (e.g., Crohn's disease) are drawn and freshly drawn Buffy Coats are processed to harvest PBMCs using standard Ficoll density gradient centrifugation procedures. PBMCs are then subjected to enrichment for $CD14^+$ monocytes cells using EasySep™ Human Monocyte Enrichment Kit (Cat #19059, Stem Cell Technologies) and following manufacturer's instructions. The enrichment efficiency are assessed by standard flow cytometry.

The enriched monocytes are plated in 24-well plates at $2\times10^6$ cells/mL/well in RPMI medium supplemented with 5% human serum and PSG. The cells are treated with serial dilutions (0, 0.1, 1, 10, 100, 1000 ng/mL) of the variant IL-10 molecule for 1 hour at 37° C./5% CO2 humidified incubator and then exposed to 10 ng/mL LPS (Cat #L4391, Sigma-Aldrich) for 12-16 hours. Following an overnight incubation, supernatants are harvested and inflammatory cytokines (IL-6, TNFα, IL-1β) are measured by either standard ELISA or using iQue Screener (Intellicyt).

In the study, the above described procedure are used to compare the impacts of non-PEGylated EBV-IL10 and non-PEGylated human IL-10 on the immune suppressive capabilities on macrophages. FIGS. 2A, 2B and 3A, 3B show that the EBV-IL10 retained the ability to suppress inflammatory cytokines IL-1β and TNFα, which indicates that despite having differences in inter-domain angle, the EBV-IL10 is capable of maintaining its suppressive inflammatory capabilities in a manner similar to human IL-10.

Example 3

The following examples provides a description of how variant IL-10 molecules or fusion proteins thereof are assessed in human $CD8^+$ T-cells.

Human blood from healthy patient populations or from patients suffering from a inflammatory disease (e.g., Crohn's disease) are drawn and freshly drawn Buffy are processed to harvest PBMCs using standard Ficoll density gradient centrifugation procedures. The PBMCs are then subjected to enrichment for CD8; T cells using EasySep™ Human $CD8^+$ T Cell Enrichment Kit (Cat #19053, Stem Cell Technologies) following manufacturer's instructions. The enrichment efficiency are assessed by standard flow cytometry methods. Enriched cells are suspended in AIMV (Thermo Fisher Scientific, Cat #12055083) culture medium. Twenty-four-well plates are coated with 10 micrograms/mL of anti-CD3 (Cat #16-0039-85, Thermo Fisher Scientific) and 2 micrograms/mL of anti-CD28 (Cat #16-0289-85, Thermo Fisher Scientific) for 2 hours by incubating at 37° C./5%002 humidified cell culture incubator followed by 1-2 washes with 1×PBS.

The enriched $CD8^+$ T cells (3×10/mL/well) are added to the anti-CD3/anti-CD28 coated plates and incubated for 72 hours at 37° C./5% CO2 humidified cell culture incubator.

After 72 hours, the cells are harvested, counted and 100 μl replated in round-bottom 96-well plate (2×105 cells/well) in the presence/absence of serial dilutions (0, 0.1, 1, 10, 100, 1000 ng/mL—added at 100 μL/well) of the variant IL-10 molecules or a control sample. The testing is run in triplicate. The cells with the variant IL-10 molecules or fusion proteins thereof are incubated for 72 hours at 37° C./5% CO2 humidified incubator. After 72 hours, the cells are collected, washed, replated in a fresh round-bottom 96 well-plate in the presence of soluble ant-CD3 (Cat #16-0039-85, Thermo Fisher Scientific) for 4 hours at 37° C./5% CO2 humidified incubator.

Figure 2C:
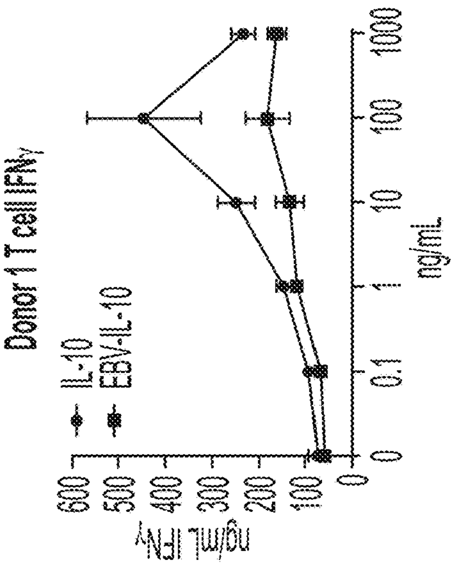
FIGS. 2A-2C compare the ability of IL-10 and EBV IL-10 to activate monocytes/macrophages (Mθ) by examining IL-1β (FIG. 2A) and TNFα (FIG. 2B) cytokine production and the stimulation of T-cells by examining IFNγ (FIG. 2C) production in Donor 1.
Figure 2B:
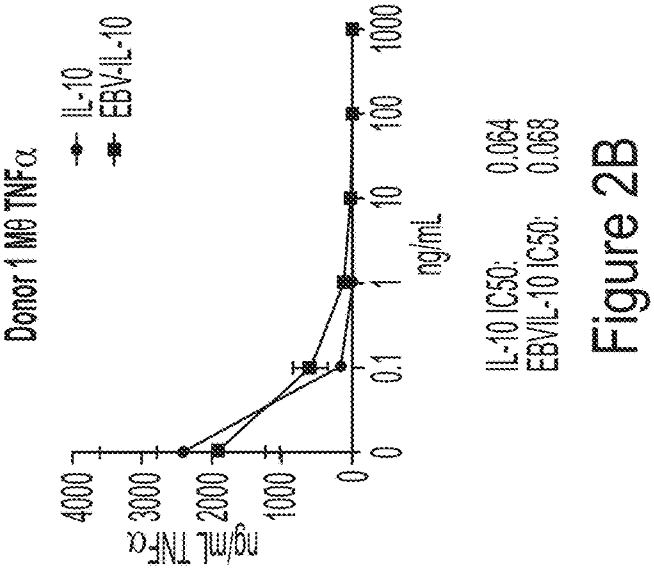
Figure 2A:
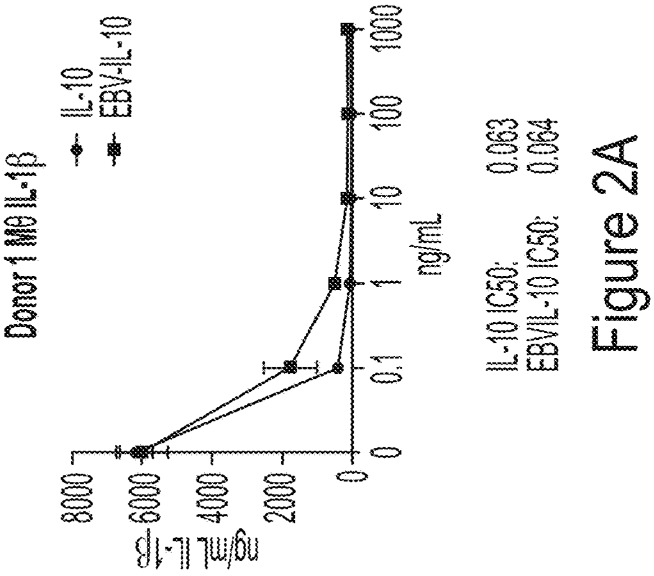
Figure 3C:
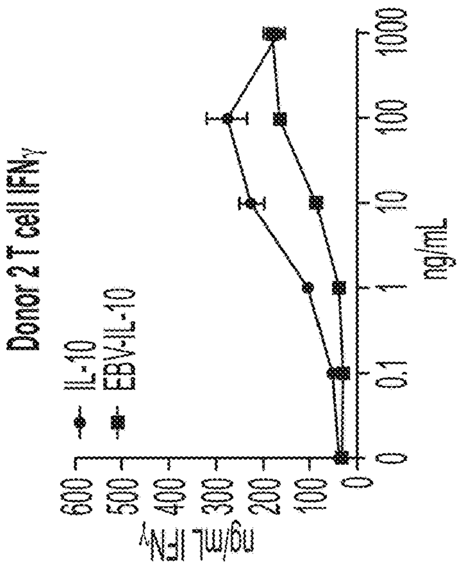
FIGS. 3A-3C compare the ability of IL-10 and EBV IL-10 to activate monocytes/macrophages (Mθ) by examining IL-1β (FIG. 3A) and TNFα (FIG. 3B) cytokine production and the stimulation of T-cells by examining IFNγ (FIG. 3C) production in Donor 1.
Figure 3B:
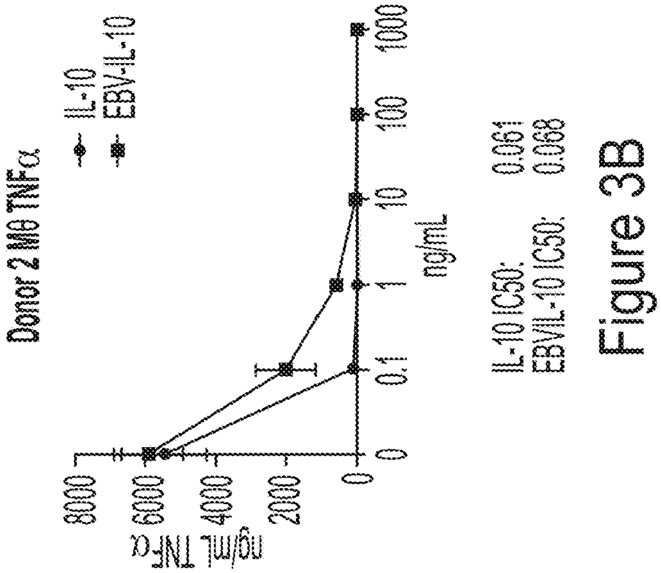
Figure 3A:
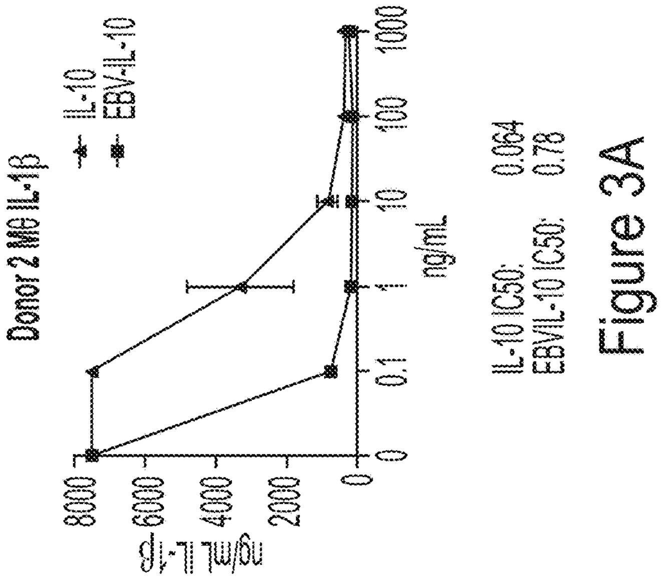
Figure 4A:
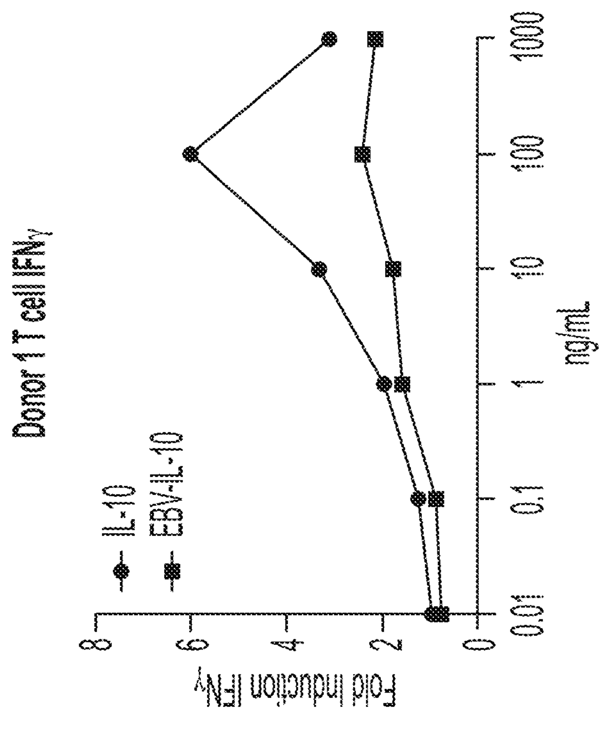
FIGS. 4A-B show the amount of IFNγ induction from T cells following stimulation by IL-10 or EBV IL-10.
Figure 4B:
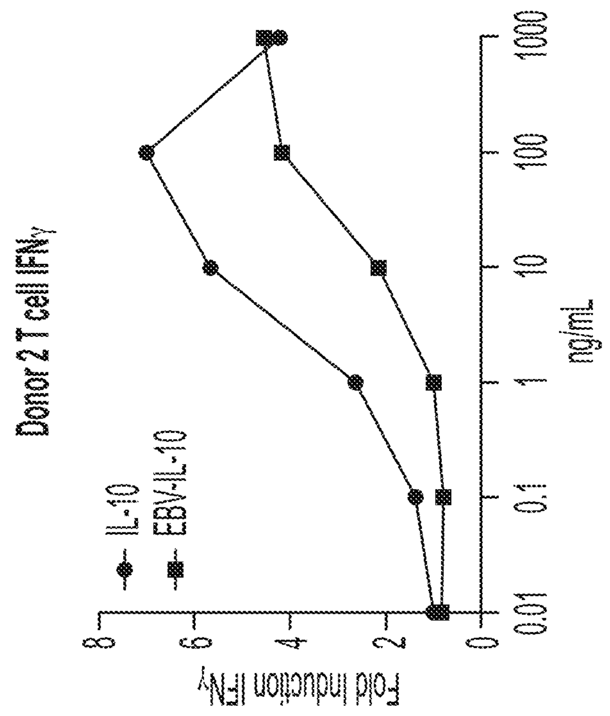

In the study, the above described procedure are used to compare the impacts of non-PEGylated EBV-IL10 and non-PEGylated human IL-10 on the stimulation of $CD8^+$ T cells. FIGS. 2C and 3C show that the EBV-IL10 exhibited diminished levels of IFNγ (a measure of T-cells stimulation) when compared to human IL-10. This indicates that by altering the inter-domain angles, there is an ability to modulate stimulation of T-cells. FIGS. 4A and 4B show that half of the donors treated exhibit the desired complete anti-inflammatory effects and half do not. The variants selected for development will mimic the response of donor 1, complete suppression of inflammatory cytokine secretion in response to LPS by the macrophage cells and the lack of IFNγ induction from activated $CD8^+$ T cells. Donor 2 exhibited a similar suppression of inflammatory cytokine secretion by monocytes/macrophages to Donor 1, but only shifted the curve and maximal activation of T cell IFNγ secretion to the right. IL-10 variant molecules that alter receptor affinity and interdomain angle should further reduce T cell activation in patients similar to donor 2.

Example 4

Figure 5A:
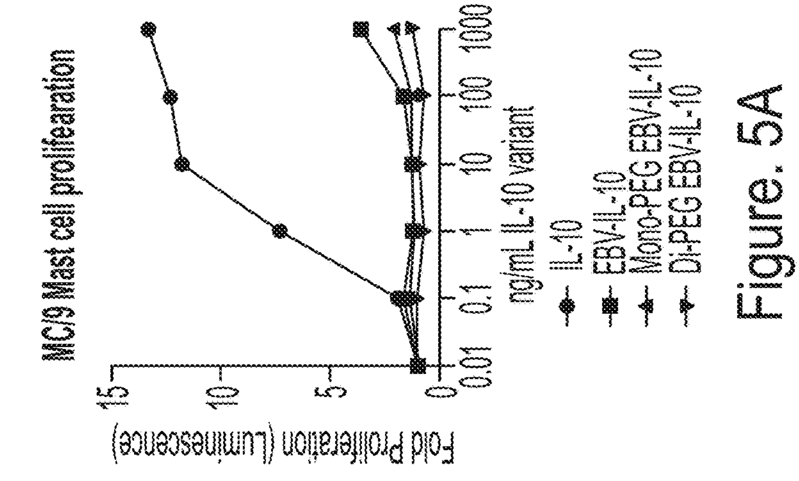
FIGS. 5A-5C show the effect of N-terminal 5 kDa mono and di-PEGylated EBV-IL-10 on MC/9 cell proliferation, (FIG. 5A), TNFα secretion by monocytes/macrophages (Mθ) in response to LPS (FIG. 5B), and IFNγ secretion by T cells in response to T cell receptor stimulation (FIG. 5C).
Figure 5B:
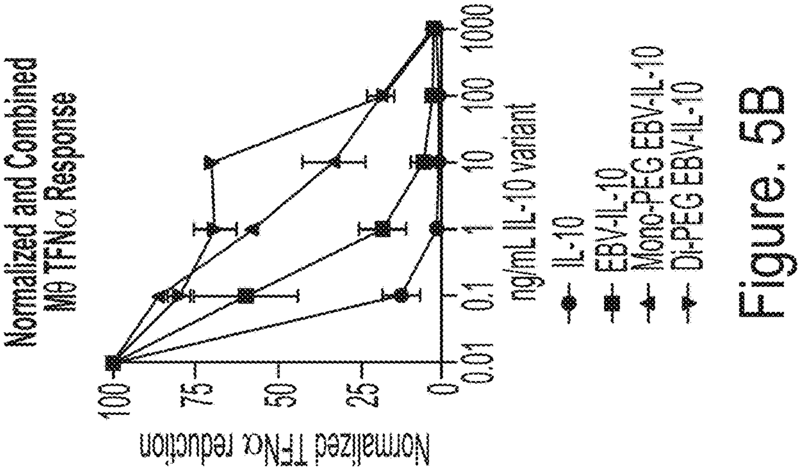
Figure 5C:
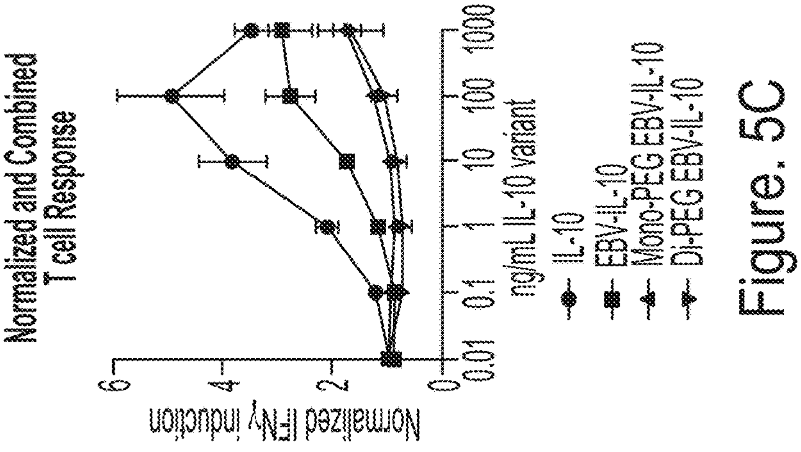
Figure 7:
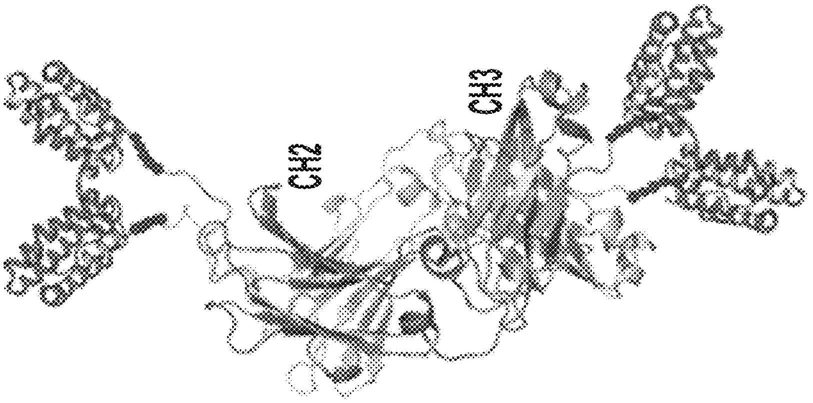
FIG. 7 shows a schematic representation of a fusion protein comprising an IL-10 or IL-10 variant molecule conjugated to a linker or spacer (in this case a scFv). This representative example shows IL-10 or IL-10 variant molecules conjugated for both the N-terminus and the C-terminus.

Human monocycles/macrophages, T cells and murine MC/9 cells purchased from ATCC were cultured as previously stated and the response to mono or di-N-terminally 5 kDa PEGylated EBV-IL10 was evaluated. PEGylation of EBV-IL10 results in a slight reduction of macrophage response to LPS (FIG. 5B), but a near complete suppression of IFNγ induction from stimulated T cells (FIG. 5C). Likewise, PEGylation of EBV-IL10 nearly abolishes it's stimulatory effect on MC/9 cells (FIG. 5A).

Figure 15:
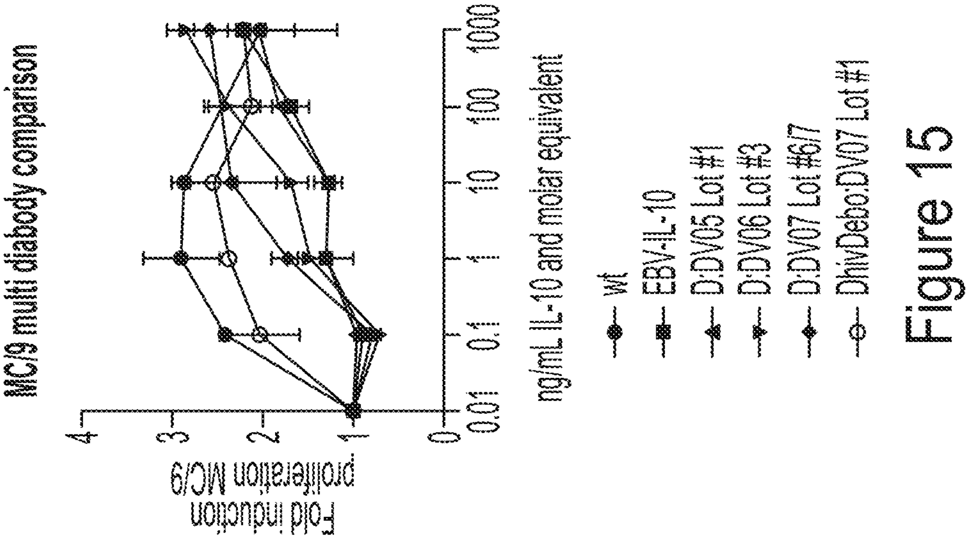
FIG. 15 is a direct comparison of various forms of EBV-10 variant diabody forms on MC/9 mast cells. This assay compares human IL-10, EBV IL-10, D:DV05 (EBV IL-10 with a V31L mutation comprising variable regions from anti-CD3α and anti-EGFR), D:DV06 (EBV IL-10 with a A75I mutation comprising variable regions from anti-CD3α and anti-EGFR), D:DV07 with V31L and A75I mutations comprising variable regions from anti-CD3α and anti-EGFR), and DhivDEbo:DV07 (EBV IL-10 variant diabody with V31L and A75I substitutions comprising variable regions from anti-HIV and anti-Ebola).

Various forms of EBV-IL-10 variant diabody with anti-CD3α and anti-EGFR VH and VL regions were tested using a MC/9 cell proliferation assay. The EBV-10 variant portions included D:DV05 (EBV IL-10 with a V31L mutation), D:DV06 (EBV IL-10 with a A75I mutation), and D:DV07 with V31L and A75I mutations). Additionally a DV07 diabody comprising an anti-HIV and anti-Ebola VH and VL region were also tested. The various variant diabody forms were compared to human IL-10 and EBV IL-10. Results are provided in FIG. 15.

Other forms of the EBV-IL-10 fusion proteins were also tested in vitro. In particular DhivDebo:DV06 (SEQ ID Nos: 26 and 27) and DmadcamDebo:DV06 (SEQ ID Nos: 41 and 42) were compared to human IL-10 in the macrophage and T-cell response assays described herein. The results are provided in FIGS. 20A and 20B.

Example 5

The following example provides a representative protocol for testing the IL-10 and IL-10 variant molecule and fusion proteins thereof in an in vivo tumor model. All in vivo studies are conducted in accordance with the standard operating procedures and established guidelines approved by the Institutional Animal Care and Use Committee ("IACUC").

Eight week-old female Balb/C mice are purchased, quarantined for one week, and maintained on normal chow and water with bedding changes 1 time per week under a standard 24 hour light/dark cycle.

CT26 tumor cells ($2\times10^5$) are suspended in Hanks Buffered Salt solution and subcutaneously implanted into eight week old mice and permitted to grow. CT26 tumor (average 50-150 $mm^3$) bearing wild type Balb/C Envigo), or B cell knockout (Jackson) mice are treated with 0.4 and 0.2 mg/kg three times a week (q3w), 0.2 and 0.1 mg/kg daily (qd) 5 days with two day drug holiday, IL-10 or IL-10 variant molecules or fusion proteins thereof, (e.g., an EBV IL-10 variant molecule harboring two receptor binding substitutions, DV07 (FIG. 8C), covalently linked to VH and VL from two different antibodies or diabody) subcutaneously (scruff) for 10 days. The length and width of tumors are measured every three days by electronic calipers and tumor volume calculated ($(L\times W^2)/2$)). B cells in wild type mice are depleted with intravenous (i.v.) administration of 200 g/mouse anti-murine CD20. Results of one such study are provided in FIG. 16, which used a IL-10 variant molecule termed D:DV07, which is a IL-10 variant harboring V31L and A75I mutations comprising variable regions from anti-CD3α and anti-EGFR.

Figure 9A:
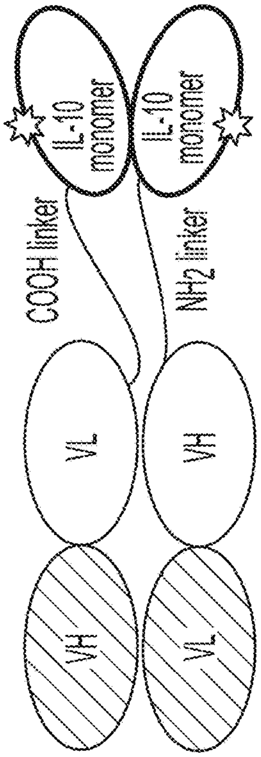
FIGS. 9A-9F are a schematic representation of various configurations of IL-10 fusion protein/immunoconjugate/diabody constructs.
Figure 9B:
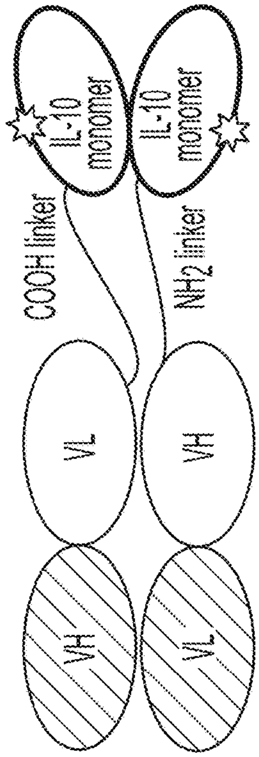
Figure 9C:
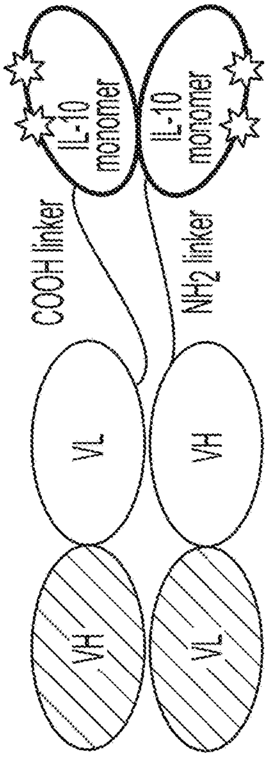
Figure 9D:
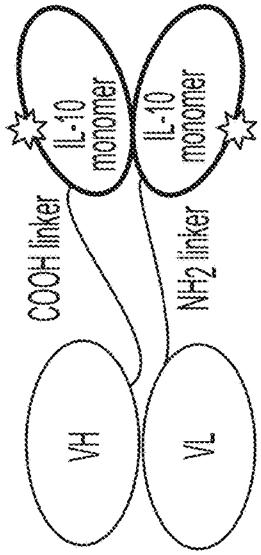
Figure 9E:
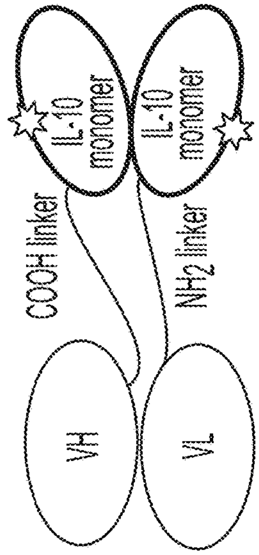
Figure 9F:
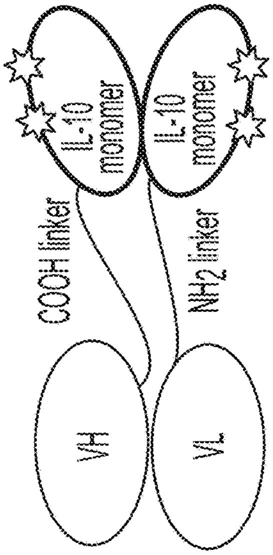
Figure 10A:
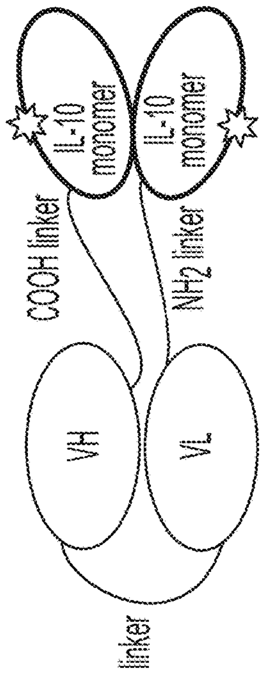
FIGS. 10(A)-10(F) are a schematic representations of various configurations of the IL-10 fusion protein/immunoconjugate/diabody constructs.
Figure 10B:
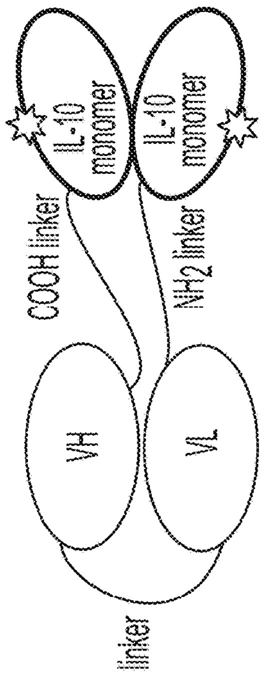
Figure 10C:
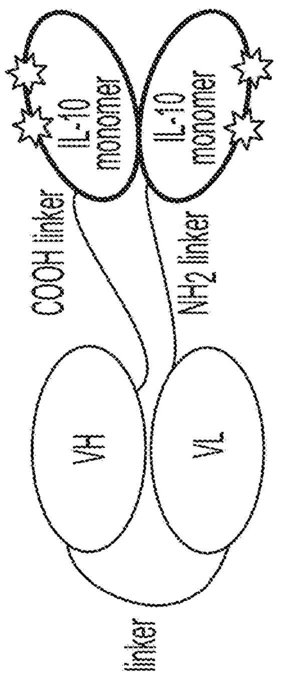
Figure 10D:
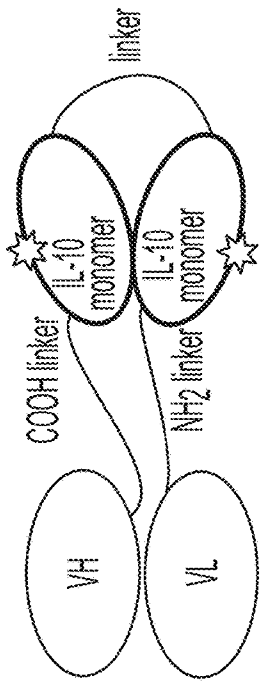
Figure 10E:
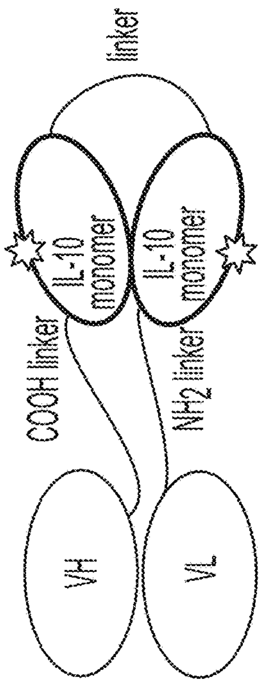
Figure 10F:
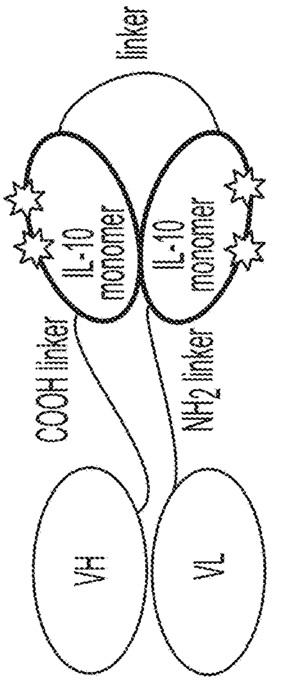
Figure 11:
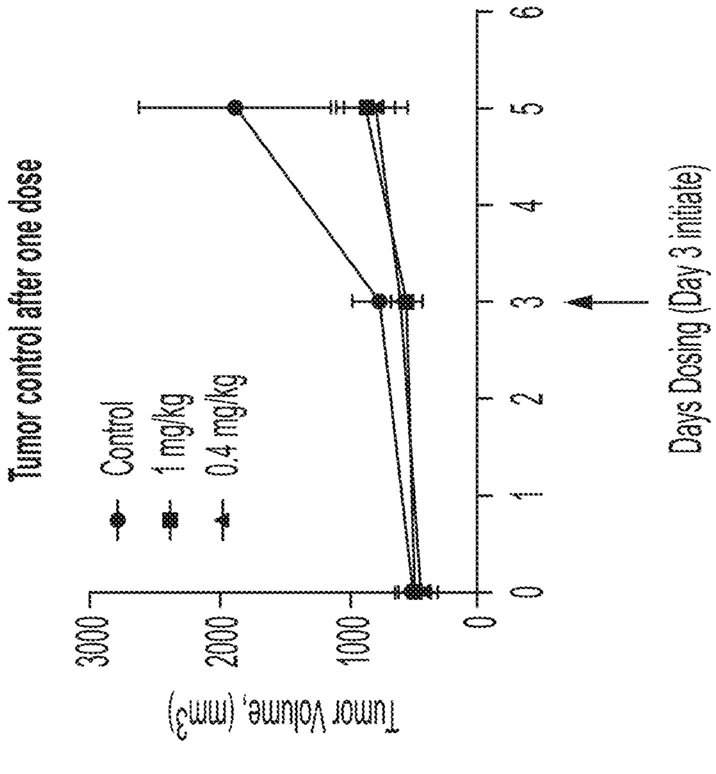
FIG. 11 shows the in vivo reduction of tumor volume using a diabody comprising the DV07 mutation. Formulation buffer (1× Phosphate Buffered Saline; "control") and a DV07 diabody (a fusion protein complex comprising the EBV IL-10 variant with V31L V31L and A75I A75I of the mature protein and variable domains from anti-CD3α and anti-EGFR, neither of these VH/VL pais bind to the mouse target) were administered at a single dose at day 3. The dose concentrations of 1 mg/kg and 0.4 mg/kg were tested for the DV07 diabody.
Figure 12:
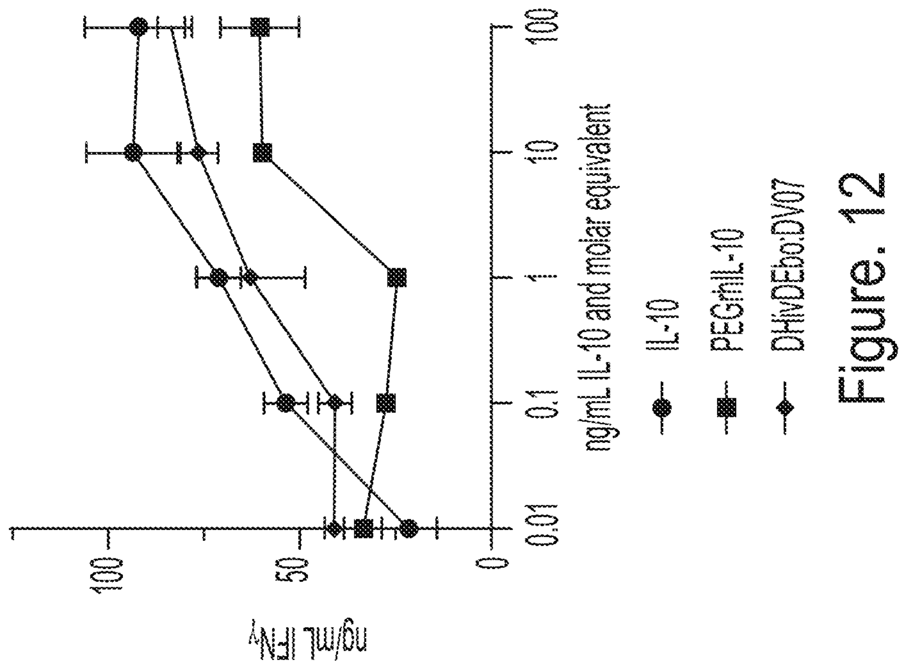
FIG. 12 shows the in vitro T-cell response to a published variant of IL-10 (diamond), wild-type IL-10 (circle) and an alternative form of a DV07 diabody termed DHivDEbo:DV07 (diamond; a fusion protein complex comprising the EBV IL-10 variant with V31L and A75I mutations and variable domains from anti-HIV and anti-Ebola (neither of these VH/VL pairs bind to mouse proteins), where the diabody has a structure schematically represented by FIG. 9(*c*)).
Figure 13B:
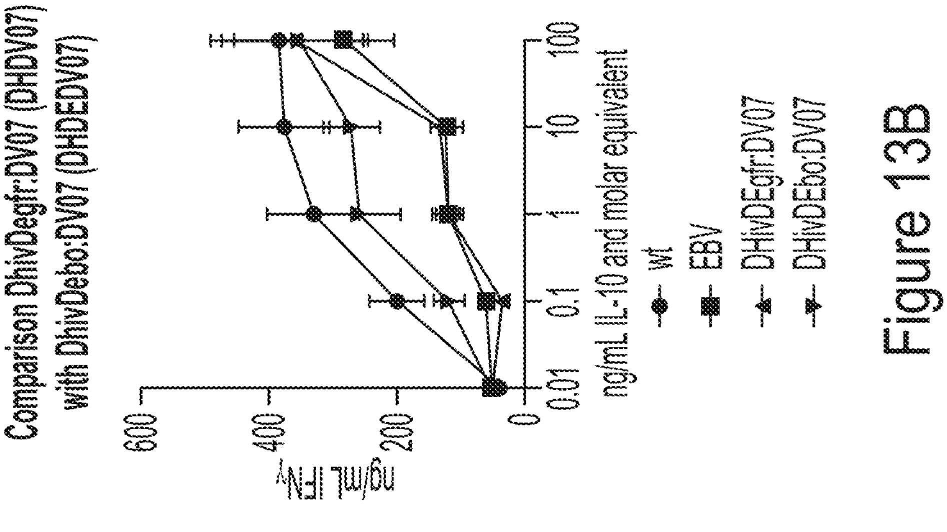
FIG. 13B compares the secretion of IFNγ in T-cell in response assay using human IL-10 ("wt") EBV IL-10 ("EBV") to various diabody forms comprising an EBV IL-10 variant molecules with the V31L and A75I mutations and VH and VL regions from different antibodies. Form DHivDEgfr:DV07 is an EBV IL-10 variant diabody with V31L and A75I substitutions comprising variable regions from anti-HIV and anti-EGFR. Form DHivDEbo:DV07 is an EBV IL-10 variant diabody with both V31L and A75I mutations comprising variable regions from anti-HIV and anti-Ebola.
Figure 13A:
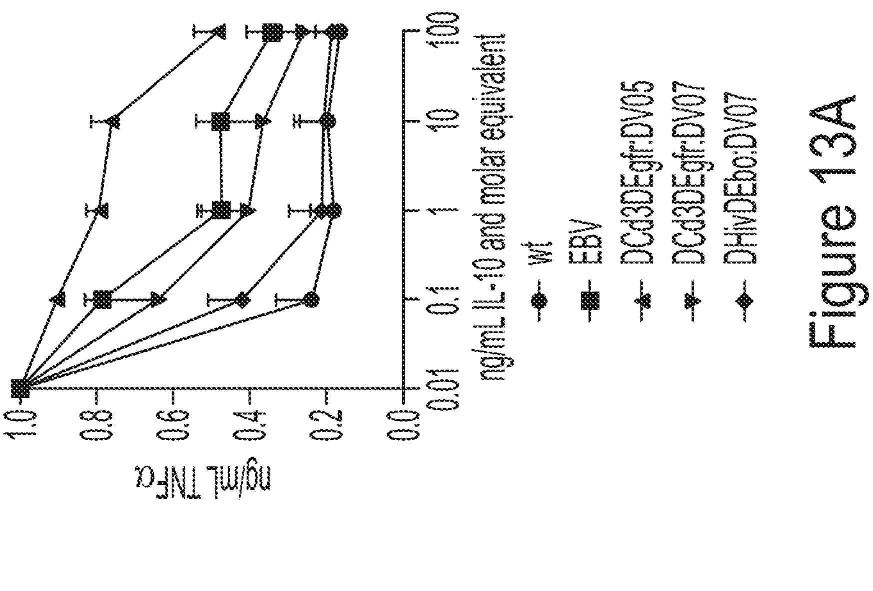
FIG. 13A compares the suppression of TNFα induced by LPS exposure to monocytes/macrophages using various forms of the EBV IL-10 variant molecule with the V31L and A75I mutations in diabody form. "wt" represents human IL-10; "EBV" is EBV L1-10; "DCd3DEgfr:DV05" is a diabody comprising VH and VL regions from an anti-CD3 antibody and an anti-EGFR antibody linked to an EBV IL-10 variant comprising a V31L mutation; "DCd3DEgfr:DV07" is a diabody comprising VH and VL regions from an anti-CD3 antibody and an anti-EGFR antibody linked to an EBV IL-10 variant comprising both V31L and A75I mutations; "DHivDEbo:DV07" is a diabody comprising VH and VL regions from an anti-HIV antibody and an anti-Ebola antibody linked to an EBV IL-10 variant comprising both V31L and A75I mutations.
Figure 14B:
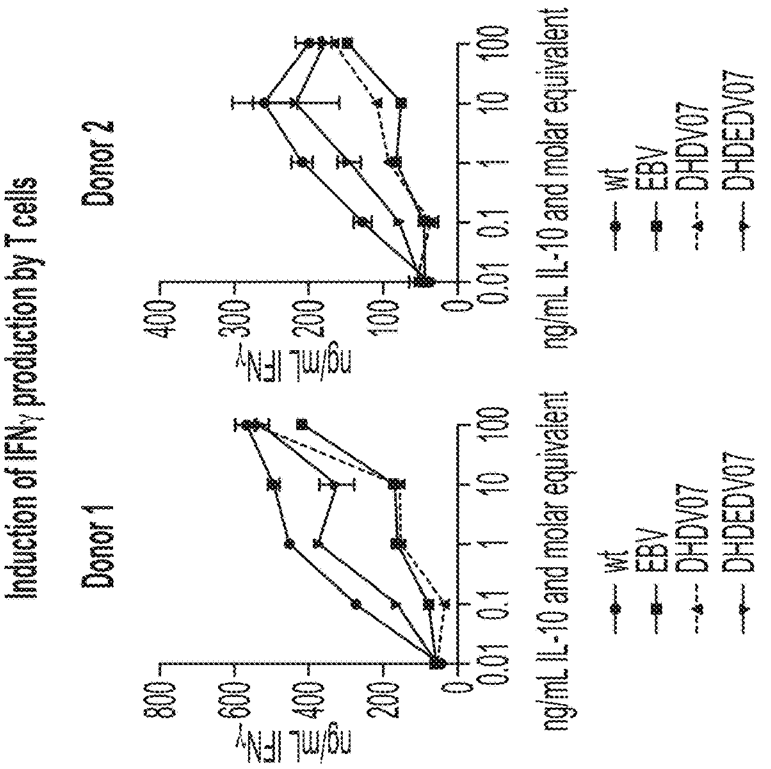
FIGS. 14A-14B compare two forms of the EBV IL-10 variant diabody, DH:DV07 and DHDE:DV07 on monocytes/macrophages (FIG. 14A) and T-cells (FIG. 14B) isolated from two donors. Form DHDV07 is an EBV IL-10 variant diabody with V31L and A75 substitutions comprising variable regions from anti-HIV and anti-EGFR. Form DHDE:DV07 is an EBV IL-10 variant diabody with V31L and A75I substitutions comprising variable regions from anti-HIV and anti-Ebola.
Figure 14A:
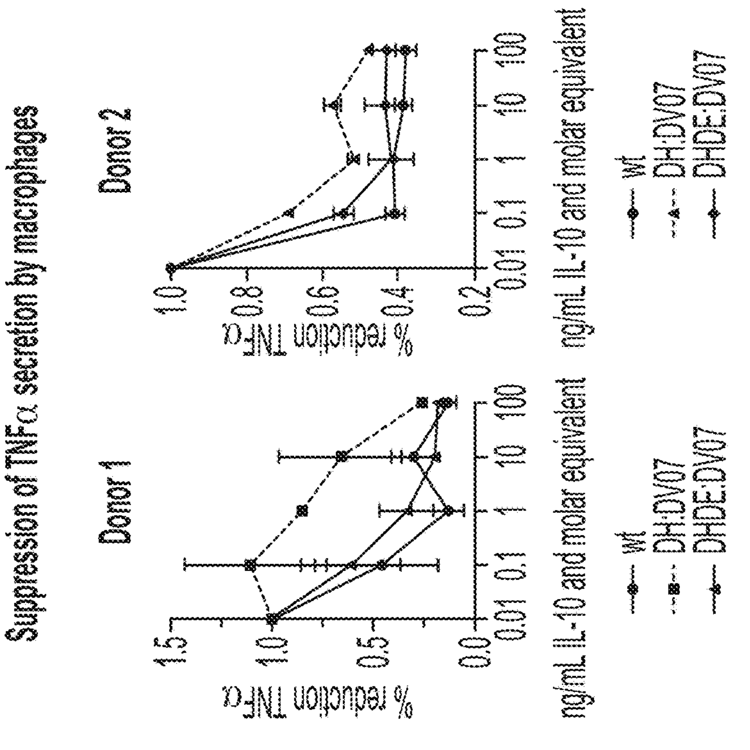
Figure 17B:
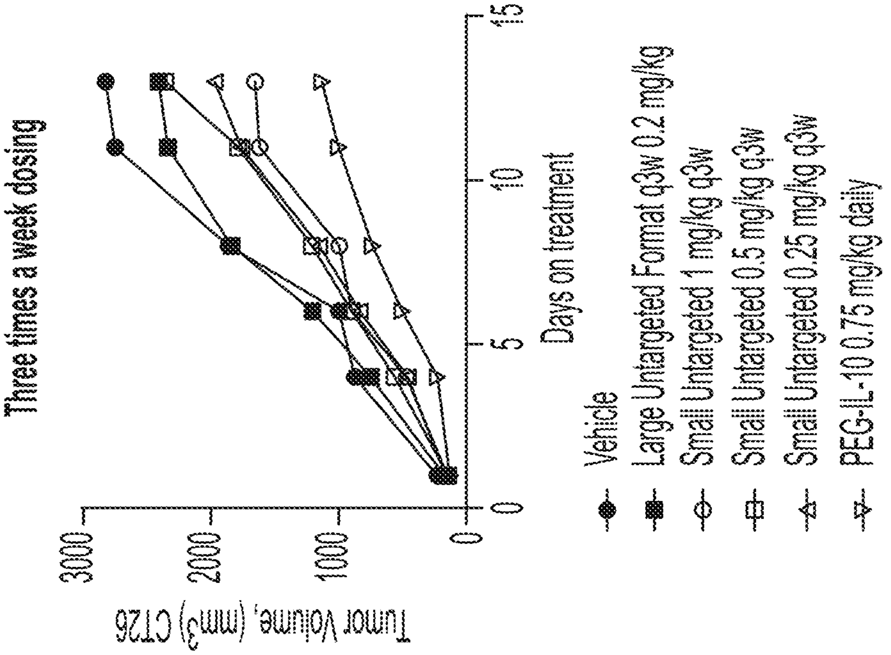
FIGS. 17A-17B are results from an in vivo studies of two IL-10 variant fusion protein formats, large molecular weight (large) and small molecular weight (small), that correspond to the schematic diagrams of FIGS. 9C and 9F respectively. The IL-10 variant comprises V31L and A75I mutations. These results tested the impact of IL-10 fusion proteins without targeting capabilities to reduce tumor size. The VH and VL regions from the fusion proteins are non-targeting sequences, from either an anti-HIV and anti-ebola (large) or anti-ebola (small).
Figure 17A:
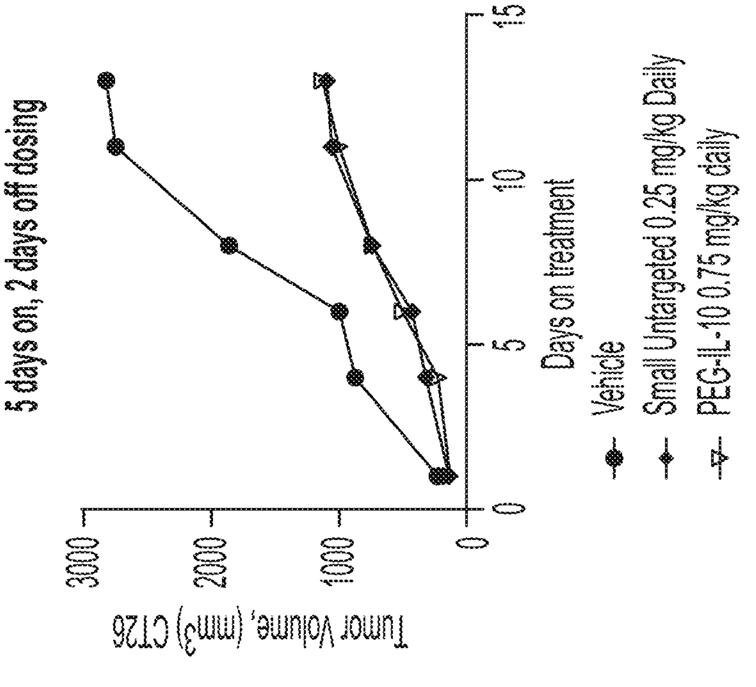

In FIGS. 17A and 17B, two formats of the IL-10 variant fusion proteins (i.e., IL-10 variant comprising both V31L and A75I mutations, DV07) represented by FIGS. 9C (large format) and 9*f* (small format) are compared in an in vivo tumor model. The fusion proteins are non-targeting fusion proteins and comprising VH and VL regions from an anti-FHV antibody and an anti-ebola antibody (large format) and the VH and VL region from an anti-ebola antibody. The dosing study examined the effects of the small format non-targeting IL-10 fusion protein administered 5 days on, 2 days off (FIG. 17A) compared to pegylated recombinant human IL-10 (0.75 mg/kg daily). The dosing study also examined the effects of the large and small formatted non-targeting IL-10 fusion protein administered three times a week (FIG. 17B) compared to pegylated IL-10 (0.75 mg/kg daily).

Figure 18A:
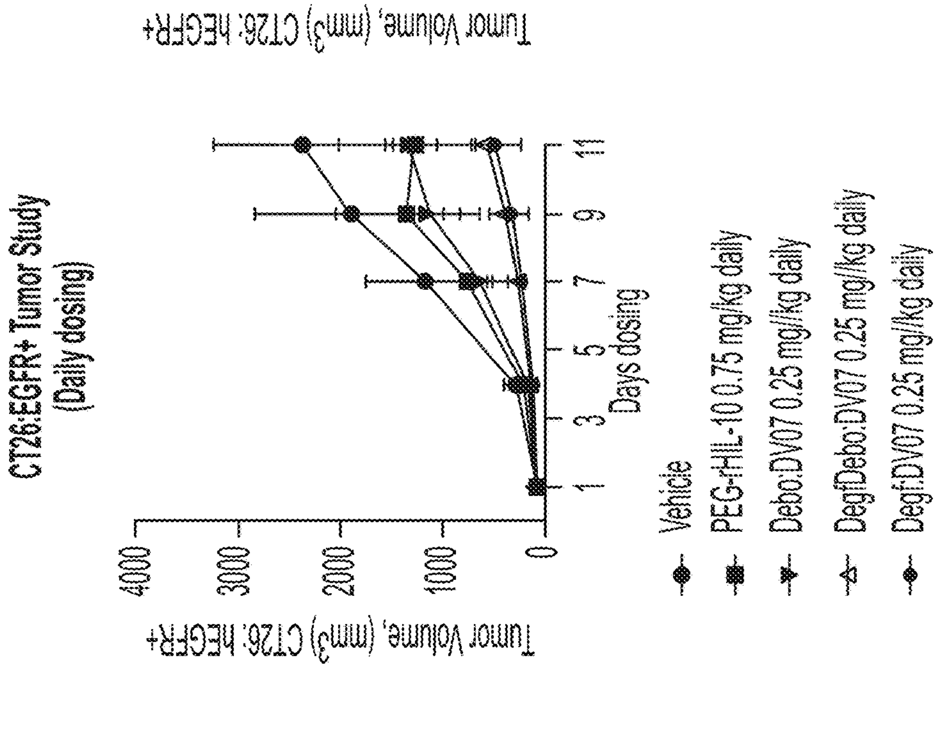
FIGS. 18A-18C are results from an in vivo study of two IL-10 variant fusion protein formats, large and small, that correspond to the schematic diagrams of FIGS. 9C and 9F, respectively. These results tested the impact of IL-10 fusion proteins with targeting capabilities to reduce tumor size. The IL-10 variant comprises V31L and A75I mutations. In the large format, one set of the VH and VL region from the fusion proteins are from an anti-EGFR antibody, while the other set of the VH and VL is from an anti-ebola antibody. The small format include VH and VL from just an anti-EGFR antibody.
Figure 18B:
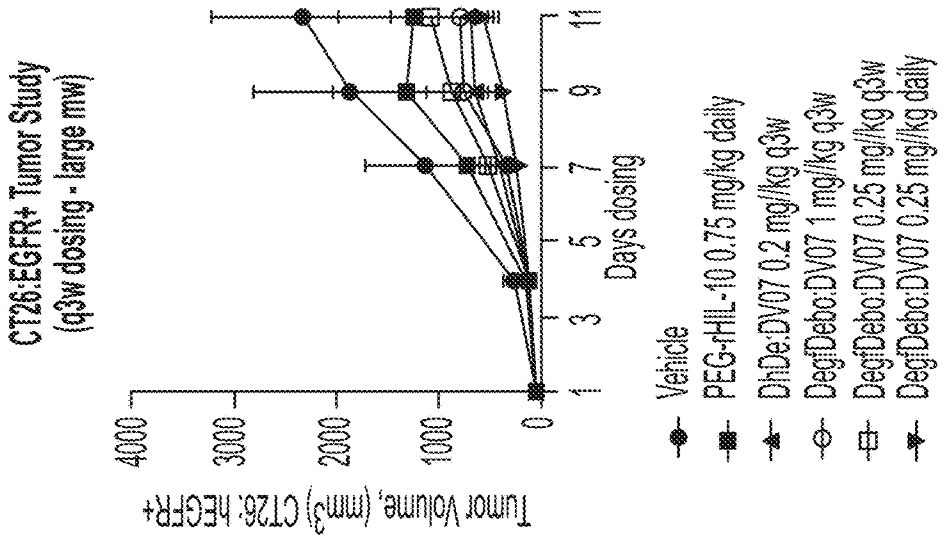
Figure 18C:
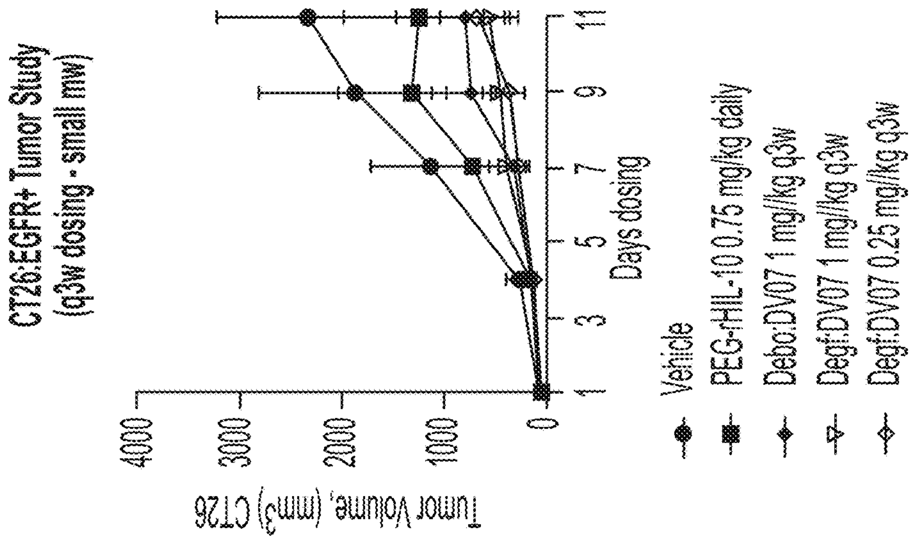

Studies using the small and large format IL-10 fusion proteins (i.e., IL-10 variant comprising both V31L and A75I mutations, DV07) having tumor targeting capabilities were also tested in vivo. FIG. 18A are the results from daily administration of various targeting IL-10 variant fusion proteins, where large format (DegfDebo:DV07) and small format (Degf:DV07) were compared to a small format non-targeting (Debo:DV07) IL-10 fusion protein and pegylated IL-10. FIG. 18B are the results from three times a week administration of various large format targeting IL-10 variant fusion proteins, where large format (DegfDebo:DV07) at various doses (1 mg/kg and 0.25 mg/kg) were compared to a small format non-targeting (DhDe:DV07) IL-10 fusion protein and pegylated IL-10. FIG. 18C are the results from three times a week administration of various small format targeting IL-10 variant fusion proteins, where small format (Degf:DV07) at various doses (1 mg/kg and 0.25 mg/kg) were compared to a small format non-targeting (Debo:DV07) IL-10 fusion protein and pegylated IL-10.

Example 6

The following example provides a representative protocol for testing the IL-10 and IL-10 variant molecule and fusion proteins thereof in an in vivo cholesterol model. All in vivo studies were conducted in accordance with the standard operating procedures and established guidelines approved by the IACUC.

Eight week-old female C57BL/6J mice are purchased from an appropriate vendor, quarantined for one week and maintained on normal chow and water with bedding changes one time/week under a standard 24 hour light/dark cycle.

Eight week-old female C57BL/6J mice Jackson Laboratories are fed a high fat diet (Envigo) for three weeks. Plasma samples are obtained by retro-orbital bleeding of each mouse prior to treatment with an IL-10 or IL-10 variant or fusion protein thereof (e.g., EBV IL-10 variant comprising a single substitution at amino acid position 31 (V31L) of SEQ ID No: 3 linked to a diabody (D:DV05 EBV IL-10 variant)). Mice are treated subcutaneously for two weeks with 0.4 and 0.2 mg/kg three times a week (q3w) as well as 0.2 and 0.1 mg/kg weekly (qd) 5 days treatment with a 2-day therapy holiday. Animals are treated for two weeks and terminal blood draws are taken after which the pre and post-dose plasma cholesterol concentration is quantified. On the day prior to treatment initiation, B cells are depleted with intravenous (i.v.) administration of 200 μg/mouse anti-murine CD20. Results of one such study is provided in FIGS. 19A and 19B.

Example 7

The following example provides a representative protocol for testing the IL-10 and IL-10 variant molecule and fusion proteins thereof in an in vivo dextran sodium sulfate ("DSS") inflammation model. All in vivo studies are conducted in accordance with the standard operating procedures and established guidelines approved by the IACUC.

Eight week-old female Balb/C mice are purchased from an appropriate vendor, quarantined for one week and maintained on normal chow and water with bedding changes 1 time/week under a standard 24 hour light/dark cycle. B cell knockout (Jackson) mice are fed 4% DSS in water ad libitum for six days after which they are provided normal water. At day 5, mice are treated with 0.4 and 0.2 mg/kg three times a week (q3w), 0.2 and 0.1 mg/kg daily (qd) 5 days with two-day drug holiday, an IL-10 or IL-10 variant or fusion protein thereof (e.g., EBV IL-10 variant comprising a single substitution at amino acid position 75 (A75I) of SEQ ID No: 3 linked to a diabody (D:DV06 EBV IL-10 variant)) subcutaneously (scruff) for 10 days. Mice are assessed daily for:

1.) Weight
2.) Stool blood
3.) Gross blood
4.) Stool consistency

Disease activity index are determined by combining scores of;

1. Weight loss
2. Stool consistency
3. Bleeding (divided by 3)

Each score is determined as follows: change in weight (0: <1%, 1: 1-5%, 2: 5-10%, 3: 10-15%, 4 >15%, stool blood (0:

negative, 2: positive) or gross bleeding (4) and stool consistency (0: normal, 2: loose stools, 4: diarrhea).

A Listing of Preferred Embodiments

1. An Epstein-Barr viral IL-10 (EBV-IL10) variant protein comprising one or more amino acid additions, deletions, and/or substitutions exhibiting an altered inter-domain angle and/or an altered affinity for a cognate receptor when compared to the wild-type EBV-IL10, wherein the altered inter-domain angle, when dimerized, modulates an angle of engagement with the cognate receptor.

2. An EBV-IL10 protein according to the preceding embodiment, wherein the one or more amino acid additions, deletions, and/or substitutions is located in the IL-10 receptor binding domain.

3. An EBV-IL10 protein according to any of the preceding embodiments, wherein the one or more amino acid additions, deletions, and/or substitutions is located within alpha helix A and/or helix D.

4. An EBV-IL10 protein according to any of the preceding embodiments, wherein the one or more amino acid additions, deletions, and/or substitutions resides in the linkage domain of EBV-IL10.

5. An EBV-IL10 protein according any of the preceding embodiments, wherein the one or more amino acid additions, deletions, and/or substitutions is located within the DE loop of EBV-IL10.

6. An EBV-IL10 protein according to any of the preceding embodiments, wherein the one or more amino acid addition, deletion, and/or substitution is located within the 12 amino acid linker region found between alpha helix D and alpha helix E or alpha helix C and alpha helix D, preferably an addition or substitution of a proline within the 12 amino acid linker region.

7. An EBV-IL10 protein according to any of the preceding embodiments, wherein the altered affinity for the cognate receptor comprises one or more amino acid additions, deletions, and/or substitutions in the IL-10 receptor binding domain.

8. An EBV-IL10 protein according to any of the preceding embodiments, further comprising one or more amino acid additions, deletions, and/or substitutions located within alpha helix A and/or alpha helix D.

9. An EBV-IL10 protein according to any of the preceding embodiments, further comprising one or more amino acid additions, deletions, and/or substitutions in the IL-10 receptor binding domain.

10. An EBV-IL10 protein according to any of the preceding embodiments, further comprising one or more amino acid additions, deletions, and/or substitutions located within alpha helix A and/or alpha helix D.

11. An EBV-IL10 protein according to any of the preceding embodiments, wherein the one or more amino acid additions, deletions, and/or substitutions is at amino acid position 31 and/or 75 of SEQ ID No. 3.

12. A monomeric recombinant protein comprising six alpha helices numbered A-F capable of forming a homodimer with an identical monomeric protein, wherein alpha helices D and E are linked by an inter-chain amino acid linker, the linker being modified with an addition, a deletion, or a substitution of at least one amino acid that alters an inter-molecular angle of the protein when homodimerized.

13. A recombinant protein according to the preceding embodiment, wherein the protein is a protein from a virus.

14. A recombinant protein according to any of the preceding embodiments, wherein the virus is a Epstein-Barr virus (EBV).

15. A recombinant protein according to any of the preceding embodiments, wherein the homodimer formed between two identical monomeric proteins forms an specific angle of interaction with its cognate receptor.

16. A recombinant protein according to any of the preceding embodiments, wherein the angle of interaction is greater than the natural wild-type protein.

17. A recombinant protein according to any of the preceding embodiments, wherein the angle of interaction formed upon homodimerization results in a protein having higher affinity for the cognate receptor.

18. A recombinant protein according to any of the preceding embodiments, wherein the angle of interaction formed upon homodimerization results in a protein having a lower affinity for the cognate receptor.

19. A recombinant protein according to any of the preceding embodiments, wherein the angle of interaction is less than the natural wild-type protein.

20. A recombinant protein according to any of the preceding embodiments, wherein the angle of interaction results in a protein having higher affinity for the cognate receptor.

21. A recombinant protein according to any of the preceding embodiments, wherein the angle of interaction results in a protein having less affinity for the cognate receptor.

22. A recombinant protein according to any of the preceding embodiments, wherein the monomeric protein is an interleukin 10.

23. A recombinant protein according to any of the preceding embodiments, wherein the monomeric protein is an EBV-IL10.

24. A recombinant protein according to any of the preceding embodiments, wherein the angle of the protein is imparted by modifications to the linker resulting in an angle of interaction with a cognate receptor.

25. A recombinant variant Epstein-Barr viral IL-10 (EBV-IL10) protein comprising at least one amino acid addition, deletion, or substitution to the linker region between alpha helix D and E of EBV-IL10 and/or to the receptor binding region of EBV-IL10.

26. An recombinant protein according to the preceding embodiment, wherein the variant EBV-IL10 protein interacts with an identical protein resulting in a homodimer having an altered angle of interaction with its cognate receptor and/or an altered inter-homodimeric angle.

27. An recombinant protein according to any of the preceding embodiments, wherein the variant EBV-IL10 protein forms an angle of interaction and/or altered inter-homodimeric angle that is greater than a wild-type EBV-IL10 protein.

28. An recombinant protein according to any of the preceding embodiments, wherein the variant EBV-IL10 protein forms an angle of interaction and/or altered inter-homodimeric angle that is less than a wild-type EBV-IL10 protein.

29. An recombinant protein according to any of the preceding embodiments, wherein the angle of interaction form upon homodimer formation results in a variant EBV-IL10 protein having increased affinity to its cognate receptor.

30. An recombinant protein according to any of the preceding embodiments, wherein the angle of interaction form upon homodimer formation results in a variant EBV-IL10 protein having diminished affinity to its cognate receptor.

31. An recombinant protein according to any of the preceding embodiments, wherein the angle of interaction imparts an increase in affinity to its cognate receptor.

32. An recombinant protein according to any of the preceding embodiments, wherein the angle of interaction imparts an decrease in affinity to its cognate receptor.

33. An isolated recombinant polynucleotide encoding the protein according to any of the preceding embodiments.

34. An isolated recombinant polynucleotide encoding the protein according to any of the preceding embodiments.

35. A vector comprising a nucleic acid encoding the protein according to any of the preceding embodiments.

36. A host cell comprising the polynucleotide according to any of the preceding embodiments.

37. A method of treating or preventing inflammation in a subject comprising administering to the subject a therapeutically effective amount of the variant protein according to any of the preceding embodiments.

38. A method according to the preceding embodiment, wherein the altered angle of the variant protein is less than wild-type EBV-IL10.

39. A method according to any of the preceding embodiments, wherein the variant protein binds with moderate affinity to the IL10 receptor when compared to wild-type EBV-IL10.

40. A method according to any of the preceding embodiments, wherein the inflammation is Inflammatory Bowel Disease (IBD), Crohn's disease, Non-Alcoholic Steatohepatiti (NASH), Non-Alcoholic Fatty Liver Disease (NAFLD), psoriasis, rheumatoid arthritis, acute anaphylactic shock, and/or seasonal allergies.

41. A method of treating or preventing auto-immune disease in a subject comprising administering to the subject a therapeutically effective amount of the variant protein according to any of the preceding embodiments.

42. A method according to the preceding embodiment, wherein the altered angle of the variant protein is less than wild-type EBV-IL10.

43. A method according to any of the preceding embodiments, wherein the variant protein binds with moderate affinity to the IL10 receptor when compared to wild-type EBV-IL10.

44. A method of treating or preventing IBD or Crohn's Disease in a subject comprising administering to the subject a therapeutically effective amount of the variant protein according to any of the preceding embodiments.

45. A method according to the preceding embodiment, wherein the altered angle of the variant protein is less than wild-type EBV-IL10.

46. A method according to any of the preceding embodiments, wherein the variant protein binds with moderate affinity to the IL10 receptor when compared to wild-type EBV-IL10.

47. A method of treating or preventing Non-Alcoholic Fatty Liver Disease (NAFLD) or Non-Alcoholic Steatohepatiti (NASH) in a subject comprising administering to the subject a therapeutically effective amount of the variant protein according to embodiment 1.

48. A method according to the preceding embodiment, wherein the altered angle of the variant protein is less than wild-type EBV-IL10.

49. A method according to any of the preceding embodiments, wherein the variant protein binds with moderate affinity to the IL10 receptor when compared to wild-type EBV-IL10.

50. A method of treating or preventing cancer in a subject comprising administering to the subject a therapeutically effective amount of the variant protein according to any of the preceding embodiments.

51. A method according to the preceding embodiment, wherein the altered angle of the variant protein is greater than wild-type EBV-IL10.

52. A method according to any of the preceding embodiments, wherein the variant protein binds with increased affinity to the IL10 receptor when compared to wild-type EBV-IL10.

53. An engineered fusion protein comprising at least one monomer of IL-10 or IL-10 variant molecule conjugated at a first terminal end of the fusion protein, at least one cytokine or monomer thereof conjugated at a second terminal end of the fusion protein, and a linker or spacer, wherein the linker or spacer connects the first and second terminal ends.

54. A fusion protein according to the preceding embodiment, wherein the linker or spacer is a constant region of an antibody.

55. A fusion protein according to any of the preceding embodiments, wherein the constant region is derived from an IgG1, IgG2, IgG3, IgG4, IgA, IgM, IgD, or IgE.

56. A fusion protein according to any of the preceding embodiments, wherein the linker or spacer further comprises at least two interchain disulfide bonds.

57. A fusion protein according to any of the preceding embodiments, wherein the linker or spacer is a scFv, a diabody, or fragments thereof.

58. A fusion protein according to any of the preceding embodiments, wherein the constant region is a heavy chain constant (CH) region 1, CH2, CH3, or any combination thereof.

59. A fusion protein according to any of the preceding embodiments, wherein the at least one IL-10 or IL-10 variant molecule is conjugated at the fusion protein's N-terminal end, the C-terminal end, or both.

60. A fusion protein according to any of the preceding embodiments, wherein the at least one cytokine conjugated at another terminal end includes IL-10, IL-10 variant molecule IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13, or any combination thereof.

61. A fusion protein according to any of the preceding embodiments, wherein the fusion protein comprises two IL-10 or IL-10 variant molecules conjugated at the N-terminal end of the fusion protein and two IL-10 or IL-10 variant molecules conjugated at the C-terminal end of the fusion protein.

62. A fusion protein according to any of the preceding embodiments, wherein the fusion protein comprises two IL-10 or IL-10 variant molecules conjugated at the N-terminal end of the fusion protein and at least one IL-2 molecules conjugated at the C-terminal end of the fusion protein.

63. A fusion protein according to any of the preceding embodiments, wherein the C-terminal further comprises an IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13.

64. A fusion protein according to any of the preceding embodiments, wherein the fusion protein comprises two IL-10 or IL-10 variant molecules conjugated at the N-terminal end of the fusion protein and at least one IL-15 molecules conjugated at the C-terminal end of the fusion protein.

65. A fusion protein v, wherein the C-terminal further comprises an IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13.

66. A fusion protein according to any of the preceding embodiments, wherein the fusion protein comprises two IL-10 or IL-10 variant molecules conjugated at the N-terminal end of the fusion protein and at least one IL-2 molecules conjugated at the C-terminal end of the fusion protein.

67. A fusion protein according to any of the preceding embodiments, wherein the C-terminal further comprises an IL-10, IL-10 variant molecule IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13.

68. A fusion protein according to any of the preceding embodiments, wherein the fusion protein is fabricated on a single chain variable fragment (scFv) scaffold.

69. A fusion protein according to any of the preceding embodiments, wherein the fusion protein is fabricated on a diabody scaffold.

70. A fusion protein according to any of the preceding embodiments, wherein the fusion protein is fabricated on an Fab scaffold.

71. A fusion protein according to any of the preceding embodiments, wherein the fusion protein complexes with another fusion protein having at least one monomer of IL-10 or IL-10 variant molecule conjugated at a first terminal end of the fusion protein, at least one cytokine or monomer thereof conjugated at a second terminal end of the fusion protein, and a linker or spacer, wherein the linker or spacer connects the first and second terminal ends.

72. A method of treating cancer in a subject in need thereof comprising administering to the subject the engineered fusion protein according to any of the preceding embodiments.

73. A method of treating or preventing IBD or Crohn's Disease comprising administering to a subject the engineered fusion protein according to any of the preceding embodiments.

74. A method of treating or preventing Non-Alcoholic Fatty Liver Disease (NAFLD) or Non-Alcoholic Steatohepatitis (NASH) in a subject comprising administering to the subject the engineered fusion protein according to any of the preceding embodiments.

75. A method of activating CD8 positive T-cell comprising administering the engineered fusion protein according to any of the preceding embodiments.

76. A method according to any of the preceding embodiments, wherein the administration is in vitro administration.

77. A method according to any of the preceding embodiments, wherein the administration is in vivo administration to a subject in need thereof, wherein the subject has been diagnosed with cancer, IBD or Crohn's disease, or NAFLD or NASH.

78. A method according to any of the preceding embodiments, wherein the fusion protein comprises a IL-10 or IL-10 variant molecule at the first terminal end of the fusion protein and an IL-2 and/or IL-15 at the second terminal end of fusion protein.

79. A method of treating cancer in a subject in need thereof comprising administering to the subject a bispecific T-cell engager (BITE) and an IL-10, an IL-10 variant molecule, or an engineered fusion protein comprising an IL-10 or an IL-10 variant molecule.

80. A method according to the preceding embodiment, wherein the engineered fusion protein comprises at least one IL-10 or IL-10 variant molecule conjugated at a first terminal end of the fusion protein, at least one cytokine conjugated at a second terminal end of the fusion protein, and a linker or spacer, wherein the linker or spacer connects the first and second terminal ends.

81. A method according to any of the preceding embodiments, wherein the IL-10, IL-10 variant molecule, or the engineered fusion protein comprising an IL-10 or an IL-10 variant molecule increases and sustains T-cell receptor complex (CD3) signal transduction.

82. A method of treating or preventing inflammation in a subject comprising administering to the subject a therapeutically effective an amount of a nucleotide sequence encoding a variant IL-10 molecule.

83. A method according to the preceding embodiment, wherein the nucleotide sequence is DNA, RNA, or modified variants thereof.

84. A method according to any of the preceding embodiments, wherein the nucleotide sequence is a mRNA or a modified mRNA linked to a nucleoside.

85. A method according to any of the preceding embodiments, wherein the nucleotide sequence is capable of in vivo expressing the variant IL-10 molecule within a cell, tissue, or organism.

86. A method according to any of the preceding embodiments, wherein the nucleotide sequence is delivered to a cell, tissue, or organism by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer.

87. A method of treating or preventing auto-immune disease in a subject comprising administering to the subject a therapeutically effective amount of a nucleotide sequence encoding a variant IL-10 molecules.

88. A method according to the preceding embodiment, wherein the nucleotide sequence is DNA, RNA, or modified variants thereof.

89. A method according to any of the preceding embodiments, wherein the nucleotide sequence is a mRNA or a modified mRNA linked to a nucleoside.

90. A method according to any of the preceding embodiments, wherein the nucleotide sequence is capable of in vivo expressing the variant IL-10 molecule within a cell, tissue, or organism.

91. A method according to any of the preceding embodiments, wherein the nucleotide sequence is delivered to a cell, tissue, or organism by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer.

92. A method of treating or preventing IBD or Crohn's Disease in a subject comprising administering to the subject a therapeutically effective amount of a nucleotide sequence encoding a variant IL-10 molecule.

93. A method according to the preceding embodiment, wherein the nucleotide sequence is DNA, RNA, or modified variants thereof.

94. A method according to any of the preceding embodiments, wherein the nucleotide sequence is a mRNA or a modified mRNA linked to a nucleoside.

95. A method according to any of the preceding embodiments, wherein the nucleotide sequence is capable of in vivo expressing the variant IL-10 molecule within a cell, tissue, or organism.

96. A method according to any of the preceding embodiments, wherein the nucleotide sequence is delivered to a cell, tissue, or organism by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer.

97. A method of treating or preventing Non-Alcoholic Fatty Liver Disease (NAFLD) or Non-Alcoholic Steatohepatitis (NASH) in a subject comprising administering to the subject a therapeutically effective amount of a nucleotide sequence encoding a variant IL-10 molecule.

98. A method according to any of the preceding embodiments, wherein the nucleotide sequence is DNA, RNA, or modified variants thereof.

99. A method according to any of the preceding embodiments, wherein the nucleotide sequence is a mRNA or a modified mRNA linked to a nucleoside.

100. A method according to any of the preceding embodiments, wherein the nucleotide sequence is capable of in vivo expressing the variant IL-10 molecule within a cell, tissue, or organism.

101. A method according to any of the preceding embodiments, wherein the nucleotide sequence is delivered to a cell, tissue, or organism by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer.

102. A fusion protein comprising a monomeric IL-10 molecule or a variant thereof linked to two variable regions from at least two different antibodies, wherein the two variable regions are configured as a heavy chain variable (VH) region from a first antibody linked to a light chain variable (VL) region from a second antibody or a VL from the first antibody linked to a VH from the second antibody.

103. A fusion protein according to any of the preceding embodiments, wherein the monomeric IL-10 molecule or a variant thereof includes at least one amino acid substitution that increases or decreases affinity to an IL-10 receptor.

104. A fusion protein according to any of the preceding embodiments, wherein the monomeric IL-10 molecule or a variant thereof includes at least one amino acid substitution that increases affinity to an IL-10 receptor.

105. A fusion protein according to any of the preceding embodiments, wherein the monomeric IL-10 molecule or a variant thereof is an Epstein Barr virus (EBV) IL-10 homolog of SEQ ID No.: 3.

106. A fusion protein according to any of the preceding embodiments, wherein the EBV IL-10 homolog includes an amino acid substitution at position 31, 75, or both.

107. A fusion protein according to any of the preceding embodiments, wherein the EBV-IL-10 homolog includes an amino acid substitution at position 31.

108. A fusion protein according to any of the preceding embodiments, wherein the EBV-IL-10 homolog includes an amino acid substitution at position 75.

109. A fusion protein according to any of the preceding embodiments, wherein the EBV-IL-10 homolog includes an amino acid substitution at positions 31 and 75.

110. A fusion protein according to any of the preceding embodiments, wherein the EBV-IL-10 homolog includes an V31L amino acid substitution.

111. A fusion protein according to any, of the preceding embodiments, wherein the EBV-IL-10 homolog includes an A75I amino acid substitution.

112. A fusion protein according to any of the preceding embodiments, wherein the EBV-IL-10 homolog includes an V31L and A75I amino acid substitution.

113. A fusion protein according to any of the preceding embodiments, wherein the VH region of the first antibody is from an anti-HIV monoclonal antibody and the VL region of the second antibody is from an anti-ebola monoclonal antibody.

114. A fusion protein according to any of the preceding embodiments, wherein the VH region of the first antibody is from an anti-ebola monoclonal antibody and the VL region of the second antibody is from an anti-HIV monoclonal antibody.

115. A fusion protein according to any of the preceding embodiments, wherein the fusion protein is an amino acid sequence selected from SEQ ID Nos.: 24-28, 29, 33-51, 61, 63, 65, or 67.

116. A fusion protein according to any of the preceding embodiments, wherein the fusion protein is a diabody.

117. A fusion protein according to any of the preceding embodiments, wherein the fusion protein comprises a configuration selected from: (a) a VH region of the first antibody linked at its carboxy terminal end to an amino terminal end of a VL region of the second antibody subsequently linked to an amino terminal end of a monomer of IL-10 or a variant thereof; or (b) an IL-10 molecule or a variant thereof linked at its carboxy terminal end to an amino terminal end of a VH region of the second antibody subsequently linked to an amino terminal end of a VL region of the first antibody.

118. A fusion protein according to any of the preceding embodiments, wherein configuration (a) and (b) together form a diabody complex.

119. A fusion protein according to any of the preceding embodiments, further comprising a linker between the VH region and the VL region.

120. A fusion protein according to any of the preceding embodiments, wherein the amino acid sequence is selected from SEQ ID Nos: 24-28, 29, 33-53, 61, 63, 65, 67.

121. A fusion protein according to any of the preceding embodiments, wherein the first and second antibodies comprises one or more amino acid substitutions that reduce antigenicity in a subject.

122. An immunoconjugate complex comprising i) a first fusion protein comprising at its amino terminal end a heavy chain variable region (VH) of a first antibody linked to a light chain variable region (VL) of a second antibody further linked to a monomer of IL-10 or variant thereof; and ii) a second fusion protein comprising at its amino-terminal end a monomer of IL-10 or variant thereof linked to a VH of the second antibody further linked to a VL of the first antibody, wherein the VH and VL of the first and second antibodies associate into a diabody and the monomers of IL-10 form a functional dimeric IL-10 molecule.

123. An immunoconjugate complex according to any of the preceding embodiments, wherein the monomer of IL-10 includes at least one amino acid substitution that increases or decreases affinity to an IL-10 receptor.

124. An immunoconjugate complex according to any of the preceding embodiments, wherein the IL-10 molecule includes at least one amino acid substitution that increases affinity to an IL-10 receptor.

125. An immunoconjugate complex according to any of the preceding embodiments, wherein the monomer of IL-10 is an Epstein Barr virus (EBV) IL-10 homolog of SEQ ID No. 3.

126. An immunoconjugate complex according to any of the preceding embodiments, wherein the EBV IL-10 homolog includes an amino acid substitution at position 31, 75, or both.

127. An immunoconjugate complex according to any of the preceding embodiments, wherein the EBV-IL-10 homolog includes an amino acid substitution at position 31.

128. An immunoconjugate complex according to any of the preceding embodiments, wherein the EBV-IL-10 homolog includes an amino acid substitution at position 75.

129. An immunoconjugate complex according to any of the preceding embodiments, wherein the EBV-IL-10 homolog includes an amino acid substitution at positions 31 and 75.

130. An immunoconjugate complex according to any of the preceding embodiments, wherein the EBV-IL-10 homolog includes an V31L amino acid substitution.

131. An immunoconjugate complex according to any of the preceding embodiments, wherein the EBV-IL-10 homolog includes an A75I amino acid substitution.

132. An immunoconjugate complex according to any of the preceding embodiments, wherein the EBV-IL-10 homolog includes an V31L and A75I amino acid substitution.

133. An immunoconjugate complex according to any of the preceding embodiments, wherein the first antibody is from an anti-HIV monoclonal antibody and the second antibody is from an anti-ebola monoclonal antibody.

134. An immunoconjugate complex according to any of the preceding embodiments, wherein the first fusion protein is an amino acid sequence selected from SEQ ID Nos.: 24, 26, 28, 35, 38, 41, 46, 48, or 50.

135. An immunoconjugate complex according to any of the preceding embodiments, wherein the second fusion protein is an amino acid sequence selected from SEQ ID Nos.: 25, 27, 29, 36, 39, 42, 47, 49, or 51.

136. An immunoconjugate complex according to any of the preceding embodiments, further comprising a linker between the VH regions and the VL regions.

137. An immunoconjugate complex according to any of the preceding embodiments, wherein the monomer of IL-10 in the first fusion protein is linked to the VL region by its amino terminal end.

138. An immunoconjugate complex according to any of the preceding embodiments, wherein the monomer of IL-10 in the second fusion protein is linked to the VH region by its carboxy terminal end.

139. An immunoconjugate complex according to any of the preceding embodiments, wherein the first and second antibodies comprises one or more amino acid substitutions that reduce antigenicity in a subject.

140. A diabody comprising a first peptide chain comprising a heavy chain variable region (VH) from a first antibody, a light chain variable region (VL) from a second antibody, and a monomeric IL-10; and a second peptide chain comprising a VH and a VL from a second antibody and a monomeric IL-10 molecule, wherein the VH region of the first antibody associates with the VL region of first antibody and the VH region of the second antibody associates with the VL region of second antibody thereby allowing the monomeric IL-10 molecules on each peptide chain to form a functional IL-10 dimer.

141. A diabody according to any of the preceding embodiments, wherein the monomeric IL-10 includes at least one amino acid substitution that increases or decreases affinity to an IL-10 receptor.

142. A diabody according to any of the preceding embodiments, wherein the monomeric IL-10 molecule includes at least one amino acid substitution that increases affinity to an IL-10 receptor.

143. A diabody according to any of the preceding embodiments, wherein the monomeric IL-10 molecule is an Epstein Barr virus (EBV) IL-10 homolog of SEQ ID No. 3.

144. A diabody according to any of the preceding embodiments, wherein the EBV IL-10 homolog includes an amino acid substitution at position 31, 75, or both.

145. A diabody according to any of the preceding embodiments, wherein the EBV-IL-10 homolog includes an amino acid substitution at position 31.

146. A diabody according to any of the preceding embodiments, wherein the EBV-IL-10 homolog includes an amino acid substitution at position 75.

147. A diabody according to any of the preceding embodiments, wherein the EBV-IL-10 homolog includes an amino acid substitution at positions 31 and 75.

148. A diabody according to any of the preceding embodiments, wherein the EBV-IL-10 homolog includes an V31L amino acid substitution.

149. A diabody according to any of the preceding embodiments, wherein the EBV-IL-10 homolog includes an A75I amino acid substitution.

150. A diabody according to any of the preceding embodiments, wherein the EBV-IL-10 homolog includes an V31L and A75I amino acid substitution.

151. A diabody according to any of the preceding embodiments, wherein the first antibody is from an anti-HIV monoclonal antibody and the second antibody is from an anti-ebola monoclonal antibody.

152. A diabody according to any of the preceding embodiments, wherein the first peptide chain is an amino acid sequence selected from SEQ ID Nos.: 24, 26, 28, 35, 38, 41, 46, 48, or 50.

153. A diabody according to any of the preceding embodiments, wherein the second peptide chain is an amino acid sequence selected from SEQ ID Nos.: 25, 27, 29, 36, 39, 42, 47, 49, or 51.

154. A diabody according to any of the preceding embodiments, further comprising a linker between the VH regions and the VL regions.

155. A diabody according to any of the preceding embodiments, wherein the first and second antibodies comprises one or more amino acid substitutions that reduce antigenicity in a subject.

156. A diabody according to any of the preceding embodiments, wherein the monomer of IL-10 is linked to the first and second peptide chain by its carboxy terminal end.

157. A diabody according to any of the preceding embodiments, wherein the first and second antibodies comprises one or more amino acid substitutions that reduce antigenicity in a subject.

158. An immunoconjugate complex comprising i) a first fusion protein comprising at its amino terminal end a heavy chain variable (VH) region of a first antibody and a monomeric IL-10 molecule linked to by its amino terminal end; and ii) a second fusion protein comprising at its amino terminal end a monomer of IL-1 linked to a light chain variable region (VL) of the first antibody, wherein the VH region of the first antibody associates with the VL region of first antibody thereby allowing the monomeric IL-10 molecules on each peptide chain to form a functional IL-10 dimer.

159. An immunoconjugate complex according to any of the preceding embodiments, wherein the monomer of IL-10 includes at least one amino acid substitution that increases or decreases affinity to an IL-10 receptor.

160. An immunoconjugate complex according to any of the preceding embodiments, wherein the IL-10 molecule includes at least one amino acid substitution that increases affinity to an IL-10 receptor.

161. An immunoconjugate complex according to any of the preceding embodiments, wherein the monomer of IL-10 is an Epstein Barr virus (EBV) IL-10 homolog of SEQ ID No. 3.

162. An immunoconjugate complex according to any of the preceding embodiments, wherein the EBV IL-10 homolog includes an amino acid substitution at position 31, 75, or both.

163. An immunoconjugate complex according to any of the preceding embodiments, wherein the EBV-IL-10 homolog includes an amino acid substitution at position 31.

164. An immunoconjugate complex according to any of the preceding embodiments, wherein the EBV-IL-10 homolog includes an amino acid substitution at position 75

165. An immunoconjugate complex according to any of the preceding embodiments, wherein the EBV-IL-10 homolog includes an amino acid substitution at positions 31 and 75.

166. An immunoconjugate complex according to any of the preceding embodiments, wherein the EBV-IL-10 homolog includes an V31L amino acid substitution.

167. An immunoconjugate complex according to any of the preceding embodiments, wherein the EBV-IL-10 homolog includes an A75I amino acid substitution.

168. An immunoconjugate complex according to any of the preceding embodiments, wherein the EBV-IL-10 homolog includes an V31L and A75I amino acid substitution.

169. An immunoconjugate complex according to any of the preceding embodiments, wherein the VH and VL regions of the first antibody are from an anti-epidermal growth factor receptor (EGFR) monoclonal antibody.

170. An immunoconjugate complex according to any of the preceding embodiments, wherein the first fusion protein further comprises a VL region from a second antibody linking the VH region of the first antibody to the monomeric IL-10 and wherein the second fusion protein further comprises a VH region from the second antibody linking the monomeric IL-10 to the VL region.

171. An immunoconjugate complex according to any of the preceding embodiments, wherein the VH and VL regions of the second antibody are from an anti-Ebola monoclonal antibody.

172. An immunoconjugate complex according to any of the preceding embodiments, wherein the variable regions are linked to the monomers of IL-10 through linkers.

173. An immunoconjugate complex according to any of the preceding embodiments, wherein the first and second antibodies comprises one or more amino acid substitutions that reduce antigenicity in a subject.

174. An immunoconjugate complex according to any of the preceding embodiments, wherein the first and second antibodies comprises one or more amino acid substitutions that reduce antigenicity in a subject.

175. A fusion protein comprising variable light (VL) and variable heavy (VH) regions of a first antibody fused to monomers of IL-10, wherein the IL-10 monomers are directly linked to one another.

176. A fusion protein according to any of the preceding embodiments, wherein the IL-10 monomers are linked from a carboxy terminal end of a first IL-10 monomer to an amino terminal end of a second IL-10 monomer.

177. A fusion protein according to any of the preceding embodiments, wherein the fusion protein comprises the following configuration in amino to carboxy terminal fashion: the VL region of the first antibody is linked to a first IL-10 monomer, linked to a second IL-10 monomer, linked to the VH region of the first antibody.

178. A fusion protein according to any of the preceding embodiments, further comprising a VH region of a second antibody linked to the amino terminal end of the VL region of the first antibody and a VL region of a second antibody linked to the carboxy terminal end of the VH region of the first antibody.

179. A fusion protein according to any of the preceding embodiments, wherein the IL-10 monomers each include at least one amino acid substitution that increases or decreases affinity to an IL-10 receptor.

180. A fusion protein according to any of the preceding embodiments, wherein the IL-10 monomers each include at least one amino acid substitution that increases affinity to an IL-10 receptor.

181. A fusion protein according to any of the preceding embodiments, wherein the IL-10 monomer is an Epstein Barr virus (EBV) IL-10 homolog of SEQ ID No.: 3.

182. A fusion protein according to embodiment 181, wherein the EBV IL-10 homolog includes an amino acid substitution at position 31, 75, or both.

183. A fusion protein according to any of the preceding embodiments, wherein the EBV-IL-10 homolog includes an amino acid substitution at position 31.

184. A fusion protein according to any of the preceding embodiments, wherein the EBV-IL-10 homolog includes an amino acid substitution at position 75.

185. A fusion protein according to any of the preceding embodiments, wherein the EBV-IL-10 homolog includes an V31L amino acid substitution.

186. A fusion protein according to any of the preceding embodiments, wherein the EBV-IL-10 homolog includes an A75I amino acid substitution.

187. A fusion protein according to any of the preceding embodiments, wherein the first antibody is an anti-Ebola monoclonal antibody.

188. A fusion protein according to any of the preceding embodiments, wherein the first antibody is an anti-epidermal growth factor receptor (EGFR) monoclonal antibody.

189. A fusion protein according to any of the preceding embodiments, wherein the first antibody is an anti-Ebola monoclonal antibody and the second antibody is an anti-EGFR monoclonal antibody.

190. A method of treating a disease, disorder, or condition in a patient in need thereof, comprising administering to the patient a therapeutically effective amount of an Epstein Barr virus (EBV) IL-10 immunoconjugate complex, wherein the immunoconjugate complex has a molecular weight of about 60 to 155 kDa, wherein the therapeutically effective amount is in the range of about 0.5 microgram/kilogram to 100 micrograms/kilogram, and wherein the EBV IL-10 portion of the immunoconjugate is derived from SEQ ID No.: 3.

191. A method according to any of the preceding embodiments, wherein the immunoconjugate complex is administered monthly, bimonthly, weekly, twice a week, three times a week, or daily.

192. A method according to any of the preceding embodiments, wherein the variant EBV IL-10 is a variant comprising at least one amino acid substitution that increases or decreases binding to the IL-10 receptor 193. A method according to any of the preceding embodiments, wherein the variant EBV IL-10 comprises an amino acid substitution at positions 31, 75 or both of SEQ ID No.: 3.

194. A method according to any of the preceding embodiments, wherein the variant EBV IL-10 comprises an V31L amino acid substitution.

195. A method according to any of the preceding embodiments, wherein the EBV IL-10 comprises an A75I amino acid substitution.

196. A method according to any of the preceding embodiments, wherein the EBV IL-10 comprises V31L and A75I amino acid substitutions.

197. A method according to any of the preceding embodiments, wherein the immunoconjugate complex is a complex of two fusion proteins.

198. A method according to any of the preceding embodiments, wherein the immunoconjugate complex comprises i. a first fusion protein comprising at its amino-terminal end a heavy chain variable region (VH) of a first antibody linked to a light chain variable region (VL) of a second antibody further linked to a carboxy terminal end of a monomer of EBV IL-10; and ii. a second fusion protein comprising at its amino-terminal end a monomer of EBV IL-10 linked to a VH of the second antibody further linked to a VL of the first antibody, wherein the VHs and VLs of the first and second antibodies associate into a diabody and the monomers of EBV IL-10 form a functional dimeric EBV IL-10 molecule.

199. A method according to any of the preceding embodiments, wherein the first antibody and second antibody are different antibodies.

200. A method according to any of the preceding embodiments, wherein the first antibody is an anti-HIV monoclonal antibody and the second antibody is an anti-ebola monoclonal antibody.

201, A method according to any of the preceding embodiments, wherein the fusion protein is an amino acid sequence selected from SEQ ID Nos: 24-51.

202. A method according to any of the preceding embodiments, wherein the first fusion protein is an amino acid sequence selected from SEQ ID Nos.: 24, 26, 28, 35, 38, 41, 46, 48, or 50.

203. A method according to any of the preceding embodiments, wherein the second fusion protein is an amino acid sequence selected from SEQ ID Nos.: 25, 27, 29, 36, 39, 42, 47, 49, or 51.

204. A method according to any of the preceding embodiments, wherein the immunoconjugate complex is a diabody comprising EBV IL-10 monomers fused on either terminal ends, wherein the EBV IL-10 monomers are capable of associating into a functional EBV IL-10 dimer.

205. A method according to any of the preceding embodiments, wherein the disease, disorder, or condition is selected from cancer, inflammatory disease, autoimmune disease, or cholesterol.

206. A method according to any of the preceding embodiments, wherein the EBV IL-10 immunoconjugate complex is administered in an amount sufficient to a maintain steady IL-10 serum concentration based on administering at least every 2 to 3 days.

207. A method according to any of the preceding embodiments, wherein the immunoconjugate is capable of suppressing TNFα secretion and inducing IFNγ production at similar concentrations to wild type IL-10.

208. A method according to any of the preceding embodiments, wherein the EBV IL-10 immunoconjugate complex has similar activity to wild-type IL-10.

209. A method according to any of the preceding embodiments, wherein the immunoconjugate complex comprises (a) VH region of the first antibody at the N-terminal end linked to a VL region of the second antibody linked to a carboxy terminus of an IL-10 molecule; and (b) an IL-10 molecule linked to a VH region of the second antibody linked to a VL region of the first antibody.

210. A method of treating cancer in a patient in need thereof comprising administering to the patient a diabody comprising a first peptide chain having a heavy chain variable region (VH) from a first antibody, a light chain variable region (VL) from a second antibody, and a monomeric IL-10 molecule; and a second peptide chain having a VH and a VL from a second antibody and a monomeric IL-10 molecule, wherein the VH region of the first antibody associates with the VL region of first antibody and the VH region of the second antibody associates with the VL region of second antibody thereby allowing the monomeric IL-10 molecules on each peptide chain to form a functional IL-10 dimer.

211. A method according to any of the preceding embodiments, wherein the monomeric IL-10 is an Epstein Barr virus (EBV) IL-10 homolog of SEQ ID No.: 3.

212. A method according to any of the preceding embodiments, wherein the EBV IL-10 includes an amino acid substitution at position 31 of SEQ ID No.: 3.

213. A method according to any of the preceding embodiments, wherein the EBV IL-10 includes an V31L amino acid substitution.

214. A method according to any of the preceding embodiments, wherein the VH region of the first antibody is from an anti-HIV monoclonal antibody and the VL region of the second antibody is from an anti-ebola monoclonal antibody.

215. A method according to any of the preceding embodiments, wherein the first peptide chain is an amino acid sequence selected from SEQ ID No.: 28, 35, 38, 46.

216. A method according to any of the preceding embodiments, wherein the second peptide chain is an amino acid sequence selected from SEQ ID Nos.: 29, 36, 39, 47.

217. A method according to any of the preceding embodiments, further comprising a linker between the VH regions and the VL regions.

218. A method according to any of the preceding embodiments, wherein VH and VL each comprise one or more amino acid substitutions that reduce antigenicity in the patient.

219. A method according to any of the preceding embodiments, wherein the first antibody is from an anti-HIV monoclonal antibody and the second antibody is from an anti-ebola monoclonal antibody.

220. A method according to any of the preceding embodiments, wherein the diabody is formed with two peptide chains with the following amino to carboxy terminus configurations: (a) a first peptide comprising a VH region of the first antibody linked to a VL region of the second antibody that is then linked to a amino terminus of an IL-0 monomer or variant thereof; and (b) a second peptide comprising an IL-10 monomer linked to a VH region of the second antibody that is then linked to a VL region of the first antibody.

221. A method of treating cholesterol in a patient in need thereof, comprising administering to the patient a cholesterol reducing amount of a diabody comprising a first peptide chain having a heavy chain variable region (VH) from a first antibody, a light chain variable region (VL) from a second antibody, and a monomeric IL-10; and a second peptide chain having a VH and a VL from a second antibody and a monomeric IL-10 molecule, wherein the VH region of the first antibody associates with the VL region of first antibody and the VH region of the second antibody associates with the VL region of second antibody thereby allowing the monomeric IL-10 molecules on each peptide chain to form a functional IL-10 dimer.

222. A method according to any of the preceding embodiments, wherein the monomeric IL-10 is an Epstein Barr virus (EBV) IL-10 homolog of SEQ ID No.: 3.

223. A method according to any of the preceding embodiments, wherein the EBV IL-10 includes an amino acid substitution at position 31 of SEQ ID No.: 3.

224. A method according to any of the preceding embodiments, wherein the EBV IL-10 includes an V31L amino acid substitution.

225. A method according to any of the preceding embodiments, wherein the VH region of the first antibody is from an anti-HIV monoclonal antibody and the VL region of the second antibody is from an anti-ebola monoclonal antibody.

226. A method according to any of the preceding embodiments, wherein the first peptide chain is an amino acid sequence selected from SEQ ID No.: 24 or 50.

227. A method according to any of the preceding embodiments, wherein the second peptide chain is an amino acid sequence selected from SEQ ID No.: 25 or 51.

228. A method according to any of the preceding embodiments, further comprising a linker between the VH regions and the VL regions.

229. A method according to any of the preceding embodiments, wherein VH and VL each comprise one or more amino acid substitutions that reduce antigenicity in the patient.

230. A method according to any of the preceding embodiments, wherein the first antibody is from an anti-HIV monoclonal antibody and the second antibody is from an anti-ebola monoclonal antibody.

231. A method according to any of the preceding embodiments, wherein the diabody is formed with two peptide chains with the following amino to carboxy terminus configurations:

(a) a first peptide comprising a VH region of the first antibody linked to a VL region of the second antibody that is then linked to a amino terminus of an IL-10 monomer or variant thereof; and (b) a second peptide comprising an IL-10 monomer or variant thereof linked to a VH region of the second antibody that is then linked to a VL region of the first antibody.

232. A method of treating nonalcoholic steatohepatitis (NASH) or nonalcoholic fatty liver disease (NAFLD) in a patient in need thereof, comprising administering to the patient an NASH or NAFLD amount of a diabody comprising a first peptide chain having a heavy chain variable region (VH) from a first antibody, a light chain variable region (VL) from a second antibody, and a monomeric IL-10; and a second peptide chain having a VH and a VL from a second antibody and a monomeric IL-10 molecule, wherein the VH region of the first antibody associates with the VL region of first antibody and the VH region of the second antibody associates with the VL region of second antibody thereby allowing the monomeric IL-10 molecules on each peptide chain to form a functional IL-10 dimer.

233. A method according to any of the preceding embodiments, wherein the monomeric IL-10 is an Epstein Barr virus (EBV) IL-10 homolog of SEQ ID No.: 3.

234. A method according to any of the preceding embodiments, wherein the EBV IL-10 includes an amino acid substitution at position 31 of SEQ ID No.: 3.

235. A method according to any of the preceding embodiments, wherein the EBV IL-10 includes an V31L amino acid substitution.

236. A method according to any of the preceding embodiments, wherein the VH region of the first antibody is from an anti-HIV monoclonal antibody and the VL region of the second antibody is from an anti-ebola monoclonal antibody.

237. A method according to any of the preceding embodiments, wherein the first peptide chain is an amino acid sequence selected from SEQ ID Nos.: 24 or 50.

238. A method according to any of the preceding embodiments, wherein the second peptide chain is an amino acid sequence selected from SEQ ID Nos.: 25 or 51.

239. A method according to any of the preceding embodiments, further comprising a linker between the VH regions and the VL regions.

240. A method according to any of the preceding embodiments, wherein VH and VL each comprise one or more amino acid substitutions that reduce antigenicity in the patient.

241. A method according to any of the preceding embodiments, wherein the first antibody is from an anti-HIV monoclonal antibody and the second antibody is from an anti-ebola monoclonal antibody.

242. A method of treating inflammation in a patient in need thereof, comprising administering to the patient an anti-inflammatory amount of a diabody comprising a first peptide chain having a heavy chain variable region (VH) from a first antibody, a light chain variable region (VL) from a second antibody, and a monomeric IL-10; and a second peptide chain having a VH and a VL from a second antibody and a monomeric IL-10 molecule, wherein the VH region of the first antibody associates with the VL region of first antibody and the VH region of the second antibody associates with the VL region of second antibody thereby allowing the monomeric IL-10 molecules on each peptide chain to form a functional IL-10 dimer.

243. A method according to any of the preceding embodiments, wherein the monomeric IL-10 is an Epstein Barr virus (EBV) IL-10 homolog of SEQ ID No.: 3.

244. A method according to any of the preceding embodiments, wherein the EBV IL-10 includes an amino acid substitution at position 75 of SEQ ID No.: 3.

245. A method according to any of the preceding embodiments, wherein the EBV IL-10 includes an V31L amino acid substitution.

246. A method according to any of the preceding embodiments, wherein the VH region of the first antibody is from an anti-HIV monoclonal antibody and the VL region of the second antibody is from an anti-ebola monoclonal antibody.

247. A method according to any of the preceding embodiments, wherein the first peptide chain is an amino acid sequence selected from SEQ ID Nos.: 26, 41, or 48.

248. A method according to any of the preceding embodiments, wherein the second peptide chain is an amino acid sequence selected from SEQ ID Nos.: 27, 42, 49.

249. A method according to any of the preceding embodiments, further comprising a linker between the VH regions and the VL regions.

250. A method according to any of the preceding embodiments, wherein VH and VL each comprise one or more amino acid substitutions that reduce antigenicity in the patient.

251. A method according to any of the preceding embodiments, wherein the first antibody is from an anti-HIV monoclonal antibody and the second antibody is from an anti-ebola monoclonal antibody.

252. A fusion protein of formula (I-VII)

IL10-$L^1$-$X^1$-$L^1$-$X^2$-$L^1$-IL10 (Formula I); $(Z)_n$-$X^1$-$L^2$-$Y^2$-$L^1$-IL10 (Formula II); IL10-$L^1$-$Y^1$-$L^2$-$X^2$-$(Z)_n$ (Formula III); $X^1$-$L^2$-$X^2$-$L^1$-IL10 (Formula IV); IL10-$L^1$-$X^1$-$L^2$-$X^2$ (Formula V); $X^1$-$L^1$-IL10 (Formula VI); IL10-$L^1$-X2 (Formula VII); or any combination thereof, wherein "IL-10" is a monomer sequence selected from SEQ ID Nos: 1, 3, 14, 18, 15, 19, 16 20, 55, 57, or 59; more preferably the "IL-10" consists of SEQ ID No: 55, 57, or 59;

"$L^1$" is a linker of SEQ ID No: 31 or 54;

"$L^2$" is a linker of SEQ ID No: 30;

"$X^1$" is a VH region obtained from a first antibody specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; SR-J1; HIV, or Ebola;

"$X_2$" is a VL region obtained from the same antibody as $X_1$;

"$Y_1$" is VH region obtained from a second antibody specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; SR-J1; HIV, or Ebola;

"$Y_2$" is a VL region obtained from the same antibody as $Y_1$;

wherein X and Y are obtained from the same or different antibody;

"Z" is a cytokine selected from IL-10, IL-10 variant molecule IL-6, IL-4, IL-1, IL-2, IL-3, IL-5, IL-7, IL-8, IL-9, IL-15, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-1, or IL-13;

"n" is an integer selected from 0-2.

253. The fusion protein according to the preceding embodiment, wherein formula II and III are capable of forming a fusion protein complex where the IL-10 monomer from each of formula II and III are capable of forming a functional homodimeric IL-10 or variant-thereof.

254. The fusion protein according to any of the preceding embodiments, wherein formula II is SEQ ID Nos: 24, 26, 28, 41, 48, or 0.

255. The fusion protein according to any of the preceding embodiments, wherein formula III is SEQ ID Nos: 25, 27, 29, 42, 49, or 51.

256. The fusion protein according to any of the preceding embodiments, wherein the fusion protein complex is formed between SEQ ID Nos: 24 and 25; 26 and 27, 28 and 29; 41 and 42; 48 and 49; or 50 and 51.

257. The fusion protein according to any of the preceding embodiments, wherein formula IV and V are capable of forming a fusion protein complex where the IL-10 monomer from each of formula IV and V are capable of forming a functional homodimeric IL-10 or variant thereof.

258. The fusion protein according to any of the preceding embodiments, wherein formula IV is SEQ ID Nos: 35, 38, 46, 48, or 50.

259. The fusion protein according to any of the preceding embodiments, wherein formula V is SEQ ID Nos: 36, 39, 47, 49, or 51.

260. The fusion protein according to any of the preceding embodiments, wherein the fusion protein complex is formed between SEQ ID Nos: 35 and 36; 38 and 39, 46 and 47; 48 and 49; or 50 and 51.

261. The fusion protein according to any of the preceding embodiments, wherein formula VI and VII are capable of forming a fusion protein complex where the IL-10 monomer from each of formula VI and VII are capable of forming a functional homodimeric IL-10 or variant thereof.

262. The fusion protein according to any of the preceding embodiments, wherein formula I is SEQ ID Nos: 33-34, 40, 43-44, 45, 52 53, 61, 63, 65, or 67.

263. The fusion protein according to any of the preceding embodiments, wherein "n" 1 and Z is IL-2, Il-7, IL-12, IL-15 or any combination thereof.

264. The fusion protein according to any of the preceding embodiments, wherein Z is conjugated onto the N-terminal end of $X^1$, $Y^1$, or both.

265. A method of treating cancer comprising administering to a patient in need thereof a composition comprising a fusion protein according to according to any of the preceding embodiments.

266. The method according to any of the preceding embodiments, wherein the fusion protein is SEQ ID Nos: 28-29, 35-36, 38-39, 46-47, 52 53, 61, 63, 65, or 67.

267. The method according to any of the preceding embodiments, wherein the fusion protein forms a protein complex and the protein complex is formed between SEQ ID Nos: 28 and 29; 35 and 36; 38 and 39; or 46 and 47.

268. The method according to any of the preceding embodiments, wherein the composition comprises a fusion protein of SEQ ID Nos: 33, 34, 44, 52 or 53, 61, 63, 65, or 67.

269. The method according to any of the preceding embodiments, wherein the fusion protein comprises an IL-10 consisting of DV07 of SEQ ID No. 59.

270. A method of treating inflammatory disease comprising administering to a patient in need thereof a composition comprising a fusion protein according to any of the preceding embodiments.

271. The method according to any of the preceding embodiments, wherein the fusion protein is SEQ ID Nos: 26-27, 41-42, 48, or 49.

272. The method according to any of the preceding embodiments, wherein the fusion protein forms a protein complex and the protein complex is formed between SEQ ID Nos: 26 and 27; 41 and 42; 48 and 49.

273. The method according to any of the preceding embodiments, wherein the composition comprises a fusion protein of SEQ ID Nos: 37, 40, or 43.

274. The method according to any of the preceding embodiments, wherein the fusion protein comprises an IL-10 consisting of DV06 of SEQ ID No. 57.

275. A method of treating a lipid based disease comprising administering to a patient in need thereof a composition comprising a fusion protein according to any of the preceding embodiments.

276. The method according to any of the preceding embodiments, wherein the fusion protein is SEQ ID Nos: 24-25, 50 or 51.

277. The method according to any of the preceding embodiments, wherein the fusion protein forms a protein complex and the protein complex is formed between SEQ ID Nos: 24 and 25; and 50 and 51.

278. The method according to any of the preceding embodiments, wherein the composition comprises a fusion protein of SEQ ID No: 45.

REFERENCES

Asadullah, K. (1999). Interleukin 10 treatment of psoriasis: clinical results of a phase 2 trial. Archives Dermatology, 187-192.

Berman, R. M. (1996). Systemic Administration of Cellular IL-10 Induces an Effective Specific and Long-lived Immune Response Against Established Tumors in Mice. Journal of Immunology, 231-238.

Blum, A. M. (2003). CD4+ T cells from IL-10-deficient mice transfer susceptibility to NSAID-induced Rag colitis. American Journal of Physiology, G320-G325.

Chan, I. H. (2015). The Potentiation of IFNg and Induction of Cytotoxic Proteins by Pegylated IL-10 in Human CD8 T cells. Journal of Interferon and Cytokine Research.

Chan, I. H. (2016). PEG-rIL-10 treatment decreases FoxP3+T regs despite upregulation of intratumoral IDO OncoImmunology.

Chan, I. H. (2016). PEGylated IL-10 Activates Kupffer Cells to Control Hypercholesterolemia. PLOS One.

Chernoff, A. E. (1995). A randomized, controlled trial of IL-10 in humans. Inhibition of inflammatory cytokine production and immune responses. Journal of Immunology, 5492-5499.

Conaway, E. A. (2017). Inhibition of Inflammatory Gene Transcription by IL-10 is Associated with Rapid Suppression of Lipopolysaccharide Induced Enhancer Activation. Journal of Immunology.

Correa, I. (2009). Defective IL-10 production in severe phenotypes of Crohn's disease. Journal of Leukocyte Biology, 896-903.

Correa, I. (2009). Defective IL-10 production in severe phenotypes of Crohn's disease. Journal of Leukocyte Biology.

Emmerich, J. (2012). IL-10 directly activates and expands tumor resident $CD8^+$ T cells without de novo infiltration from secondary lymphoid organs. Cancer Research.

Fedorak, R. N. (2000). Recombinant Human Interleukin 10 in the Treatment of Patients With Mild to Moderately Active Crohn's DIsease. Gastroenterology, 1473-1482.

Friedrich, M. (2002). Immunomodulation by Interleukin-10 Therapy Decreases the Incidence of Relapse and Prolongs the Relapse-free Interval in Psoriasis. Journal of Investigative Dermatology; 672-677.

Fujii, S.-i. (2001). Interleukin 10 promotes the maintenance of antitumor $CD8^+$ T cell effector function in situ. Blood, 2143-2151.

Ghosh, S. (2006). Interferring with interferons in inflammatory bowel disease. Gut.

Hsu, D.-H. (1990). Expression of Interleukin-10 Activity by Epstein-Barr Virus Protein BCRF1. Science, 830-832.

Jones, B. C. (2002). Crystal structure of human cytomegalovirus IL-10 bound to soluble human IL-10R1. PNAS, 9404-9409.

Kennedy Norton (2008). IL-10 Suppresses Mast Cell IgE Receptor Expression and Signaling In Vitro and In Vivo. Journal of Immunology, 2848-2854.

Kimple et al (2013). Overview of Affinity Tags for Protein Purification. Curr. Protoc. Protein Sci., 73:Unit 9.9

Kuhn, R. (1993). Interleukin-10 Deficient Mice Develop Chronic Enterocolitis. Cell, 263-274.

Kundu, N. (1997). Interleukin 10 Inhibits Tumor Metastasis Downregulates MHC Class I and Enhances NK Lysis. Cellular Immunology, 55-61.

Lauw, F. N. (2000). Proinflammatory Effects of IL-10 During Human Endotoxemia. Journal of Immunology, 2783-2789.

Leach, M. W. (1999). The Role of IL-10 in Inflammatory Bowel DIsease: "Of Mice and Men". Toxicilogic Pathology, 123-133.

Liu, Y. (1997). The EBV IL-10 homologue is a selective agonist with impaired binding to the IL-10 receptor. Journal of Immunology, 604-613.

Maini, R. N. (1997). rHuIL-10 in subjects with active rheumatoid arthritis (RA): A phase I and cytokine response study. Arthritis Rheumatology, 40.

Malefyt, R. d. (1991). Interleukin 10 Inhibits Cytokine Synthesis by Human Monocytes An Autoregulatory Role of IL-10 Produced by Monocytes. J. Exp. Med., 1209-1220.

Malefyt, R. d. (1993). Direct effects of IL-10 on subsets of human CD4 T cell clones and resting T cells—Specific inhibition of IL-2 production and proliferation. Journal of Immunology, 4754-4765.

Minter, R. M. (2001). Adenoviral Delivery of Human and Viral IL-10 in Murine Sepsis. Journal of Immunology, 1053-1-59.

Mumm, J. B. (2011). IL-10 Elicits IFNg Dependent Tumor Immune Surveillance. Cancer Cell, 781-796.

Naing, A. (2016). Safety, Antitumor Activity, and Immune Activation of Pegylated Recombinant Human Interleukin-10 (AM0010) in Patients With Advanced Solid Tumors. Journal of Clinical Oncology.

Naing, A. (2018). PEGylated IL-10 (Pegilodecakin) Induces Systemic Immune Activation, $CD8^+$ T Cell Invigoration and Polyclonal T Cell Expansion in Cancer Patients. Cancer Cell.

Ouyang, P. (2014). IL-10 encoded by viruses: a remarkable example of independent acquisition of a cellular gene by viruses and it's subsequent evolution in the viral genome. Journal of General Virology, 245-262.

Salek-Ardakani, S. (2002). Epstein-Barr Virus Encoded Interleukin-10 Inhibits HLA-Class I, ICAM-1, and B7 Expression on Human Monocytes: Implications for Immune Evasion by EBV. Virology, 342-351.

Sasaki, T. (1992). The role of interferon g in the pathogenesis of Crohn's disease. Gastroenterologia Japanica.

Schreiber, S. (2000). Safety and Efficacy of Recombinant Human Interleukin 10 in Chronic Active Crohn's Disease. Gastroenterology, 1461-1472.

Slobedman, B. (2009). Virus-Encoded Homologs of Cellular Interleukin-10 and Their Control of Host Immune Function. Journal of Virology, 9618-9629.

Strober, W. (2011). Pro-Inflammatory Cytokines in the Pathogenesis of IBD. Gastroenterology, 1756-1767.

Thompson-Snipes, L. (1991). Interleukin 10: A Novel Stimulatory Factor for Mast Cells and Their Progenitors. Journal of Experimental Medicine, 507-510.

Tilg, H. (2002). Treatment of Crohn's disease with recombinant human interleukin 10 induces the proinflammatory cytokine interferon gamma. Gut, 191-195.

Vieira, P. (1991). Isolation and expression of human cytokine synthesis inhibitory factor cDNA clones Homology to Epstein Barr virus open reading frame BCRF1. PNAS, 1172-1176.

Yoon, S. I. (2005). Same Structure Different Function Crystal Structure of the Epstein Barr Virus IL-10 Bound to the Soluble IL-10R1 Chain. Structure, 551-564.

Yoon, S. I. (2012). Epstein-Barr Virus IL-10 Engages IL-10R1 by a Two-step Mechanism Leading to Altered Signaling Properties. Journal of Biological Chemistry.

Zheng, L. (1996). Interleukin 10 Inhibits Tumor Metastasis Through an NK Cell-dependent Mechanism. Journal of Experimental Medicine, 579-584.

Zhu, L. (2017). IL-10 and IL-10 Receptor Mutations in Very Early Onset Inflammatory Bowel Disease. Gastroenterology Research, 65-69.

Zigmond, E. (2014). Macrophage-Restricted interleukin-10 Receptor Deficiency, but Not IL-10 Deficiency, Causes Severe Spontaneous Colitis. Cell.

The invention claimed is:

1. A fusion protein of formula (I, IV, V, VI, or, VII)

IL10-$L^1$-$X^1$-$L^1$-$X^2$-$L^1$-IL10 (Formula I);

$X^1$-$L^2$-$X^2$-$L^1$-IL10 (Formula IV);

IL10-$L^1$-$X^1$-$L^2$-$X^2$ (Formula V);

$X^1$-$L^1$-IL10 (Formula VI);

IL10-$L^1$-$X^2$ (Formula VII);

wherein

"IL-10" is a monomer sequence selected from SEQ ID Nos: 16 or 59;

"$L^1$" is a linker of SEQ ID No: 31 or 54;

"$L^2$" is a linker of SEQ ID No: 30;

"$X^1$" is a VH region obtained from a first antibody specific for epidermal growth factor receptor (EGFR); CD52; various immune check point targets, such as but not limited to PD-L1, PD-1, TIM3, BTLA, LAG3 or CTLA4; CD20; CD47; GD-2; HER2; EpCAM; ICAM (ICAM-1, -2, -3, -4, -5), VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; SR-J1; HIV, or Ebola;

"$X^2$" is a VL region obtained from the same antibody as $X^1$.

2. The fusion protein according to claim 1, wherein formula IV and V are capable of forming a fusion protein complex where the IL-10 monomer from each of formula IV and V are capable of forming a functional homodimer.

3. The fusion protein according to claim 2, wherein formula IV is SEQ ID Nos: 35, 38, or 46.

4. The fusion protein according to claim 2, wherein formula V is SEQ ID Nos: 36, 39, or 47.

5. The fusion protein according to claim 2, wherein the fusion protein complex is formed between SEQ ID Nos: 35 and 36; 38 and 39, r 46 and 47.

6. The fusion protein according to claim 1, wherein formula VI and VII are capable of forming a fusion protein complex where the IL-10 monomer from each of formula VI and VII are capable of forming a functional homodimer and wherein the VH region and VL region pair to form a scFv.

7. The fusion protein according to claim 1, wherein formula I is SEQ ID Nos: 33-34, 44, 52 or 53.

8. The fusion protein according to claim 1, wherein the VH region and the VL region are from an anti-Ebola antibody; and wherein the VH region and VL region comprise 6 CDR regions engrafted with 6 CDR regions from an antibody selected from EGFR; CD52; PD-L1; PD-1; TIM3; BTLA; LAG3; CTLA4; CD20; CD47; GD-2; HER2; EpCAM; ICAM-1; ICAM-2; ICAM-3; ICAM-4; ICAM-5; VCAM, FAPα; 5T4; Trop2; EDB-FN; TGFβ Trap; MadCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; or SR-J1.

9. The fusion protein according to claim 8, wherein the VH region and the VL region from the anti-Ebola antibody is engrafted with 6 CDR regions from an anti-EGFR antibody.

10. The fusion protein according to claim 1, wherein the VH region and the VL region comprise modifications that reduce the antigenicity in a subject.

11. A pharmaceutical composition comprising a therapeutically effective amount of the fusion protein according to claim 1, and a pharmaceutically acceptable carrier, excipient, preservative, stabilizers, or any combination thereof.

* * * * *

SEQUENCE LISTING

```
<160> NUMBER OF SEQ ID NOS: 68

<210> SEQ ID NO 1
<211> LENGTH: 178
<212> TYPE: PRT
<213> ORGANISM: Homo sapiens

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 2
<211> LENGTH: 1629
<212> TYPE: DNA
<213> ORGANISM: Homo sapiens

<400> SEQUENCE: 2

acacatcagg ggcttgctct tgcaaaacca aaccacaaga cagacttgca aaagaaggca      60

tgcacagctc agcactgctc tgttgcctgg tcctcctgac tggggtgagg gccagcccag     120

gccagggcac ccagtctgag aacagctgca cccacttccc aggcaacctg cctaacatgc     180

ttcgagatct ccgagatgcc ttcagcagag tgaagacttt ctttcaaatg aaggatcagc     240

tggacaactt gttgttaaag gagtccttgc tggaggactt taagggttac ctgggttgcc     300
```

```
aagccttgtc tgagatgatc cagttttacc tggaggaggt gatgccccaa gctgagaacc    360

aagacccaga catcaaggcg catgtgaact ccctggggga gaacctgaag accctcaggc    420

tgaggctacg gcgctgtcat cgatttcttc cctgtgaaaa caagagcaag gccgtggagc    480

aggtgaagaa tgcctttaat aagctccaag agaaaggcat ctacaaagcc atgagtgagt    540

ttgacatctt catcaactac atagaagcct acatgacaat gaagatacga aactgagaca    600

tcagggtggc gactctatag actctaggac ataaattaga ggtctccaaa atcggatctg    660

gggctctggg atagctgacc cagccccttg agaaacctta ttgtacctct cttatagaat    720

atttattacc tctgatacct caacccccat ttctatttat ttactgagct tctctgtgaa    780

cgatttagaa agaagcccaa tattataatt tttttcaata tttattattt tcacctgttt    840

ttaagctgtt tccatagggt gacacactat ggtatttgag tgttttaaga taaattataa    900

gttacataag ggaggaaaaa aaatgttctt tggggagcca acagaagctt ccattccaag    960

cctgaccacg ctttctagct gttgagctgt ttccctgac ctccctctaa tttatcttgt    1020

ctctgggctt ggggcttcct aactgctaca aatactctta ggaagagaaa ccagggagcc   1080

cctttgatga ttaattcacc ttccagtgtc tcggagggat tcccctaacc tcattcccca   1140

accacttcat tcttgaaagc tgtggccagc ttgttattta taacaaccta aatttggttc   1200

taggccgggc gcggtggctc acgcctgtaa tcccagcact ttgggaggct gaggcgggtg   1260

gatcacttga ggtcaggagt tcctaaccag cctggtcaac atggtgaaac cccgtctcta   1320

ctaaaaatac aaaaattagc cgggcatggt ggcgcgcacc tgtaatccca gctacttggg   1380

aggctgaggc aagagaattg cttgaaccca ggagatggaa gttgcagtga gctgatatca   1440

tgcccctgta ctccagcctg ggtgacagag caagactctg tctcaaaaaa taaaaataaa   1500

aataaatttg gttctaatag aactcagttt taactagaat ttattcaatt cctctgggaa   1560

tgttacattg tttgtctgtc ttcatagcag attttaattt tgaataaata aatgtatctt   1620

attcacatc                                                           1629
```

```
<210> SEQ ID NO 3
<211> LENGTH: 147
<212> TYPE: PRT
<213> ORGANISM: Human gammaherpesvirus 4

<400> SEQUENCE: 3

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125
```

```
Ser Glu Phe Asp Ile Phe Ile Asn Tyr Ile Glu Ala Tyr Met Thr Ile
    130                 135                 140

Lys Ala Arg
145


<210> SEQ ID NO 4
<211> LENGTH: 632
<212> TYPE: DNA
<213> ORGANISM: Human gammaherpesvirus 4

<400> SEQUENCE: 4

tataaatcac ttccctatct caggtaggcc tgcacacctt aggtatggag cgaaggttag      60

tggtcactct gcagtgcctg gtgctgcttt acctggcacc tgagtgtgga ggtacagacc     120

aatgtgacaa ttttccccaa atgttgaggg acctaagaga tgccttcagt cgtgttaaaa     180

cctttttcca gacaaaggac gaggtagata accttttgct caaggagtct ctgctagagg     240

actttaaggg ctaccttgga tgccaggccc tgtcagaaat gatccaattc tacctggagg     300

aagtcatgcc acaggctgaa aaccaggacc ctgaagccaa agaccatgtc aattctttgg     360

gtgaaaatct aaagacccta cggctccgcc tgcgcaggtg ccacaggttc ctgccgtgtg     420

agaacaagag taaagctgtg gaacagataa aaaatgcctt taacaagctg caggaaaaag     480

gaatttacaa agccatgagt gaatttgaca tttttattaa ctacatagaa gcatacatga     540

caattaaagc caggtgataa ttccataccc tggaagcagg agatgggtgc atttcacccc     600

aaccccccct ttcgactgtc atttacaata aa                                   632


<210> SEQ ID NO 5
<211> LENGTH: 177
<212> TYPE: PRT
<213> ORGANISM: Human betaherpesvirus 5

<400> SEQUENCE: 5

Met Leu Ser Val Met Val Ser Ser Ser Leu Val Leu Ile Val Phe Phe
1               5                   10                  15

Leu Gly Ala Ser Glu Glu Ala Lys Pro Ala Ala Thr Thr Thr Thr Ile
            20                  25                  30

Lys Asn Thr Lys Pro Gln Cys Arg Pro Glu Asp Tyr Ala Ser Arg Leu
        35                  40                  45

Gln Asp Leu Arg Val Thr Phe His Arg Val Lys Pro Thr Leu Gln Arg
    50                  55                  60

Glu Asp Asp Tyr Ser Val Trp Leu Asp Gly Thr Val Val Lys Gly Cys
65                  70                  75                  80

Trp Gly Cys Ser Val Met Asp Trp Leu Leu Arg Arg Tyr Leu Glu Ile
                85                  90                  95

Val Phe Pro Ala Gly Asp His Val Tyr Pro Gly Leu Lys Thr Glu Leu
            100                 105                 110

His Ser Met Arg Ser Thr Leu Glu Ser Ile Tyr Lys Asp Met Arg Gln
        115                 120                 125

Cys Pro Leu Leu Gly Cys Gly Asp Lys Ser Val Ile Ser Arg Leu Ser
    130                 135                 140

Gln Glu Ala Glu Arg Lys Ser Asp Asn Gly Thr Arg Lys Gly Leu Ser
145                 150                 155                 160

Glu Leu Asp Thr Leu Phe Ser Arg Leu Glu Glu Tyr Leu His Ser Arg
                165                 170                 175

Lys
```

<210> SEQ ID NO 6
<211> LENGTH: 693
<212> TYPE: DNA
<213> ORGANISM: Human betaherpesvirus 5

<400> SEQUENCE: 6
atgctgtcgg tgatggtctc ttcctctctg gtcctgatcg tctttttctt aggcgcttcc 60
gaggaggcga agccggcggc gacgacgacg acgataaaga atacaaagcc gcagtgtcgt 120
ccggaggatt acgcgagcag attgcaagat ctccgcgtca cctttcatcg agtaaaacct 180
acgttggtag gtcatgtagg tacggtttat tgcgacggtc tttcttttcc gcgtgtcggg 240
tgacgtagtt ttcctcttgt agcaacgtga ggacgactac tccgtgtggc tcgacggtac 300
ggtggtcaaa ggctgttggg gatgcagcgt catggactgg ttgttgaggc ggtatctgga 360
gatcgtgttc cccgcaggcg accacgtcta tcctggactt aagacggaat tgcatagtat 420
gcgctcgacg ctagaatcca tctacaaaga catgcggcaa tgcgtaagtg tctctgtggc 480
ggcgctgtcc gcgcagaggt aacaacgtgt tcatagcacg ctgttttact tttgtcgggc 540
tcccagcctc tgttaggttg cggagataag tccgtgatta gtcggctgtc tcaggaggcg 600
gaaaggaaat cggataacgg cacgcggaaa ggtctcagcg agttggacac gttgtttagc 660
cgtctcgaag agtatctgca ctcgagaaag tag 693

<210> SEQ ID NO 7
<211> LENGTH: 178
<212> TYPE: PRT
<213> ORGANISM: Mus musculus

<400> SEQUENCE: 7

Met Pro Gly Ser Ala Leu Leu Cys Cys Leu Leu Leu Leu Thr Gly Met
1 5 10 15

Arg Ile Ser Arg Gly Gln Tyr Ser Arg Glu Asp Asn Asn Cys Thr His
20 25 30

Phe Pro Val Gly Gln Ser His Met Leu Leu Glu Leu Arg Thr Ala Phe
35 40 45

Ser Gln Val Lys Thr Phe Phe Gln Thr Lys Asp Gln Leu Asp Asn Ile
50 55 60

Leu Leu Thr Asp Ser Leu Met Gln Asp Phe Lys Gly Tyr Leu Gly Cys
65 70 75 80

Gln Ala Leu Ser Glu Met Ile Gln Phe Tyr Leu Val Glu Val Met Pro
85 90 95

Gln Ala Glu Lys His Gly Pro Glu Ile Lys Glu His Leu Asn Ser Leu
100 105 110

Gly Glu Lys Leu Lys Thr Leu Arg Met Arg Leu Arg Arg Cys His Arg
115 120 125

Phe Leu Pro Cys Glu Asn Lys Ser Lys Ala Val Glu Gln Val Lys Ser
130 135 140

Asp Phe Asn Lys Leu Gln Asp Gln Gly Val Tyr Lys Ala Met Asn Glu
145 150 155 160

Phe Asp Ile Phe Ile Asn Cys Ile Glu Ala Tyr Met Met Ile Lys Met
165 170 175

Lys Ser

<210> SEQ ID NO 8
<211> LENGTH: 1314
<212> TYPE: DNA

<213> ORGANISM: Mus musculus

<400> SEQUENCE: 8

```
gggggggggg atttagagac ttgctcttgc actaccaaag ccacaaagca gccttgcaga      60
aaagagagct ccatcatgcc tggctcagca ctgctatgct gcctgctctt actgactggc     120
atgaggatca gcaggggcca gtacagccgg gaagacaata actgcaccca cttcccagtc     180
ggccagagcc acatgctcct agagctgcgg actgccttca gccaggtgaa gactttcttt     240
caaacaaagg accagctgga caacatactg ctaaccgact ccttaatgca ggactttaag     300
ggttacttgg gttgccaagc cttatcggaa atgatccagt tttacctggt agaagtgatg     360
ccccaggcag agaagcatgg cccagaaatc aaggagcatt tgaattccct gggtgagaag     420
ctgaagaccc tcaggatgcg gctgaggcgc tgtcatcgat ttctcccctg tgaaaataag     480
agcaaggcag tggagcaggt gaagagtgat tttaataagc tccaagacca aggtgtctac     540
aaggccatga atgaatttga catcttcatc aactgcatag aagcatacat gatgatcaaa     600
atgaaaagct aaaacacctg cagtgtgtat tgagtctgct ggactccagg acctagacag     660
agctctctaa atctgatcca gggatcttag ctaacggaaa caactccttg gaaaacctcg     720
tttgtacctc tctccgaaat atttattacc tctgatacct cagttcccat tctatttatt     780
cactgagctt ctctgtgaac tatttagaaa gaagcccaat attataattt tacagtattt     840
attattttta acctgtgttt aagctgtttc cattggggac actttatagt atttaaaggg     900
agattatatt atatgatggg aggggttctt ccttgggaag caattgaagc ttctattcta     960
aggctggcca cacttgagag ctgcagggcc ctttgctatg gtgtcctttc aattgctctc    1020
atccctgagt tcagagctcc taagagagtt gtgaagaaac tcatgggtct tgggaagaga    1080
aaccagggag atcctttgat gatcattcct gcagcagctc agagggttcc cctactgtca    1140
tcccccagcc gcttcatccc tgaaaactgt ggccagtttg ttatttataa ccacctaaaa    1200
ttagttctaa tagaactcat ttttaactag aagtaatgca attcctctgg gaatggtgta    1260
ttgtttgtct gcctttgtag cagcatctaa ttttgaataa atggatctta ttcg          1314
```

<210> SEQ ID NO 9
<211> LENGTH: 168
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Asp Glu Val Asp Asn Leu Leu Leu Lys Glu Ser Leu Leu Glu
    50                  55                  60

Asp Phe Lys Gly Tyr Leu Gly Cys Gln Ala Leu Ser Glu Met Ile Gln
65                  70                  75                  80

Phe Tyr Leu Glu Glu Val Met Pro Gln Ala Glu Asn Gln Asp Pro Glu
                85                  90                  95

Ala Lys Asp His Val Asn Ser Leu Gly Glu Asn Leu Lys Leu Arg Leu
            100                 105                 110
```

```
Arg Leu Arg Arg Cys His Arg Phe Leu Pro Cys Glu Asn Lys Ser Lys
        115                 120                 125

Ala Val Glu Gln Ile Lys Asn Ala Phe Asn Lys Leu Gln Glu Lys Gly
    130                 135                 140

Ile Tyr Lys Ala Met Ser Glu Phe Asp Ile Phe Ile Asn Tyr Ile Glu
145                 150                 155                 160

Ala Tyr Met Thr Ile Lys Ala Arg
                165


<210> SEQ ID NO 10
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
            100                 105                 110

Arg Leu Arg Leu Arg Gln Cys Pro Leu Leu Gly Cys Gly Asp Lys Ala
        115                 120                 125

Val Glu Gln Ile Lys Asn Ala Phe Asn Lys Leu Gln Glu Lys Gly Ile
    130                 135                 140

Tyr Lys Ala Met Ser Glu Phe Asp Ile Phe Ile Asn Tyr Ile Glu Ala
145                 150                 155                 160

Tyr Met Thr Ile Lys Ala Arg
                165


<210> SEQ ID NO 11
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Leu Asp Asn Leu Leu Leu Lys Glu Ser Leu Leu
    50                  55                  60
```

Glu Asp Phe Lys Gly Tyr Leu Gly Cys Gln Ala Leu Ser Glu Met Ile
65 70 75 80

Gln Phe Tyr Leu Glu Glu Val Met Pro Gln Ala Glu Asn Gln Asp Pro
85 90 95

Glu Ala Lys Asp His Val Asn Ser Leu Gly Glu Asn Leu Lys Thr Leu
100 105 110

Arg Leu Arg Leu Arg Gln Cys Pro Leu Leu Gly Cys Gly Asp Lys Ala
115 120 125

Val Glu Gln Ile Lys Asn Ala Phe Asn Lys Leu Gln Glu Lys Gly Ile
130 135 140

Tyr Lys Ala Met Ser Glu Phe Asp Ile Phe Ile Asn Tyr Ile Glu Ala
145 150 155 160

Tyr Met Thr Ile Lys Ala Arg
165

<210> SEQ ID NO 12
<211> LENGTH: 167
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

Met Asp Met Arg Val Pro Ala Gln Leu Leu Gly Leu Leu Leu Leu Trp
1 5 10 15

Leu Arg Gly Ala Arg Cys Gly Thr Asp Gln Cys Asp Asn Phe Pro Gln
20 25 30

Met Leu Arg Asp Leu Arg Asp Ala Phe Ser Arg Val Lys Thr Phe Phe
35 40 45

Gln Thr Lys Asp Glu Val Asp Asn Leu Leu Leu Lys Glu Ser Leu Leu
50 55 60

Glu Asp Phe Lys Gly Tyr Leu Gly Cys Gln Ala Leu Ser Glu Met Ile
65 70 75 80

Gln Phe Tyr Leu Glu Glu Val Met Pro Gln Ala Glu Asn Gln Asp Pro
85 90 95

Glu Ile Lys Asp His Val Asn Ser Leu Gly Glu Asn Leu Lys Thr Leu
100 105 110

Arg Leu Arg Leu Arg Gln Cys Pro Leu Leu Gly Cys Gly Asp Lys Ala
115 120 125

Val Glu Gln Ile Lys Asn Ala Phe Asn Lys Leu Gln Glu Lys Gly Ile
130 135 140

Tyr Lys Ala Met Ser Glu Phe Asp Ile Phe Ile Asn Tyr Ile Glu Ala
145 150 155 160

Tyr Met Thr Ile Lys Ala Arg
165

<210> SEQ ID NO 13
<211> LENGTH: 167
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

Met Asp Met Arg Val Pro Ala Gln Leu Leu Gly Leu Leu Leu Leu Trp
1 5 10 15

```
Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Leu Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Gln Cys Pro Leu Leu Gly Cys Gly Asp Lys Ala
        115                 120                 125

Val Glu Gln Ile Lys Asn Ala Phe Asn Lys Leu Gln Glu Lys Gly Ile
    130                 135                 140

Tyr Lys Ala Met Ser Glu Phe Asp Ile Phe Ile Asn Tyr Ile Glu Ala
145                 150                 155                 160

Tyr Met Thr Ile Lys Ala Arg
                165


<210> SEQ ID NO 14
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Leu Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170


<210> SEQ ID NO 15
<211> LENGTH: 170
<212> TYPE: PRT
```

-continued

<213> ORGANISM: Artificial Sequence
<220> FEATURE:
<223> OTHER INFORMATION: Description of Artificial Sequence: Synthetic
polypeptide

<400> SEQUENCE: 15

```
Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170
```

<210> SEQ ID NO 16
<211> LENGTH: 170
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

```
Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Leu Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
```

145 150 155 160

Ile Glu Ala Tyr Met Thr Ile Lys Ala Arg
165 170

<210> SEQ ID NO 17
<211> LENGTH: 184
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Asp Met Arg Val Pro Ala Gln Leu Leu Gly Leu Leu Leu Leu Trp
1 5 10 15

Leu Arg Gly Ala Arg Cys Gly Thr Asp Gln Cys Asp Asn Phe Pro Gln
20 25 30

Met Leu Arg Asp Leu Arg Asp Ala Phe Ser Arg Val Lys Thr Phe Phe
35 40 45

Gln Thr Lys Asp Glu Val Asp Asn Leu Leu Leu Lys Glu Ser Leu Leu
50 55 60

Glu Asp Phe Lys Gly Tyr Leu Gly Cys Gln Ala Leu Ser Glu Met Ile
65 70 75 80

Gln Phe Tyr Leu Glu Glu Val Met Pro Gln Ala Glu Asn Gln Asp Pro
85 90 95

Glu Ala Lys Asp His Val Asn Ser Leu Gly Glu Asn Leu Lys Thr Leu
100 105 110

Arg Leu Arg Leu Arg Arg Cys His Arg Phe Leu Pro Cys Glu Asn Gly
115 120 125

Gly Gly Ser Gly Gly Lys Ser Lys Ala Val Glu Gln Ile Lys Asn Ala
130 135 140

Phe Asn Lys Leu Gln Glu Lys Gly Ile Tyr Lys Ala Met Ser Glu Phe
145 150 155 160

Asp Ile Phe Ile Asn Tyr Ile Glu Ala Tyr Met Thr Ile Lys Ala Arg
165 170 175

Asp Tyr Lys Asp Asp Asp Asp Lys
180

<210> SEQ ID NO 18
<211> LENGTH: 184
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Met Asp Met Arg Val Pro Ala Gln Leu Leu Gly Leu Leu Leu Leu Trp
1 5 10 15

Leu Arg Gly Ala Arg Cys Gly Thr Asp Gln Cys Asp Asn Phe Pro Gln
20 25 30

Met Leu Arg Asp Leu Arg Asp Ala Phe Ser Arg Val Lys Thr Phe Phe
35 40 45

Gln Thr Lys Asp Glu Leu Asp Asn Leu Leu Leu Lys Glu Ser Leu Leu
50 55 60

Glu Asp Phe Lys Gly Tyr Leu Gly Cys Gln Ala Leu Ser Glu Met Ile
65 70 75 80

Gln Phe Tyr Leu Glu Glu Val Met Pro Gln Ala Glu Asn Gln Asp Pro

```
                85                  90                  95

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Gly
        115                 120                 125

Gly Gly Ser Gly Gly Lys Ser Lys Ala Val Glu Gln Ile Lys Asn Ala
    130                 135                 140

Phe Asn Lys Leu Gln Glu Lys Gly Ile Tyr Lys Ala Met Ser Glu Phe
145                 150                 155                 160

Asp Ile Phe Ile Asn Tyr Ile Glu Ala Tyr Met Thr Ile Lys Ala Arg
                165                 170                 175

Asp Tyr Lys Asp Asp Asp Asp Lys
            180


<210> SEQ ID NO 19
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Gly
        115                 120                 125

Gly Gly Ser Gly Gly Lys Ser Lys Ala Val Glu Gln Ile Lys Asn Ala
    130                 135                 140

Phe Asn Lys Leu Gln Glu Lys Gly Ile Tyr Lys Ala Met Ser Glu Phe
145                 150                 155                 160

Asp Ile Phe Ile Asn Tyr Ile Glu Ala Tyr Met Thr Ile Lys Ala Arg
                165                 170                 175

Asp Tyr Lys Asp Asp Asp Asp Lys
            180


<210> SEQ ID NO 20
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Met Arg Val Pro Ala Gln Leu Leu Gly Leu Leu Leu Leu Trp
```

-continued

```
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Leu Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Gly
        115                 120                 125

Gly Gly Ser Gly Gly Lys Ser Lys Ala Val Glu Gln Ile Lys Asn Ala
    130                 135                 140

Phe Asn Lys Leu Gln Glu Lys Gly Ile Tyr Lys Ala Met Ser Glu Phe
145                 150                 155                 160

Asp Ile Phe Ile Asn Tyr Ile Glu Ala Tyr Met Thr Ile Lys Ala Arg
                165                 170                 175

Asp Tyr Lys Asp Asp Asp Asp Lys
            180


<210> SEQ ID NO 21
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Met Arg Val Pro Ala Gln Leu Leu Gly Leu Leu Leu Leu Trp
1               5                   10                  15

Leu Arg Gly Ala Arg Cys Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Gly Gly Gly Ser Gly Gly Lys Ser Lys Ala
    130                 135                 140

Val Glu Gln Val Lys Asn Ala Phe Asn Lys Leu Gln Glu Lys Gly Ile
145                 150                 155                 160

Tyr Lys Ala Met Ser Glu Phe Asp Ile Phe Ile Asn Tyr Ile Glu Ala
                165                 170                 175
```

-continued

```
Tyr Met Thr Met Lys Ile Arg Asn Asp Tyr Lys Asp Asp Asp Asp Lys
            180                 185                 190


<210> SEQ ID NO 22
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asp Met Arg Val Pro Ala Gln Leu Leu Gly Leu Leu Leu Leu Trp
1               5                   10                  15

Leu Arg Gly Ala Arg Cys Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn Asp Tyr Lys Asp Asp Asp Asp Lys
            180                 185


<210> SEQ ID NO 23
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95
```

```
Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg Asp Tyr Lys Asp Asp Asp
                165                 170                 175

Asp Lys


<210> SEQ ID NO 24
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Asn Phe Thr Thr Tyr
            20                  25                  30

Ala Met His Trp Val Arg Gln Ala Pro Gly Gln Gly Leu Glu Trp Met
        35                  40                  45

Gly Trp Ile Asn Gly Gly Asn Gly Asp Thr Arg Tyr Ser Gln Lys Phe
    50                  55                  60

Arg Gly Arg Val Thr Ile Ser Arg Asp Thr Ser Ala Ser Thr Ala Tyr
65                  70                  75                  80

Met Glu Leu His Ser Leu Thr Ser Glu Asp Thr Ala Leu Phe Tyr Cys
                85                  90                  95

Ala Arg Glu Ser Gly Asp Tyr Tyr Ser Glu Ile Ser Gly Ala Leu Asp
            100                 105                 110

Trp Gly Gln Gly Thr Leu Val Thr Val Ser Ser Gly Gly Gly Gly Ser
        115                 120                 125

Glu Ile Val Met Thr Gln Ser Pro Gly Thr Leu Ser Leu Ser Pro Gly
    130                 135                 140

Glu Arg Ala Thr Leu Ser Cys Arg Ala Ser Gln Ser Val Pro Arg Asn
145                 150                 155                 160

Tyr Ile Gly Trp Phe Gln Gln Lys Pro Gly Gln Ala Pro Arg Leu Leu
                165                 170                 175

Ile Tyr Gly Ala Ser Ser Arg Ala Ala Gly Phe Pro Asp Arg Phe Ser
            180                 185                 190

Gly Ser Gly Ser Gly Thr Asp Phe Thr Leu Thr Ile Thr Arg Leu Glu
        195                 200                 205

Pro Glu Asp Phe Ala Met Tyr Tyr Cys His Gln Tyr Asp Arg Leu Pro
    210                 215                 220

Tyr Thr Phe Gly Gln Gly Thr Lys Leu Glu Ile Lys Gly Gly Gly Gly
225                 230                 235                 240

Ser Gly Gly Gly Gly Ser Gly Gly Gly Gly Ser Thr Asp Gln Cys Asp
                245                 250                 255

Asn Phe Pro Gln Met Leu Arg Asp Leu Arg Asp Ala Phe Ser Arg Val
            260                 265                 270
```

Lys Thr Phe Phe Gln Thr Lys Asp Glu Leu Asp Asn Leu Leu Leu Lys
275 280 285

Glu Ser Leu Leu Glu Asp Phe Lys Gly Tyr Leu Gly Cys Gln Ala Leu
290 295 300

Ser Glu Met Ile Gln Phe Tyr Leu Glu Glu Val Met Pro Gln Ala Glu
305 310 315 320

Asn Gln Asp Pro Glu Ala Lys Asp His Val Asn Ser Leu Gly Glu Asn
325 330 335

Leu Lys Thr Leu Arg Leu Arg Leu Arg Arg Cys His Arg Phe Leu Pro
340 345 350

Cys Glu Asn Lys Ser Lys Ala Val Glu Gln Ile Lys Asn Ala Phe Asn
355 360 365

Lys Leu Gln Glu Lys Gly Ile Tyr Lys Ala Met Ser Glu Phe Asp Ile
370 375 380

Phe Ile Asn Tyr Ile Glu Ala Tyr Met Thr Ile Lys Ala Arg
385 390 395

<210> SEQ ID NO 25
<211> LENGTH: 397
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ala Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg Gly Gly Gly Gly Ser Gly Gly Gly Gly Ser Gly Gly Gly
145 150 155 160

Gly Ser Gln Val Gln Leu Gln Gln Trp Gly Ala Gly Leu Leu Lys Pro
165 170 175

Ser Glu Thr Leu Ser Leu Thr Cys Ala Val Tyr Gly Gly Ser Phe Thr
180 185 190

Thr Thr Tyr Trp Asn Trp Ile Arg Gln Pro Pro Gly Lys Gly Leu Glu
195 200 205

Trp Ile Gly Glu Val Asn Tyr Ser Gly Asn Ala Asn Tyr Asn Pro Ser
210 215 220

Leu Lys Gly Arg Val Ala Ile Ser Val Asp Thr Ser Lys Asn Gln Phe
225 230 235 240

```
Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Ser Tyr Glu Leu Thr Gln Pro Pro Ser Val Ser Val Ser Pro Gly
    290                 295                 300

Gln Thr Ala Arg Ile Thr Cys Ser Gly Asp Val Leu Pro Lys Lys Tyr
305                 310                 315                 320

Ala Tyr Trp Tyr Gln Gln Lys Ser Gly Leu Ala Pro Val Leu Val Ile
                325                 330                 335

Tyr Glu Asp Asn Arg Arg Pro Ser Gly Ile Pro Glu Arg Phe Ser Gly
            340                 345                 350

Ser Ser Ser Gly Thr Met Ala Thr Leu Thr Ile Ser Gly Ala Gln Val
        355                 360                 365

Glu Asp Glu Gly Asp Tyr Tyr Cys Ser Ser Thr Asp Ser Ser Gly Asp
    370                 375                 380

His Tyr Val Phe Gly Thr Gly Thr Lys Val Thr Val Leu
385                 390                 395


<210> SEQ ID NO 26
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Asn Phe Thr Thr Tyr
            20                  25                  30

Ala Met His Trp Val Arg Gln Ala Pro Gly Gln Gly Leu Glu Trp Met
        35                  40                  45

Gly Trp Ile Asn Gly Gly Asn Gly Asp Thr Arg Tyr Ser Gln Lys Phe
    50                  55                  60

Arg Gly Arg Val Thr Ile Ser Arg Asp Thr Ser Ala Ser Thr Ala Tyr
65                  70                  75                  80

Met Glu Leu His Ser Leu Thr Ser Glu Asp Thr Ala Leu Phe Tyr Cys
                85                  90                  95

Ala Arg Glu Ser Gly Asp Tyr Tyr Ser Glu Ile Ser Gly Ala Leu Asp
            100                 105                 110

Trp Gly Gln Gly Thr Leu Val Thr Val Ser Ser Gly Gly Gly Gly Ser
        115                 120                 125

Glu Ile Val Met Thr Gln Ser Pro Gly Thr Leu Ser Leu Ser Pro Gly
    130                 135                 140

Glu Arg Ala Thr Leu Ser Cys Arg Ala Ser Gln Ser Val Pro Arg Asn
145                 150                 155                 160

Tyr Ile Gly Trp Phe Gln Gln Lys Pro Gly Gln Ala Pro Arg Leu Leu
                165                 170                 175

Ile Tyr Gly Ala Ser Ser Arg Ala Ala Gly Phe Pro Asp Arg Phe Ser
            180                 185                 190

Gly Ser Gly Ser Gly Thr Asp Phe Thr Leu Thr Ile Thr Arg Leu Glu
```

```
        195                 200                 205

Pro Glu Asp Phe Ala Met Tyr Tyr Cys His Gln Tyr Asp Arg Leu Pro
    210                 215                 220

Tyr Thr Phe Gly Gln Gly Thr Lys Leu Glu Ile Lys Gly Gly Gly Gly
225                 230                 235                 240

Ser Gly Gly Gly Gly Ser Gly Gly Gly Gly Ser Thr Asp Gln Cys Asp
                245                 250                 255

Asn Phe Pro Gln Met Leu Arg Asp Leu Arg Asp Ala Phe Ser Arg Val
            260                 265                 270

Lys Thr Phe Phe Gln Thr Lys Asp Glu Val Asp Asn Leu Leu Leu Lys
        275                 280                 285

Glu Ser Leu Leu Glu Asp Phe Lys Gly Tyr Leu Gly Cys Gln Ala Leu
    290                 295                 300

Ser Glu Met Ile Gln Phe Tyr Leu Glu Glu Val Met Pro Gln Ala Glu
305                 310                 315                 320

Asn Gln Asp Pro Glu Ile Lys Asp His Val Asn Ser Leu Gly Glu Asn
                325                 330                 335

Leu Lys Thr Leu Arg Leu Arg Leu Arg Arg Cys His Arg Phe Leu Pro
            340                 345                 350

Cys Glu Asn Lys Ser Lys Ala Val Glu Gln Ile Lys Asn Ala Phe Asn
        355                 360                 365

Lys Leu Gln Glu Lys Gly Ile Tyr Lys Ala Met Ser Glu Phe Asp Ile
    370                 375                 380

Phe Ile Asn Tyr Ile Glu Ala Tyr Met Thr Ile Lys Ala Arg
385                 390                 395


<210> SEQ ID NO 27
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160
```

-continued

Gly Ser Gln Val Gln Leu Gln Gln Trp Gly Ala Gly Leu Leu Lys Pro
165 170 175

Ser Glu Thr Leu Ser Leu Thr Cys Ala Val Tyr Gly Gly Ser Phe Thr
180 185 190

Thr Thr Tyr Trp Asn Trp Ile Arg Gln Pro Pro Gly Lys Gly Leu Glu
195 200 205

Trp Ile Gly Glu Val Asn Tyr Ser Gly Asn Ala Asn Tyr Asn Pro Ser
210 215 220

Leu Lys Gly Arg Val Ala Ile Ser Val Asp Thr Ser Lys Asn Gln Phe
225 230 235 240

Ser Leu Arg Leu Asn Ser Val Thr Ala Ala Asp Thr Ala Ile Tyr Tyr
245 250 255

Cys Thr Ser Arg Ile Arg Ser His Ile Ala Tyr Ser Trp Lys Gly Asp
260 265 270

Val Trp Gly Lys Gly Thr Thr Val Thr Val Ser Ser Gly Gly Gly Gly
275 280 285

Ser Ser Tyr Glu Leu Thr Gln Pro Pro Ser Val Ser Val Ser Pro Gly
290 295 300

Gln Thr Ala Arg Ile Thr Cys Ser Gly Asp Val Leu Pro Lys Lys Tyr
305 310 315 320

Ala Tyr Trp Tyr Gln Gln Lys Ser Gly Leu Ala Pro Val Leu Val Ile
325 330 335

Tyr Glu Asp Asn Arg Arg Pro Ser Gly Ile Pro Glu Arg Phe Ser Gly
340 345 350

Ser Ser Ser Gly Thr Met Ala Thr Leu Thr Ile Ser Gly Ala Gln Val
355 360 365

Glu Asp Glu Gly Asp Tyr Tyr Cys Ser Ser Thr Asp Ser Ser Gly Asp
370 375 380

His Tyr Val Phe Gly Thr Gly Thr Lys Val Thr Val Leu
385 390 395

<210> SEQ ID NO 28
<211> LENGTH: 398
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

Gln Val Gln Leu Val Gln Ser Gly Ala Glu Val Lys Lys Pro Gly Ala
1 5 10 15

Ser Val Lys Ile Ser Cys Lys Ala Ser Gly Tyr Asn Phe Thr Thr Tyr
20 25 30

Ala Met His Trp Val Arg Gln Ala Pro Gly Gln Gly Leu Glu Trp Met
35 40 45

Gly Trp Ile Asn Gly Gly Asn Gly Asp Thr Arg Tyr Ser Gln Lys Phe
50 55 60

Arg Gly Arg Val Thr Ile Ser Arg Asp Thr Ser Ala Ser Thr Ala Tyr
65 70 75 80

Met Glu Leu His Ser Leu Thr Ser Glu Asp Thr Ala Leu Phe Tyr Cys
85 90 95

Ala Arg Glu Ser Gly Asp Tyr Tyr Ser Glu Ile Ser Gly Ala Leu Asp
100 105 110

Trp Gly Gln Gly Thr Leu Val Thr Val Ser Ser Gly Gly Gly Gly Ser
115 120 125

Glu Ile Val Met Thr Gln Ser Pro Gly Thr Leu Ser Leu Ser Pro Gly
    130                 135                 140

Glu Arg Ala Thr Leu Ser Cys Arg Ala Ser Gln Ser Val Pro Arg Asn
145                 150                 155                 160

Tyr Ile Gly Trp Phe Gln Gln Lys Pro Gly Gln Ala Pro Arg Leu Leu
                165                 170                 175

Ile Tyr Gly Ala Ser Ser Arg Ala Ala Gly Phe Pro Asp Arg Phe Ser
            180                 185                 190

Gly Ser Gly Ser Gly Thr Asp Phe Thr Leu Thr Ile Thr Arg Leu Glu
        195                 200                 205

Pro Glu Asp Phe Ala Met Tyr Tyr Cys His Gln Tyr Asp Arg Leu Pro
    210                 215                 220

Tyr Thr Phe Gly Gln Gly Thr Lys Leu Glu Ile Lys Gly Gly Gly Gly
225                 230                 235                 240

Ser Gly Gly Gly Gly Ser Gly Gly Gly Gly Ser Thr Asp Gln Cys Asp
                245                 250                 255

Asn Phe Pro Gln Met Leu Arg Asp Leu Arg Asp Ala Phe Ser Arg Val
            260                 265                 270

Lys Thr Phe Phe Gln Thr Lys Asp Glu Leu Asp Asn Leu Leu Leu Lys
        275                 280                 285

Glu Ser Leu Leu Glu Asp Phe Lys Gly Tyr Leu Gly Cys Gln Ala Leu
    290                 295                 300

Ser Glu Met Ile Gln Phe Tyr Leu Glu Glu Val Met Pro Gln Ala Glu
305                 310                 315                 320

Asn Gln Asp Pro Glu Ile Lys Asp His Val Asn Ser Leu Gly Glu Asn
                325                 330                 335

Leu Lys Thr Leu Arg Leu Arg Leu Arg Arg Cys His Arg Phe Leu Pro
            340                 345                 350

Cys Glu Asn Lys Ser Lys Ala Val Glu Gln Ile Lys Asn Ala Phe Asn
        355                 360                 365

Lys Leu Gln Glu Lys Gly Ile Tyr Lys Ala Met Ser Glu Phe Asp Ile
    370                 375                 380

Phe Ile Asn Tyr Ile Glu Ala Tyr Met Thr Ile Lys Ala Arg
385                 390                 395

<210> SEQ ID NO 29
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys

```
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Ser Tyr Glu Leu Thr Gln Pro Pro Ser Val Ser Val Ser Pro Gly
    290                 295                 300

Gln Thr Ala Arg Ile Thr Cys Ser Gly Asp Val Leu Pro Lys Lys Tyr
305                 310                 315                 320

Ala Tyr Trp Tyr Gln Gln Lys Ser Gly Leu Ala Pro Val Leu Val Ile
                325                 330                 335

Tyr Glu Asp Asn Arg Arg Pro Ser Gly Ile Pro Glu Arg Phe Ser Gly
            340                 345                 350

Ser Ser Ser Gly Thr Met Ala Thr Leu Thr Ile Ser Gly Ala Gln Val
        355                 360                 365

Glu Asp Glu Gly Asp Tyr Tyr Cys Ser Ser Thr Asp Ser Ser Gly Asp
    370                 375                 380

His Tyr Val Phe Gly Thr Gly Thr Lys Val Thr Val Leu
385                 390                 395
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

```
Ser Ser Gly Gly Gly Gly Ser
1               5
```

<210> SEQ ID NO 31
<211> LENGTH: 15
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 31

Gly Gly Gly Gly Ser Gly Gly Gly Gly Ser Gly Gly Gly Gly Ser
1 5 10 15

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 32

His His His His His His
1 5

<210> SEQ ID NO 33
<211> LENGTH: 567
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ile Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg Gly Gly Gly Gly Ser Gly Gly Gly Gly Ser Gly Gly Gly
145 150 155 160

Gly Ser Gln Val Gln Leu Gln Gln Trp Gly Ala Gly Leu Leu Lys Pro
165 170 175

Ser Glu Thr Leu Ser Leu Thr Cys Ala Val Tyr Gly Gly Ser Phe Thr
180 185 190

Thr Thr Tyr Trp Asn Trp Ile Arg Gln Pro Pro Gly Lys Gly Leu Glu
195 200 205

Trp Ile Gly Glu Val Asn Tyr Ser Gly Asn Ala Asn Tyr Asn Pro Ser
210 215 220

Leu Lys Gly Arg Val Ala Ile Ser Val Asp Thr Ser Lys Asn Gln Phe
225 230 235 240

Ser Leu Arg Leu Asn Ser Val Thr Ala Ala Asp Thr Ala Ile Tyr Tyr

-continued

```
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Gly Gly Gly Gly Ser Gly
        275                 280                 285

Gly Gly Gly Ser Gly Gly Gly Gly Ser Glu Ile Val Met Thr Gln Ser
    290                 295                 300

Pro Gly Thr Leu Ser Leu Ser Pro Gly Glu Arg Ala Thr Leu Ser Cys
305                 310                 315                 320

Arg Ala Ser Gln Ser Val Pro Arg Asn Tyr Ile Gly Trp Phe Gln Gln
                325                 330                 335

Lys Pro Gly Gln Ala Pro Arg Leu Leu Ile Tyr Gly Ala Ser Ser Arg
            340                 345                 350

Ala Ala Gly Phe Pro Asp Arg Phe Ser Gly Ser Gly Ser Gly Thr Asp
        355                 360                 365

Phe Thr Leu Thr Ile Thr Arg Leu Glu Pro Glu Asp Phe Ala Met Tyr
    370                 375                 380

Tyr Cys His Gln Tyr Asp Arg Leu Pro Tyr Thr Phe Gly Gln Gly Thr
385                 390                 395                 400

Lys Leu Glu Ile Lys Gly Gly Gly Gly Ser Gly Gly Gly Gly Ser Gly
                405                 410                 415

Gly Gly Gly Ser Thr Asp Gln Cys Asp Asn Phe Pro Gln Met Leu Arg
            420                 425                 430

Asp Leu Arg Asp Ala Phe Ser Arg Val Lys Thr Phe Phe Gln Thr Lys
        435                 440                 445

Asp Glu Leu Asp Asn Leu Leu Leu Lys Glu Ser Leu Leu Glu Asp Phe
    450                 455                 460

Lys Gly Tyr Leu Gly Cys Gln Ala Leu Ser Glu Met Ile Gln Phe Tyr
465                 470                 475                 480

Leu Glu Glu Val Met Pro Gln Ala Glu Asn Gln Asp Pro Glu Ile Lys
                485                 490                 495

Asp His Val Asn Ser Leu Gly Glu Asn Leu Lys Thr Leu Arg Leu Arg
            500                 505                 510

Leu Arg Arg Cys His Arg Phe Leu Pro Cys Glu Asn Lys Ser Lys Ala
        515                 520                 525

Val Glu Gln Ile Lys Asn Ala Phe Asn Lys Leu Gln Glu Lys Gly Ile
    530                 535                 540

Tyr Lys Ala Met Ser Glu Phe Asp Ile Phe Ile Asn Tyr Ile Glu Ala
545                 550                 555                 560

Tyr Met Thr Ile Lys Ala Arg
                565


<210> SEQ ID NO 34
<211> LENGTH: 561
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30
```

-continued

```
Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Thr
            180                 185                 190

Asn Tyr Gly Val His Trp Ile Arg Gln Pro Pro Gly Lys Gly Leu Glu
        195                 200                 205

Trp Ile Gly Val Ile Trp Ser Gly Gly Asn Thr Asp Tyr Asn Thr Pro
    210                 215                 220

Phe Thr Ser Arg Val Thr Ile Ser Val Asp Thr Ser Lys Asn Gln Phe
225                 230                 235                 240

Ser Leu Gln Leu Asn Ser Val Thr Ala Ala Asp Thr Ala Ile Tyr Tyr
                245                 250                 255

Cys Thr Ser Leu Thr Tyr Tyr Asp Tyr Glu Phe Ala Trp Gly Lys Gly
            260                 265                 270

Thr Thr Val Thr Val Gly Gly Gly Gly Ser Gly Gly Gly Gly Ser Gly
        275                 280                 285

Gly Gly Gly Ser Glu Ile Val Met Thr Gln Ser Pro Gly Thr Leu Ser
    290                 295                 300

Leu Ser Pro Gly Glu Arg Ala Thr Leu Ser Cys Arg Ala Ser Gln Ser
305                 310                 315                 320

Ile Gly Thr Asn Ile His Trp Phe Gln Gln Lys Pro Gly Gln Ala Pro
                325                 330                 335

Arg Leu Leu Ile Tyr Tyr Ala Ser Glu Ser Ile Ser Gly Phe Pro Asp
            340                 345                 350

Arg Phe Ser Gly Ser Gly Ser Gly Thr Asp Phe Thr Leu Thr Ile Thr
        355                 360                 365

Arg Leu Glu Pro Glu Asp Phe Ala Met Tyr Tyr Cys Gln Gln Asn Asn
    370                 375                 380

Asn Trp Pro Thr Thr Phe Gly Gln Gly Thr Lys Leu Glu Ile Lys Gly
385                 390                 395                 400

Gly Gly Gly Ser Gly Gly Gly Gly Ser Gly Gly Gly Gly Ser Thr Asp
                405                 410                 415

Gln Cys Asp Asn Phe Pro Gln Met Leu Arg Asp Leu Arg Asp Ala Phe
            420                 425                 430

Ser Arg Val Lys Thr Phe Phe Gln Thr Lys Asp Glu Leu Asp Asn Leu
        435                 440                 445

Leu Leu Lys Glu Ser Leu Leu Glu Asp Phe Lys Gly Tyr Leu Gly Cys
```

```
    450                 455                 460

Gln Ala Leu Ser Glu Met Ile Gln Phe Tyr Leu Glu Glu Val Met Pro
465                 470                 475                 480

Gln Ala Glu Asn Gln Asp Pro Glu Ile Lys Asp His Val Asn Ser Leu
                485                 490                 495

Gly Glu Asn Leu Lys Thr Leu Arg Leu Arg Leu Arg Arg Cys His Arg
            500                 505                 510

Phe Leu Pro Cys Glu Asn Lys Ser Lys Ala Val Glu Gln Ile Lys Asn
        515                 520                 525

Ala Phe Asn Lys Leu Gln Glu Lys Gly Ile Tyr Lys Ala Met Ser Glu
    530                 535                 540

Phe Asp Ile Phe Ile Asn Tyr Ile Glu Ala Tyr Met Thr Ile Lys Ala
545                 550                 555                 560

Arg


<210> SEQ ID NO 35
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Thr Asn Tyr
            20                  25                  30

Gly Val His Trp Ile Arg Gln Pro Pro Gly Lys Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Ala Ile Ser Val Asp Thr Ser Lys Asn Gln Phe Ser Leu
65                  70                  75                  80

Arg Leu Asn Ser Val Thr Ala Ala Asp Thr Ala Ile Tyr Tyr Cys Thr
                85                  90                  95

Ser Leu Thr Tyr Tyr Asp Tyr Glu Phe Ala Trp Lys Gly Asp Val Trp
            100                 105                 110

Gly Lys Gly Thr Thr Val Thr Val Ser Ser Gly Gly Gly Gly Ser Glu
        115                 120                 125

Ile Val Met Thr Gln Ser Pro Gly Thr Leu Ser Leu Ser Pro Gly Glu
    130                 135                 140

Arg Ala Thr Leu Ser Cys Arg Ala Ser Gln Ser Ile Gly Thr Asn Ile
145                 150                 155                 160

His Trp Phe Gln Gln Lys Pro Gly Gln Ala Pro Arg Leu Leu Ile Tyr
                165                 170                 175

Tyr Ala Ser Glu Ser Ile Ser Gly Phe Pro Asp Arg Phe Ser Gly Ser
            180                 185                 190

Gly Ser Gly Thr Asp Phe Thr Leu Thr Ile Thr Arg Leu Glu Pro Glu
        195                 200                 205

Asp Phe Ala Met Tyr Tyr Cys Gln Gln Asn Asn Asn Trp Pro Thr Thr
    210                 215                 220

Phe Gly Gln Gly Thr Lys Leu Glu Ile Lys Gly Gly Gly Gly Ser Gly
225                 230                 235                 240

Gly Gly Gly Ser Gly Gly Gly Gly Ser Thr Asp Gln Cys Asp Asn Phe
```

```
                245                 250                 255

Pro Gln Met Leu Arg Asp Leu Arg Asp Ala Phe Ser Arg Val Lys Thr
            260                 265                 270

Phe Phe Gln Thr Lys Asp Glu Leu Asp Asn Leu Leu Leu Lys Glu Ser
        275                 280                 285

Leu Leu Glu Asp Phe Lys Gly Tyr Leu Gly Cys Gln Ala Leu Ser Glu
    290                 295                 300

Met Ile Gln Phe Tyr Leu Glu Glu Val Met Pro Gln Ala Glu Asn Gln
305                 310                 315                 320

Asp Pro Glu Ile Lys Asp His Val Asn Ser Leu Gly Glu Asn Leu Lys
                325                 330                 335

Thr Leu Arg Leu Arg Leu Arg Arg Cys His Arg Phe Leu Pro Cys Glu
            340                 345                 350

Asn Lys Ser Lys Ala Val Glu Gln Ile Lys Asn Ala Phe Asn Lys Leu
        355                 360                 365

Gln Glu Lys Gly Ile Tyr Lys Ala Met Ser Glu Phe Asp Ile Phe Ile
    370                 375                 380

Asn Tyr Ile Glu Ala Tyr Met Thr Ile Lys Ala Arg
385                 390                 395


<210> SEQ ID NO 36
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Asn
            180                 185                 190

Tyr Gly Val His Trp Ile Arg Gln Pro Pro Gly Lys Gly Leu Glu Trp
        195                 200                 205
```

```
Ile Gly Val Ile Trp Ser Gly Gly Asn Thr Asp Tyr Asn Thr Pro Phe
    210                 215                 220

Thr Ser Arg Val Ala Ile Ser Val Asp Thr Ser Lys Asn Gln Phe Ser
225                 230                 235                 240

Leu Arg Leu Asn Ser Val Thr Ala Ala Asp Thr Ala Ile Tyr Tyr Cys
                245                 250                 255

Thr Ser Leu Thr Tyr Tyr Asp Tyr Glu Phe Ala Trp Lys Gly Asp Val
            260                 265                 270

Trp Gly Lys Gly Thr Thr Val Thr Val Ser Ser Gly Gly Gly Gly Ser
        275                 280                 285

Glu Ile Val Met Thr Gln Ser Pro Gly Thr Leu Ser Leu Ser Pro Gly
    290                 295                 300

Glu Arg Ala Thr Leu Ser Cys Arg Ala Ser Gln Ser Ile Gly Thr Asn
305                 310                 315                 320

Ile His Trp Phe Gln Gln Lys Pro Gly Gln Ala Pro Arg Leu Leu Ile
                325                 330                 335

Tyr Tyr Ala Ser Glu Ser Ile Ser Gly Phe Pro Asp Arg Phe Ser Gly
            340                 345                 350

Ser Gly Ser Gly Thr Asp Phe Thr Leu Thr Ile Thr Arg Leu Glu Pro
        355                 360                 365

Glu Asp Phe Ala Met Tyr Tyr Cys Gln Gln Asn Asn Asn Trp Pro Thr
    370                 375                 380

Thr Phe Gly Gln Gly Thr Lys Leu Glu Ile Lys Asp Tyr Lys Asp Asp
385                 390                 395                 400

Asp Asp Lys
```

```
<210> SEQ ID NO 37
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (193)..(199)
<223> OTHER INFORMATION: Any amino acid
<220> FEATURE:
<221> NAME/KEY: MISC_FEATURE
<222> LOCATION: (193)..(199)
<223> OTHER INFORMATION: This region may encompass 3-7 residues
<220> FEATURE:
<221> NAME/KEY: MOD_RES
<222> LOCATION: (214)..(231)
<223> OTHER INFORMATION: Any amino acid
<220> FEATURE:
<221> NAME/KEY: MISC_FEATURE
<222> LOCATION: (214)..(231)
<223> OTHER INFORMATION: This region may encompass 14-18 residues
<220> FEATURE:
<221> NAME/KEY: MOD_RES
<222> LOCATION: (264)..(274)
<223> OTHER INFORMATION: Any amino acid
<220> FEATURE:
<221> NAME/KEY: MISC_FEATURE
<222> LOCATION: (264)..(274)
<223> OTHER INFORMATION: This region may encompass 7-11 residues
<220> FEATURE:
<221> NAME/KEY: MOD_RES
<222> LOCATION: (329)..(342)
<223> OTHER INFORMATION: Any amino acid
<220> FEATURE:
<221> NAME/KEY: MISC_FEATURE
<222> LOCATION: (329)..(342)
<223> OTHER INFORMATION: This region may encompass 9-14 residues
<220> FEATURE:
```

<221> NAME/KEY: MOD_RES
<222> LOCATION: (358)..(366)
<223> OTHER INFORMATION: Any amino acid
<220> FEATURE:
<221> NAME/KEY: MISC_FEATURE
<222> LOCATION: (358)..(366)
<223> OTHER INFORMATION: This region may encompass 5-9 residues
<220> FEATURE:
<221> NAME/KEY: MOD_RES
<222> LOCATION: (399)..(409)
<223> OTHER INFORMATION: Any amino acid
<220> FEATURE:
<221> NAME/KEY: MISC_FEATURE
<222> LOCATION: (399)..(409)
<223> OTHER INFORMATION: This region may encompass 7-11 residues
<220> FEATURE:
<223> OTHER INFORMATION: See specification as filed for detailed
      description of substitutions and preferred embodiments

<400> SEQUENCE: 37

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Xaa Xaa Xaa Xaa Xaa Xaa Xaa Trp Ile Arg Gln Pro Pro Gly Lys Gly
        195                 200                 205

Leu Glu Trp Ile Gly Xaa Xaa Xaa Xaa Xaa Xaa Xaa Xaa Xaa Xaa Xaa
    210                 215                 220

Xaa Xaa Xaa Xaa Xaa Xaa Xaa Arg Val Ala Ile Ser Val Asp Thr Ser
225                 230                 235                 240

Lys Asn Gln Phe Ser Leu Arg Leu Asn Ser Val Thr Ala Ala Asp Thr
                245                 250                 255

Ala Ile Tyr Tyr Cys Thr Ser Xaa Xaa Xaa Xaa Xaa Xaa Xaa Xaa Xaa
            260                 265                 270

Xaa Xaa Trp Lys Gly Asp Val Trp Gly Lys Gly Thr Thr Val Thr Val
        275                 280                 285

Ser Ser Gly Gly Gly Gly Ser Gly Gly Gly Gly Ser Gly Gly Gly Gly
    290                 295                 300

Ser Glu Ile Val Met Thr Gln Ser Pro Gly Thr Leu Ser Leu Ser Pro
```

-continued

```
305                 310                 315                 320

Gly Glu Arg Ala Thr Leu Ser Cys Xaa Xaa Xaa Xaa Xaa Xaa Xaa Xaa
                325                 330                 335

Xaa Xaa Xaa Xaa Xaa Xaa Trp Phe Gln Gln Lys Pro Gly Gln Ala Pro
            340                 345                 350

Arg Leu Leu Ile Tyr Xaa Xaa Xaa Xaa Xaa Xaa Xaa Xaa Xaa Gly Phe
        355                 360                 365

Pro Asp Arg Phe Ser Gly Ser Gly Ser Gly Thr Asp Phe Thr Leu Thr
    370                 375                 380

Ile Thr Arg Leu Glu Pro Glu Asp Phe Ala Met Tyr Tyr Cys Xaa Xaa
385                 390                 395                 400

Xaa Xaa Xaa Xaa Xaa Xaa Xaa Xaa Xaa Phe Gly Gln Gly Thr Lys Leu
                405                 410                 415

Glu Ile Lys Gly Gly Gly Gly Ser Gly Gly Gly Gly Ser Gly Gly Gly
            420                 425                 430

Gly Ser Thr Asp Gln Cys Asp Asn Phe Pro Gln Met Leu Arg Asp Leu
        435                 440                 445

Arg Asp Ala Phe Ser Arg Val Lys Thr Phe Phe Gln Thr Lys Asp Glu
    450                 455                 460

Val Asp Asn Leu Leu Leu Lys Glu Ser Leu Leu Glu Asp Phe Lys Gly
465                 470                 475                 480

Tyr Leu Gly Cys Gln Ala Leu Ser Glu Met Ile Gln Phe Tyr Leu Glu
                485                 490                 495

Glu Val Met Pro Gln Ala Glu Asn Gln Asp Pro Glu Ile Lys Asp His
            500                 505                 510

Val Asn Ser Leu Gly Glu Asn Leu Lys Thr Leu Arg Leu Arg Leu Arg
        515                 520                 525

Arg Cys His Arg Phe Leu Pro Cys Glu Asn Lys Ser Lys Ala Val Glu
    530                 535                 540

Gln Ile Lys Asn Ala Phe Asn Lys Leu Gln Glu Lys Gly Ile Tyr Lys
545                 550                 555                 560

Ala Met Ser Glu Phe Asp Ile Phe Ile Asn Tyr Ile Glu Ala Tyr Met
                565                 570                 575

Thr Ile Lys Ala Arg
            580


<210> SEQ ID NO 38
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Thr Thr Thr
            20                  25                  30

Tyr Trp Asn Trp Ile Arg Gln Pro Pro Gly Lys Gly Leu Glu Trp Ile
        35                  40                  45

Gly Glu Val Asn Tyr Ser Gly Asn Ala Asn Tyr Asn Pro Ser Leu Lys
    50                  55                  60

Gly Arg Val Ala Ile Ser Val Asp Thr Ser Lys Asn Gln Phe Ser Leu
65                  70                  75                  80
```

```
Arg Leu Asn Ser Val Thr Ala Ala Asp Thr Ala Ile Tyr Tyr Cys Thr
                85                  90                  95

Ser Arg Ile Arg Ser His Ile Ala Tyr Ser Trp Lys Gly Asp Val Trp
            100                 105                 110

Gly Lys Gly Thr Thr Val Thr Val Ser Ser Gly Gly Gly Gly Ser Glu
        115                 120                 125

Ile Val Met Thr Gln Ser Pro Gly Thr Leu Ser Leu Ser Pro Gly Glu
    130                 135                 140

Arg Ala Thr Leu Ser Cys Arg Ala Ser Gln Ser Val Pro Arg Asn Tyr
145                 150                 155                 160

Ile Gly Trp Phe Gln Gln Lys Pro Gly Gln Ala Pro Arg Leu Leu Ile
                165                 170                 175

Tyr Gly Ala Ser Ser Arg Ala Ala Gly Phe Pro Asp Arg Phe Ser Gly
            180                 185                 190

Ser Gly Ser Gly Thr Asp Phe Thr Leu Thr Ile Thr Arg Leu Glu Pro
        195                 200                 205

Glu Asp Phe Ala Met Tyr Tyr Cys His Gln Tyr Asp Arg Leu Pro Tyr
    210                 215                 220

Thr Phe Gly Gln Gly Thr Lys Leu Glu Ile Lys Gly Gly Gly Gly Ser
225                 230                 235                 240

Gly Gly Gly Gly Ser Gly Gly Gly Gly Ser Thr Asp Gln Cys Asp Asn
                245                 250                 255

Phe Pro Gln Met Leu Arg Asp Leu Arg Asp Ala Phe Ser Arg Val Lys
            260                 265                 270

Thr Phe Phe Gln Thr Lys Asp Glu Leu Asp Asn Leu Leu Leu Lys Glu
        275                 280                 285

Ser Leu Leu Glu Asp Phe Lys Gly Tyr Leu Gly Cys Gln Ala Leu Ser
    290                 295                 300

Glu Met Ile Gln Phe Tyr Leu Glu Glu Val Met Pro Gln Ala Glu Asn
305                 310                 315                 320

Gln Asp Pro Glu Ile Lys Asp His Val Asn Ser Leu Gly Glu Asn Leu
                325                 330                 335

Lys Thr Leu Arg Leu Arg Leu Arg Arg Cys His Arg Phe Leu Pro Cys
            340                 345                 350

Glu Asn Lys Ser Lys Ala Val Glu Gln Ile Lys Asn Ala Phe Asn Lys
        355                 360                 365

Leu Gln Glu Lys Gly Ile Tyr Lys Ala Met Ser Glu Phe Asp Ile Phe
    370                 375                 380

Ile Asn Tyr Ile Glu Ala Tyr Met Thr Ile Lys Ala Arg
385                 390                 395
```

<210> SEQ ID NO 39
<211> LENGTH: 405
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45
```

```
Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Glu Ile Val Met Thr Gln Ser Pro Gly Thr Leu Ser Leu Ser Pro
    290                 295                 300

Gly Glu Arg Ala Thr Leu Ser Cys Arg Ala Ser Gln Ser Val Pro Arg
305                 310                 315                 320

Asn Tyr Ile Gly Trp Phe Gln Gln Lys Pro Gly Gln Ala Pro Arg Leu
                325                 330                 335

Leu Ile Tyr Gly Ala Ser Ser Arg Ala Ala Gly Phe Pro Asp Arg Phe
            340                 345                 350

Ser Gly Ser Gly Ser Gly Thr Asp Phe Thr Leu Thr Ile Thr Arg Leu
        355                 360                 365

Glu Pro Glu Asp Phe Ala Met Tyr Tyr Cys His Gln Tyr Asp Arg Leu
    370                 375                 380

Pro Tyr Thr Phe Gly Gln Gly Thr Lys Leu Glu Ile Lys Asp Tyr Lys
385                 390                 395                 400

Asp Asp Asp Asp Lys
                405
```

<210> SEQ ID NO 40
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Gly Gly Gly Gly Ser Gly Gly Gly Gly Ser Glu Ile Val Met Thr
    290                 295                 300

Gln Ser Pro Gly Thr Leu Ser Leu Ser Pro Gly Glu Arg Ala Thr Leu
305                 310                 315                 320

Ser Cys Arg Ala Ser Gln Ser Val Pro Arg Asn Tyr Ile Gly Trp Phe
                325                 330                 335

Gln Gln Lys Pro Gly Gln Ala Pro Arg Leu Leu Ile Tyr Gly Ala Ser
            340                 345                 350

Ser Arg Ala Ala Gly Phe Pro Asp Arg Phe Ser Gly Ser Gly Ser Gly
        355                 360                 365

Thr Asp Phe Thr Leu Thr Ile Thr Arg Leu Glu Pro Glu Asp Phe Ala
    370                 375                 380

Met Tyr Tyr Cys His Gln Tyr Asp Arg Leu Pro Tyr Thr Phe Gly Gln
385                 390                 395                 400

Gly Thr Lys Leu Glu Ile Lys Gly Gly Gly Gly Ser Gly Gly Gly Gly
                405                 410                 415
```

-continued

```
Ser Gly Gly Gly Gly Ser Thr Asp Gln Cys Asp Asn Phe Pro Gln Met
            420                 425                 430

Leu Arg Asp Leu Arg Asp Ala Phe Ser Arg Val Lys Thr Phe Phe Gln
        435                 440                 445

Thr Lys Asp Glu Val Asp Asn Leu Leu Leu Lys Glu Ser Leu Leu Glu
    450                 455                 460

Asp Phe Lys Gly Tyr Leu Gly Cys Gln Ala Leu Ser Glu Met Ile Gln
465                 470                 475                 480

Phe Tyr Leu Glu Glu Val Met Pro Gln Ala Glu Asn Gln Asp Pro Glu
                485                 490                 495

Ile Lys Asp His Val Asn Ser Leu Gly Glu Asn Leu Lys Thr Leu Arg
            500                 505                 510

Leu Arg Leu Arg Arg Cys His Arg Phe Leu Pro Cys Glu Asn Lys Ser
        515                 520                 525

Lys Ala Val Glu Gln Ile Lys Asn Ala Phe Asn Lys Leu Gln Glu Lys
    530                 535                 540

Gly Ile Tyr Lys Ala Met Ser Glu Phe Asp Ile Phe Ile Asn Tyr Ile
545                 550                 555                 560

Glu Ala Tyr Met Thr Ile Lys Ala Arg
                565


<210> SEQ ID NO 41
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Val Tyr Ser Gly Asn Thr Asn Tyr Ala Gln Lys Val
    50                  55                  60

Gln Gly Arg Val Thr Met Thr Ala Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Glu Gly Ser Ser Ser Ser Gly Asp Tyr Tyr Tyr Gly Met Asp
            100                 105                 110

Val Trp Gly Gln Gly Thr Thr Val Thr Val Ser Ser Gly Gly Gly Gly
        115                 120                 125

Ser Glu Ile Val Met Thr Gln Ser Pro Gly Thr Leu Ser Leu Ser Pro
    130                 135                 140

Gly Glu Arg Ala Thr Leu Ser Cys Arg Ala Ser Gln Ser Val Pro Arg
145                 150                 155                 160

Asn Tyr Ile Gly Trp Phe Gln Gln Lys Pro Gly Gln Ala Pro Arg Leu
                165                 170                 175

Leu Ile Tyr Gly Ala Ser Ser Arg Ala Ala Gly Phe Pro Asp Arg Phe
            180                 185                 190

Ser Gly Ser Gly Ser Gly Thr Asp Phe Thr Leu Thr Ile Thr Arg Leu
```

```
        195                 200                 205

Glu Pro Glu Asp Phe Ala Met Tyr Tyr Cys His Gln Tyr Asp Arg Leu
    210                 215                 220

Pro Tyr Thr Phe Gly Gln Gly Thr Lys Leu Glu Ile Lys Gly Gly Gly
225                 230                 235                 240

Gly Ser Gly Gly Gly Gly Ser Gly Gly Gly Gly Ser Thr Asp Gln Cys
                245                 250                 255

Asp Asn Phe Pro Gln Met Leu Arg Asp Leu Arg Asp Ala Phe Ser Arg
            260                 265                 270

Val Lys Thr Phe Phe Gln Thr Lys Asp Glu Val Asp Asn Leu Leu Leu
        275                 280                 285

Lys Glu Ser Leu Leu Glu Asp Phe Lys Gly Tyr Leu Gly Cys Gln Ala
    290                 295                 300

Leu Ser Glu Met Ile Gln Phe Tyr Leu Glu Glu Val Met Pro Gln Ala
305                 310                 315                 320

Glu Asn Gln Asp Pro Glu Ile Lys Asp His Val Asn Ser Leu Gly Glu
                325                 330                 335

Asn Leu Lys Thr Leu Arg Leu Arg Leu Arg Arg Cys His Arg Phe Leu
            340                 345                 350

Pro Cys Glu Asn Lys Ser Lys Ala Val Glu Gln Ile Lys Asn Ala Phe
        355                 360                 365

Asn Lys Leu Gln Glu Lys Gly Ile Tyr Lys Ala Met Ser Glu Phe Asp
    370                 375                 380

Ile Phe Ile Asn Tyr Ile Glu Ala Tyr Met Thr Ile Lys Ala Arg
385                 390                 395


<210> SEQ ID NO 42
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160
```

Gly Ser Gln Val Gln Leu Gln Gln Trp Gly Ala Gly Leu Leu Lys Pro
165 170 175

Ser Glu Thr Leu Ser Leu Thr Cys Ala Val Tyr Gly Gly Ser Phe Thr
180 185 190

Thr Thr Tyr Trp Asn Trp Ile Arg Gln Pro Pro Gly Lys Gly Leu Glu
195 200 205

Trp Ile Gly Glu Val Asn Tyr Ser Gly Asn Ala Asn Tyr Asn Pro Ser
210 215 220

Leu Lys Gly Arg Val Ala Ile Ser Val Asp Thr Ser Lys Asn Gln Phe
225 230 235 240

Ser Leu Arg Leu Asn Ser Val Thr Ala Ala Asp Thr Ala Ile Tyr Tyr
245 250 255

Cys Thr Ser Arg Ile Arg Ser His Ile Ala Tyr Ser Trp Lys Gly Asp
260 265 270

Val Trp Gly Lys Gly Thr Thr Val Thr Val Ser Ser Gly Gly Gly Gly
275 280 285

Ser Asp Ile Val Met Thr Gln Thr Pro Leu Ser Leu Ser Val Thr Pro
290 295 300

Gly Gln Pro Ala Ser Ile Ser Cys Lys Ser Ser Gln Ser Leu Leu His
305 310 315 320

Thr Asp Gly Thr Thr Tyr Leu Tyr Trp Tyr Leu Gln Lys Pro Gly Gln
325 330 335

Pro Pro Gln Leu Leu Ile Tyr Glu Val Ser Asn Arg Phe Ser Gly Val
340 345 350

Pro Asp Arg Phe Ser Gly Ser Gly Ser Gly Thr Asp Phe Thr Leu Lys
355 360 365

Ile Ser Arg Val Glu Ala Glu Asp Val Gly Ile Tyr Tyr Cys Met Gln
370 375 380

Asn Ile Gln Leu Pro Trp Thr Phe Gly Gln Gly Thr Lys Val Glu Ile
385 390 395 400

Lys

<210> SEQ ID NO 43
<211> LENGTH: 575
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Val Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ile Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

-continued

```
Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Gly Ile Asn Trp Val Arg Gln Ala Pro Gly Gln Gly Leu Glu
        195                 200                 205

Trp Met Gly Trp Ile Ser Val Tyr Ser Gly Asn Thr Asn Tyr Ala Gln
    210                 215                 220

Lys Val Gln Gly Arg Val Thr Met Thr Ala Asp Thr Ser Thr Ser Thr
225                 230                 235                 240

Ala Tyr Met Asp Leu Arg Ser Leu Arg Ser Asp Asp Thr Ala Val Tyr
                245                 250                 255

Tyr Cys Ala Arg Glu Gly Ser Ser Ser Ser Gly Asp Tyr Tyr Tyr Gly
            260                 265                 270

Met Asp Val Trp Gly Gln Gly Thr Thr Val Thr Val Ser Ser Gly Gly
        275                 280                 285

Gly Gly Ser Gly Gly Gly Gly Ser Gly Gly Gly Gly Ser Asp Ile Val
    290                 295                 300

Met Thr Gln Thr Pro Leu Ser Leu Ser Val Thr Pro Gly Gln Pro Ala
305                 310                 315                 320

Ser Ile Ser Cys Lys Ser Ser Gln Ser Leu Leu His Thr Asp Gly Thr
                325                 330                 335

Thr Tyr Leu Tyr Trp Tyr Leu Gln Lys Pro Gly Gln Pro Pro Gln Leu
            340                 345                 350

Leu Ile Tyr Glu Val Ser Asn Arg Phe Ser Gly Val Pro Asp Arg Phe
        355                 360                 365

Ser Gly Ser Gly Ser Gly Thr Asp Phe Thr Leu Lys Ile Ser Arg Val
    370                 375                 380

Glu Ala Glu Asp Val Gly Ile Tyr Tyr Cys Met Gln Asn Ile Gln Leu
385                 390                 395                 400

Pro Trp Thr Phe Gly Gln Gly Thr Lys Val Glu Ile Lys Gly Gly Gly
                405                 410                 415

Gly Ser Gly Gly Gly Gly Ser Gly Gly Gly Gly Ser Thr Asp Gln Cys
            420                 425                 430

Asp Asn Phe Pro Gln Met Leu Arg Asp Leu Arg Asp Ala Phe Ser Arg
        435                 440                 445

Val Lys Thr Phe Phe Gln Thr Lys Asp Glu Val Asp Asn Leu Leu Leu
    450                 455                 460

Lys Glu Ser Leu Leu Glu Asp Phe Lys Gly Tyr Leu Gly Cys Gln Ala
465                 470                 475                 480

Leu Ser Glu Met Ile Gln Phe Tyr Leu Glu Glu Val Met Pro Gln Ala
                485                 490                 495

Glu Asn Gln Asp Pro Glu Ile Lys Asp His Val Asn Ser Leu Gly Glu
            500                 505                 510

Asn Leu Lys Thr Leu Arg Leu Arg Leu Arg Arg Cys His Arg Phe Leu
        515                 520                 525

Pro Cys Glu Asn Lys Ser Lys Ala Val Glu Gln Ile Lys Asn Ala Phe
```

530 535 540

Asn Lys Leu Gln Glu Lys Gly Ile Tyr Lys Ala Met Ser Glu Phe Asp
545 550 555 560

Ile Phe Ile Asn Tyr Ile Glu Ala Tyr Met Thr Ile Lys Ala Arg
565 570 575

<210> SEQ ID NO 44
<211> LENGTH: 573
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (193)..(199)
<223> OTHER INFORMATION: Any amino acid
<220> FEATURE:
<221> NAME/KEY: MISC_FEATURE
<222> LOCATION: (193)..(199)
<223> OTHER INFORMATION: This region may encompass 3-7 residues
<220> FEATURE:
<221> NAME/KEY: MOD_RES
<222> LOCATION: (213)..(230)
<223> OTHER INFORMATION: Any amino acid
<220> FEATURE:
<221> NAME/KEY: MISC_FEATURE
<222> LOCATION: (213)..(230)
<223> OTHER INFORMATION: This region may encompass 14-18 residues
<220> FEATURE:
<221> NAME/KEY: MOD_RES
<222> LOCATION: (263)..(273)
<223> OTHER INFORMATION: Any amino acid
<220> FEATURE:
<221> NAME/KEY: MISC_FEATURE
<222> LOCATION: (263)..(273)
<223> OTHER INFORMATION: This region may encompass 7-11 residues
<220> FEATURE:
<221> NAME/KEY: MOD_RES
<222> LOCATION: (321)..(334)
<223> OTHER INFORMATION: Any amino acid
<220> FEATURE:
<221> NAME/KEY: MISC_FEATURE
<222> LOCATION: (321)..(334)
<223> OTHER INFORMATION: This region may encompass 9-14 residues
<220> FEATURE:
<221> NAME/KEY: MOD_RES
<222> LOCATION: (350)..(358)
<223> OTHER INFORMATION: Any amino acid
<220> FEATURE:
<221> NAME/KEY: MISC_FEATURE
<222> LOCATION: (350)..(358)
<223> OTHER INFORMATION: This region may encompass 5-9 residues
<220> FEATURE:
<221> NAME/KEY: MOD_RES
<222> LOCATION: (391)..(401)
<223> OTHER INFORMATION: Any amino acid
<220> FEATURE:
<221> NAME/KEY: MISC_FEATURE
<222> LOCATION: (391)..(401)
<223> OTHER INFORMATION: This region may encompass 7-11 residues
<220> FEATURE:
<223> OTHER INFORMATION: See specification as filed for detailed description of substitutions and preferred embodiments

<400> SEQUENCE: 44

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

```
Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Thr
            180                 185                 190

Xaa Xaa Xaa Xaa Xaa Xaa Xaa Trp Ile Arg Gln Pro Pro Gly Lys Gly
        195                 200                 205

Leu Glu Trp Ile Xaa Xaa Xaa Xaa Xaa Xaa Xaa Xaa Xaa Xaa Xaa Xaa
    210                 215                 220

Xaa Xaa Xaa Xaa Xaa Xaa Arg Val Thr Ile Ser Val Asp Thr Ser Lys
225                 230                 235                 240

Asn Gln Phe Ser Leu Gln Leu Asn Ser Val Thr Ala Ala Asp Thr Ala
                245                 250                 255

Ile Tyr Tyr Cys Thr Ser Xaa Xaa Xaa Xaa Xaa Xaa Xaa Xaa Xaa Xaa
            260                 265                 270

Xaa Trp Gly Lys Gly Thr Thr Val Thr Val Gly Gly Gly Gly Ser Gly
        275                 280                 285

Gly Gly Gly Ser Gly Gly Gly Gly Ser Glu Ile Val Met Thr Gln Ser
    290                 295                 300

Pro Gly Thr Leu Ser Leu Ser Pro Gly Glu Arg Ala Thr Leu Ser Cys
305                 310                 315                 320

Xaa Xaa Xaa Xaa Xaa Xaa Xaa Xaa Xaa Xaa Xaa Xaa Xaa Xaa Trp Phe
                325                 330                 335

Gln Gln Lys Pro Gly Gln Ala Pro Arg Leu Leu Ile Tyr Xaa Xaa Xaa
            340                 345                 350

Xaa Xaa Xaa Xaa Xaa Xaa Gly Phe Pro Asp Arg Phe Ser Gly Ser Gly
        355                 360                 365

Ser Gly Thr Asp Phe Thr Leu Thr Ile Thr Arg Leu Glu Pro Glu Asp
    370                 375                 380

Phe Ala Met Tyr Tyr Cys Xaa Xaa Xaa Xaa Xaa Xaa Xaa Xaa Xaa Xaa
385                 390                 395                 400

Xaa Phe Gly Gln Gly Thr Lys Leu Glu Ile Lys Gly Gly Gly Gly Ser
                405                 410                 415

Gly Gly Gly Gly Ser Gly Gly Gly Gly Ser Thr Asp Gln Cys Asp Asn
            420                 425                 430

Phe Pro Gln Met Leu Arg Asp Leu Arg Asp Ala Phe Ser Arg Val Lys
        435                 440                 445

Thr Phe Phe Gln Thr Lys Asp Glu Leu Asp Asn Leu Leu Leu Lys Glu
    450                 455                 460

Ser Leu Leu Glu Asp Phe Lys Gly Tyr Leu Gly Cys Gln Ala Leu Ser
```

```
465                 470                 475                 480

Glu Met Ile Gln Phe Tyr Leu Glu Glu Val Met Pro Gln Ala Glu Asn
                485                 490                 495

Gln Asp Pro Glu Ile Lys Asp His Val Asn Ser Leu Gly Glu Asn Leu
            500                 505                 510

Lys Thr Leu Arg Leu Arg Leu Arg Arg Cys His Arg Phe Leu Pro Cys
        515                 520                 525

Glu Asn Lys Ser Lys Ala Val Glu Gln Ile Lys Asn Ala Phe Asn Lys
    530                 535                 540

Leu Gln Glu Lys Gly Ile Tyr Lys Ala Met Ser Glu Phe Asp Ile Phe
545                 550                 555                 560

Ile Asn Tyr Ile Glu Ala Tyr Met Thr Ile Lys Ala Arg
                565                 570


<210> SEQ ID NO 45
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (193)..(199)
<223> OTHER INFORMATION: Any amino acid
<220> FEATURE:
<221> NAME/KEY: MISC_FEATURE
<222> LOCATION: (193)..(199)
<223> OTHER INFORMATION: This region may encompass 3-7 residues
<220> FEATURE:
<221> NAME/KEY: MOD_RES
<222> LOCATION: (213)..(230)
<223> OTHER INFORMATION: Any amino acid
<220> FEATURE:
<221> NAME/KEY: MISC_FEATURE
<222> LOCATION: (213)..(230)
<223> OTHER INFORMATION: This region may encompass 14-18 residues
<220> FEATURE:
<221> NAME/KEY: MOD_RES
<222> LOCATION: (263)..(273)
<223> OTHER INFORMATION: Any amino acid
<220> FEATURE:
<221> NAME/KEY: MISC_FEATURE
<222> LOCATION: (263)..(273)
<223> OTHER INFORMATION: This region may encompass 7-11 residues
<220> FEATURE:
<221> NAME/KEY: MOD_RES
<222> LOCATION: (321)..(334)
<223> OTHER INFORMATION: Any amino acid
<220> FEATURE:
<221> NAME/KEY: MISC_FEATURE
<222> LOCATION: (321)..(334)
<223> OTHER INFORMATION: This region may encompass 9-14 residues
<220> FEATURE:
<221> NAME/KEY: MOD_RES
<222> LOCATION: (350)..(358)
<223> OTHER INFORMATION: Any amino acid
<220> FEATURE:
<221> NAME/KEY: MISC_FEATURE
<222> LOCATION: (350)..(358)
<223> OTHER INFORMATION: This region may encompass 5-9 residues
<220> FEATURE:
<221> NAME/KEY: MOD_RES
<222> LOCATION: (391)..(401)
<223> OTHER INFORMATION: Any amino acid
<220> FEATURE:
<221> NAME/KEY: MISC_FEATURE
<222> LOCATION: (391)..(401)
<223> OTHER INFORMATION: This region may encompass 7-11 residues
<220> FEATURE:
<223> OTHER INFORMATION: See specification as filed for detailed
      description of substitutions and preferred embodiments
```

-continued

<400> SEQUENCE: 45

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Thr
            180                 185                 190

Xaa Xaa Xaa Xaa Xaa Xaa Xaa Trp Ile Arg Gln Pro Pro Gly Lys Gly
        195                 200                 205

Leu Glu Trp Ile Xaa Xaa Xaa Xaa Xaa Xaa Xaa Xaa Xaa Xaa Xaa Xaa
    210                 215                 220

Xaa Xaa Xaa Xaa Xaa Xaa Arg Val Thr Ile Ser Val Asp Thr Ser Lys
225                 230                 235                 240

Asn Gln Phe Ser Leu Gln Leu Asn Ser Val Thr Ala Ala Asp Thr Ala
                245                 250                 255

Ile Tyr Tyr Cys Thr Ser Xaa Xaa Xaa Xaa Xaa Xaa Xaa Xaa Xaa Xaa
            260                 265                 270

Xaa Trp Gly Lys Gly Thr Thr Val Thr Val Gly Gly Gly Gly Ser Gly
        275                 280                 285

Gly Gly Gly Ser Gly Gly Gly Gly Ser Glu Ile Val Met Thr Gln Ser
    290                 295                 300

Pro Gly Thr Leu Ser Leu Ser Pro Gly Glu Arg Ala Thr Leu Ser Cys
305                 310                 315                 320

Xaa Xaa Xaa Xaa Xaa Xaa Xaa Xaa Xaa Xaa Xaa Xaa Xaa Xaa Trp Phe
                325                 330                 335

Gln Gln Lys Pro Gly Gln Ala Pro Arg Leu Leu Ile Tyr Xaa Xaa Xaa
            340                 345                 350

Xaa Xaa Xaa Xaa Xaa Xaa Gly Phe Pro Asp Arg Phe Ser Gly Ser Gly
        355                 360                 365

Ser Gly Thr Asp Phe Thr Leu Thr Ile Thr Arg Leu Glu Pro Glu Asp
    370                 375                 380

Phe Ala Met Tyr Tyr Cys Xaa Xaa Xaa Xaa Xaa Xaa Xaa Xaa Xaa Xaa
385                 390                 395                 400

Xaa Phe Gly Gln Gly Thr Lys Leu Glu Ile Lys Gly Gly Gly Gly Ser
```

```
                405                 410                 415

Gly Gly Gly Gly Ser Gly Gly Gly Gly Ser Thr Asp Gln Cys Asp Asn
            420                 425                 430

Phe Pro Gln Met Leu Arg Asp Leu Arg Asp Ala Phe Ser Arg Val Lys
        435                 440                 445

Thr Phe Phe Gln Thr Lys Asp Glu Leu Asp Asn Leu Leu Leu Lys Glu
    450                 455                 460

Ser Leu Leu Glu Asp Phe Lys Gly Tyr Leu Gly Cys Gln Ala Leu Ser
465                 470                 475                 480

Glu Met Ile Gln Phe Tyr Leu Glu Glu Val Met Pro Gln Ala Glu Asn
                485                 490                 495

Gln Asp Pro Glu Ala Lys Asp His Val Asn Ser Leu Gly Glu Asn Leu
            500                 505                 510

Lys Thr Leu Arg Leu Arg Leu Arg Arg Cys His Arg Phe Leu Pro Cys
        515                 520                 525

Glu Asn Lys Ser Lys Ala Val Glu Gln Ile Lys Asn Ala Phe Asn Lys
    530                 535                 540

Leu Gln Glu Lys Gly Ile Tyr Lys Ala Met Ser Glu Phe Asp Ile Phe
545                 550                 555                 560

Ile Asn Tyr Ile Glu Ala Tyr Met Thr Ile Lys Ala Arg
                565                 570


<210> SEQ ID NO 46
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(37)
<223> OTHER INFORMATION: Any amino acid
<220> FEATURE:
<221> NAME/KEY: MISC_FEATURE
<222> LOCATION: (31)..(37)
<223> OTHER INFORMATION: This region may encompass 3-7 residues
<220> FEATURE:
<221> NAME/KEY: MOD_RES
<222> LOCATION: (52)..(62)
<223> OTHER INFORMATION: Any amino acid
<220> FEATURE:
<221> NAME/KEY: MISC_FEATURE
<222> LOCATION: (52)..(62)
<223> OTHER INFORMATION: This region may encompass 7-11 residues
<220> FEATURE:
<221> NAME/KEY: MOD_RES
<222> LOCATION: (95)..(105)
<223> OTHER INFORMATION: Any amino acid
<220> FEATURE:
<221> NAME/KEY: MISC_FEATURE
<222> LOCATION: (95)..(105)
<223> OTHER INFORMATION: This region may encompass 7-11 residues
<220> FEATURE:
<221> NAME/KEY: MOD_RES
<222> LOCATION: (150)..(163)
<223> OTHER INFORMATION: Any amino acid
<220> FEATURE:
<221> NAME/KEY: MISC_FEATURE
<222> LOCATION: (150)..(163)
<223> OTHER INFORMATION: This region may encompass 9-14 residues
<220> FEATURE:
<221> NAME/KEY: MOD_RES
<222> LOCATION: (179)..(187)
<223> OTHER INFORMATION: Any amino acid
<220> FEATURE:
<221> NAME/KEY: MISC_FEATURE
<222> LOCATION: (179)..(187)
```

```
<223> OTHER INFORMATION: This region may encompass 5-9 residues
<220> FEATURE:
<221> NAME/KEY: MOD_RES
<222> LOCATION: (220)..(230)
<223> OTHER INFORMATION: Any amino acid
<220> FEATURE:
<221> NAME/KEY: MISC_FEATURE
<222> LOCATION: (220)..(230)
<223> OTHER INFORMATION: This region may encompass 7-11 residues
<220> FEATURE:
<223> OTHER INFORMATION: See specification as filed for detailed
      description of substitutions and preferred embodiments

<400> SEQUENCE: 46

Gln Val Gln Leu Gln Gln Trp Gly Ala Gly Leu Leu Lys Pro Ser Glu
1               5                   10                  15

Thr Leu Arg Leu Thr Cys Ala Val Tyr Gly Gly Ser Phe Thr Xaa Xaa
            20                  25                  30

Xaa Xaa Xaa Xaa Xaa Trp Ile Arg Gln Pro Pro Gly Lys Gly Leu Glu
        35                  40                  45

Trp Ile Gly Xaa Xaa Xaa Xaa Xaa Xaa Xaa Xaa Xaa Xaa Xaa Arg Val
    50                  55                  60

Thr Ile Ser Val Asp Thr Ser Lys Asn Gln Phe Ser Leu Gln Leu Asn
65                  70                  75                  80

Ser Val Thr Ala Ala Asp Thr Ala Ile Tyr Tyr Cys Thr Ser Xaa Xaa
                85                  90                  95

Xaa Xaa Xaa Xaa Xaa Xaa Xaa Xaa Xaa Trp Lys Gly Asp Val Trp Gly
            100                 105                 110

Lys Gly Thr Thr Val Thr Val Ser Ser Gly Gly Gly Gly Ser Glu Ile
        115                 120                 125

Val Met Thr Gln Ser Pro Gly Thr Leu Ser Leu Ser Pro Gly Glu Arg
    130                 135                 140

Ala Thr Leu Ser Cys Xaa Xaa Xaa Xaa Xaa Xaa Xaa Xaa Xaa Xaa Xaa
145                 150                 155                 160

Xaa Xaa Xaa Trp Phe Gln Gln Lys Pro Gly Gln Ala Pro Arg Leu Leu
                165                 170                 175

Ile Tyr Xaa Xaa Xaa Xaa Xaa Xaa Xaa Xaa Gly Phe Pro Asp Arg
            180                 185                 190

Phe Ser Gly Ser Gly Ser Gly Thr Asp Phe Thr Leu Thr Ile Thr Arg
        195                 200                 205

Leu Glu Pro Glu Asp Phe Ala Met Tyr Tyr Cys Xaa Xaa Xaa Xaa Xaa
    210                 215                 220

Xaa Xaa Xaa Xaa Xaa Xaa Phe Gly Gln Gly Thr Lys Leu Glu Ile Lys
225                 230                 235                 240

Gly Gly Gly Gly Ser Gly Gly Gly Gly Ser Gly Gly Gly Gly Ser Thr
                245                 250                 255

Asp Gln Cys Asp Asn Phe Pro Gln Met Leu Arg Asp Leu Arg Asp Ala
            260                 265                 270

Phe Ser Arg Val Lys Thr Phe Phe Gln Thr Lys Asp Glu Leu Asp Asn
        275                 280                 285

Leu Leu Leu Lys Glu Ser Leu Leu Glu Asp Phe Lys Gly Tyr Leu Gly
    290                 295                 300

Cys Gln Ala Leu Ser Glu Met Ile Gln Phe Tyr Leu Glu Glu Val Met
305                 310                 315                 320

Pro Gln Ala Glu Asn Gln Asp Pro Glu Ile Lys Asp His Val Asn Ser
                325                 330                 335

Leu Gly Glu Asn Leu Lys Thr Leu Arg Leu Arg Leu Arg Arg Cys His
```

```
            340                 345                 350

Arg Phe Leu Pro Cys Glu Asn Lys Ser Lys Ala Val Glu Gln Ile Lys
        355                 360                 365

Asn Ala Phe Asn Lys Leu Gln Glu Lys Gly Ile Tyr Lys Ala Met Ser
    370                 375                 380

Glu Phe Asp Ile Phe Ile Asn Tyr Ile Glu Ala Tyr Met Thr Ile Lys
385                 390                 395                 400

Ala Arg


<210> SEQ ID NO 47
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (192)..(198)
<223> OTHER INFORMATION: Any amino acid
<220> FEATURE:
<221> NAME/KEY: MISC_FEATURE
<222> LOCATION: (192)..(198)
<223> OTHER INFORMATION: This region may encompass 3-7 residues
<220> FEATURE:
<221> NAME/KEY: MOD_RES
<222> LOCATION: (213)..(223)
<223> OTHER INFORMATION: Any amino acid
<220> FEATURE:
<221> NAME/KEY: MISC_FEATURE
<222> LOCATION: (213)..(223)
<223> OTHER INFORMATION: This region may encompass 7-11 residues
<220> FEATURE:
<221> NAME/KEY: MOD_RES
<222> LOCATION: (256)..(266)
<223> OTHER INFORMATION: Any amino acid
<220> FEATURE:
<221> NAME/KEY: MISC_FEATURE
<222> LOCATION: (256)..(266)
<223> OTHER INFORMATION: This region may encompass 7-11 residues
<220> FEATURE:
<221> NAME/KEY: MOD_RES
<222> LOCATION: (311)..(324)
<223> OTHER INFORMATION: Any amino acid
<220> FEATURE:
<221> NAME/KEY: MISC_FEATURE
<222> LOCATION: (311)..(324)
<223> OTHER INFORMATION: This region may encompass 9-14 residues
<220> FEATURE:
<221> NAME/KEY: MOD_RES
<222> LOCATION: (340)..(348)
<223> OTHER INFORMATION: Any amino acid
<220> FEATURE:
<221> NAME/KEY: MISC_FEATURE
<222> LOCATION: (340)..(348)
<223> OTHER INFORMATION: This region may encompass 5-9 residues
<220> FEATURE:
<221> NAME/KEY: MOD_RES
<222> LOCATION: (381)..(391)
<223> OTHER INFORMATION: Any amino acid
<220> FEATURE:
<221> NAME/KEY: MISC_FEATURE
<222> LOCATION: (381)..(391)
<223> OTHER INFORMATION: This region may encompass 7-11 residues
<220> FEATURE:
<223> OTHER INFORMATION: See specification as filed for detailed
      description of substitutions and preferred embodiments

<400> SEQUENCE: 47

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
```

-continued

```
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Xaa
            180                 185                 190

Xaa Xaa Xaa Xaa Xaa Xaa Trp Ile Arg Gln Pro Pro Gly Lys Gly Leu
        195                 200                 205

Glu Trp Ile Gly Xaa Xaa Xaa Xaa Xaa Xaa Xaa Xaa Xaa Xaa Xaa Arg
    210                 215                 220

Val Thr Ile Ser Val Asp Thr Ser Lys Asn Gln Phe Ser Leu Gln Leu
225                 230                 235                 240

Asn Ser Val Thr Ala Ala Asp Thr Ala Ile Tyr Tyr Cys Thr Ser Xaa
                245                 250                 255

Xaa Xaa Xaa Xaa Xaa Xaa Xaa Xaa Xaa Xaa Trp Lys Gly Asp Val Trp
            260                 265                 270

Gly Lys Gly Thr Thr Val Thr Val Ser Ser Gly Gly Gly Gly Ser Glu
        275                 280                 285

Ile Val Met Thr Gln Ser Pro Gly Thr Leu Ser Leu Ser Pro Gly Glu
    290                 295                 300

Arg Ala Thr Leu Ser Cys Xaa Xaa Xaa Xaa Xaa Xaa Xaa Xaa Xaa Xaa
305                 310                 315                 320

Xaa Xaa Xaa Xaa Trp Phe Gln Gln Lys Pro Gly Gln Ala Pro Arg Leu
                325                 330                 335

Leu Ile Tyr Xaa Xaa Xaa Xaa Xaa Xaa Xaa Xaa Xaa Gly Phe Pro Asp
            340                 345                 350

Arg Phe Ser Gly Ser Gly Ser Gly Thr Asp Phe Thr Leu Thr Ile Thr
        355                 360                 365

Arg Leu Glu Pro Glu Asp Phe Ala Met Tyr Tyr Cys Xaa Xaa Xaa Xaa
    370                 375                 380

Xaa Xaa Xaa Xaa Xaa Xaa Xaa Phe Gly Gln Gly Thr Lys Leu Glu Ile
385                 390                 395                 400

Lys Asp Tyr Lys Asp Asp Asp Asp Lys
                405
```

<210> SEQ ID NO 48
<211> LENGTH: 402
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (31)..(37)
<223> OTHER INFORMATION: Any amino acid
<220> FEATURE:
<221> NAME/KEY: MISC_FEATURE
<222> LOCATION: (31)..(37)
<223> OTHER INFORMATION: This region may encompass 3-7 residues
<220> FEATURE:
<221> NAME/KEY: MOD_RES
<222> LOCATION: (52)..(62)
<223> OTHER INFORMATION: Any amino acid
<220> FEATURE:
<221> NAME/KEY: MISC_FEATURE
<222> LOCATION: (52)..(62)
<223> OTHER INFORMATION: This region may encompass 7-11 residues
<220> FEATURE:
<221> NAME/KEY: MOD_RES
<222> LOCATION: (95)..(105)
<223> OTHER INFORMATION: Any amino acid
<220> FEATURE:
<221> NAME/KEY: MISC_FEATURE
<222> LOCATION: (95)..(105)
<223> OTHER INFORMATION: This region may encompass 7-11 residues
<220> FEATURE:
<221> NAME/KEY: MOD_RES
<222> LOCATION: (150)..(163)
<223> OTHER INFORMATION: Any amino acid
<220> FEATURE:
<221> NAME/KEY: MISC_FEATURE
<222> LOCATION: (150)..(163)
<223> OTHER INFORMATION: This region may encompass 9-14 residues
<220> FEATURE:
<221> NAME/KEY: MOD_RES
<222> LOCATION: (179)..(187)
<223> OTHER INFORMATION: Any amino acid
<220> FEATURE:
<221> NAME/KEY: MISC_FEATURE
<222> LOCATION: (179)..(187)
<223> OTHER INFORMATION: This region may encompass 5-9 residues
<220> FEATURE:
<221> NAME/KEY: MOD_RES
<222> LOCATION: (220)..(230)
<223> OTHER INFORMATION: Any amino acid
<220> FEATURE:
<221> NAME/KEY: MISC_FEATURE
<222> LOCATION: (220)..(230)
<223> OTHER INFORMATION: This region may encompass 7-11 residues
<220> FEATURE:
<223> OTHER INFORMATION: See specification as filed for detailed
description of substitutions and preferred embodiments

<400> SEQUENCE: 48

```
Gln Val Gln Leu Gln Gln Trp Gly Ala Gly Leu Leu Lys Pro Ser Glu
1               5                   10                  15

Thr Leu Arg Leu Thr Cys Ala Val Tyr Gly Gly Ser Phe Thr Xaa Xaa
            20                  25                  30

Xaa Xaa Xaa Xaa Xaa Trp Ile Arg Gln Pro Pro Gly Lys Gly Leu Glu
        35                  40                  45

Trp Ile Gly Xaa Xaa Xaa Xaa Xaa Xaa Xaa Xaa Xaa Xaa Xaa Arg Val
    50                  55                  60

Thr Ile Ser Val Asp Thr Ser Lys Asn Gln Phe Ser Leu Gln Leu Asn
65                  70                  75                  80

Ser Val Thr Ala Ala Asp Thr Ala Ile Tyr Tyr Cys Thr Ser Xaa Xaa
                85                  90                  95

Xaa Xaa Xaa Xaa Xaa Xaa Xaa Xaa Xaa Trp Lys Gly Asp Val Trp Gly
            100                 105                 110

Lys Gly Thr Thr Val Thr Val Ser Ser Gly Gly Gly Gly Ser Glu Ile
```

```
        115                 120                 125

Val Met Thr Gln Ser Pro Gly Thr Leu Ser Leu Ser Pro Gly Glu Arg
    130                 135                 140

Ala Thr Leu Ser Cys Xaa Xaa Xaa Xaa Xaa Xaa Xaa Xaa Xaa Xaa Xaa
145                 150                 155                 160

Xaa Xaa Xaa Trp Phe Gln Gln Lys Pro Gly Gln Ala Pro Arg Leu Leu
                165                 170                 175

Ile Tyr Xaa Xaa Xaa Xaa Xaa Xaa Xaa Xaa Gly Phe Pro Asp Arg
            180                 185                 190

Phe Ser Gly Ser Gly Ser Gly Thr Asp Phe Thr Leu Thr Ile Thr Arg
        195                 200                 205

Leu Glu Pro Glu Asp Phe Ala Met Tyr Tyr Cys Xaa Xaa Xaa Xaa Xaa
    210                 215                 220

Xaa Xaa Xaa Xaa Xaa Xaa Phe Gly Gln Gly Thr Lys Leu Glu Ile Lys
225                 230                 235                 240

Gly Gly Gly Gly Ser Gly Gly Gly Gly Ser Gly Gly Gly Gly Ser Thr
                245                 250                 255

Asp Gln Cys Asp Asn Phe Pro Gln Met Leu Arg Asp Leu Arg Asp Ala
            260                 265                 270

Phe Ser Arg Val Lys Thr Phe Phe Gln Thr Lys Asp Glu Val Asp Asn
        275                 280                 285

Leu Leu Leu Lys Glu Ser Leu Leu Glu Asp Phe Lys Gly Tyr Leu Gly
    290                 295                 300

Cys Gln Ala Leu Ser Glu Met Ile Gln Phe Tyr Leu Glu Glu Val Met
305                 310                 315                 320

Pro Gln Ala Glu Asn Gln Asp Pro Glu Ile Lys Asp His Val Asn Ser
                325                 330                 335

Leu Gly Glu Asn Leu Lys Thr Leu Arg Leu Arg Leu Arg Arg Cys His
            340                 345                 350

Arg Phe Leu Pro Cys Glu Asn Lys Ser Lys Ala Val Glu Gln Ile Lys
        355                 360                 365

Asn Ala Phe Asn Lys Leu Gln Glu Lys Gly Ile Tyr Lys Ala Met Ser
    370                 375                 380

Glu Phe Asp Ile Phe Ile Asn Tyr Ile Glu Ala Tyr Met Thr Ile Lys
385                 390                 395                 400

Ala Arg
```

<210> SEQ ID NO 49
<211> LENGTH: 409
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (192)..(198)
<223> OTHER INFORMATION: Any amino acid
<220> FEATURE:
<221> NAME/KEY: MISC_FEATURE
<222> LOCATION: (192)..(198)
<223> OTHER INFORMATION: This region may encompass 3-7 residues
<220> FEATURE:
<221> NAME/KEY: MOD_RES
<222> LOCATION: (213)..(223)
<223> OTHER INFORMATION: Any amino acid
<220> FEATURE:
<221> NAME/KEY: MISC_FEATURE
<222> LOCATION: (213)..(223)
<223> OTHER INFORMATION: This region may encompass 7-11 residues
<220> FEATURE:
<221> NAME/KEY: MOD_RES
<222> LOCATION: (256)..(266)
<223> OTHER INFORMATION: Any amino acid
<220> FEATURE:
<221> NAME/KEY: MISC_FEATURE
<222> LOCATION: (256)..(266)
<223> OTHER INFORMATION: This region may encompass 7-11 residues
<220> FEATURE:
<221> NAME/KEY: MOD_RES
<222> LOCATION: (311)..(324)
<223> OTHER INFORMATION: Any amino acid
<220> FEATURE:
<221> NAME/KEY: MISC_FEATURE
<222> LOCATION: (311)..(324)
<223> OTHER INFORMATION: This region may encompass 9-14 residues
<220> FEATURE:
<221> NAME/KEY: MOD_RES
<222> LOCATION: (340)..(348)
<223> OTHER INFORMATION: Any amino acid
<220> FEATURE:
<221> NAME/KEY: MISC_FEATURE
<222> LOCATION: (340)..(348)
<223> OTHER INFORMATION: This region may encompass 5-9 residues
<220> FEATURE:
<221> NAME/KEY: MOD_RES
<222> LOCATION: (381)..(391)
<223> OTHER INFORMATION: Any amino acid
<220> FEATURE:
<221> NAME/KEY: MISC_FEATURE
<222> LOCATION: (381)..(391)
<223> OTHER INFORMATION: This region may encompass 7-11 residues
<220> FEATURE:
<223> OTHER INFORMATION: See specification as filed for detailed
description of substitutions and preferred embodiments

<400> SEQUENCE: 49

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Xaa
            180                 185                 190

Xaa Xaa Xaa Xaa Xaa Xaa Trp Ile Arg Gln Pro Pro Gly Lys Gly Leu
        195                 200                 205

Glu Trp Ile Gly Xaa Xaa Xaa Xaa Xaa Xaa Xaa Xaa Xaa Xaa Xaa Arg
    210                 215                 220
```

```
Val Thr Ile Ser Val Asp Thr Ser Lys Asn Gln Phe Ser Leu Gln Leu
225                 230                 235                 240

Asn Ser Val Thr Ala Ala Asp Thr Ala Ile Tyr Tyr Cys Thr Ser Xaa
                245                 250                 255

Xaa Xaa Xaa Xaa Xaa Xaa Xaa Xaa Xaa Xaa Trp Lys Gly Asp Val Trp
            260                 265                 270

Gly Lys Gly Thr Thr Val Thr Val Ser Ser Gly Gly Gly Gly Ser Glu
        275                 280                 285

Ile Val Met Thr Gln Ser Pro Gly Thr Leu Ser Leu Ser Pro Gly Glu
    290                 295                 300

Arg Ala Thr Leu Ser Cys Xaa Xaa Xaa Xaa Xaa Xaa Xaa Xaa Xaa Xaa
305                 310                 315                 320

Xaa Xaa Xaa Xaa Trp Phe Gln Gln Lys Pro Gly Gln Ala Pro Arg Leu
                325                 330                 335

Leu Ile Tyr Xaa Xaa Xaa Xaa Xaa Xaa Xaa Xaa Xaa Gly Phe Pro Asp
            340                 345                 350

Arg Phe Ser Gly Ser Gly Ser Gly Thr Asp Phe Thr Leu Thr Ile Thr
        355                 360                 365

Arg Leu Glu Pro Glu Asp Phe Ala Met Tyr Tyr Cys Xaa Xaa Xaa Xaa
    370                 375                 380

Xaa Xaa Xaa Xaa Xaa Xaa Xaa Phe Gly Gln Gly Thr Lys Leu Glu Ile
385                 390                 395                 400

Lys Asp Tyr Lys Asp Asp Asp Asp Lys
                405
```

<210> SEQ ID NO 50
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (31)..(37)
<223> OTHER INFORMATION: Any amino acid
<220> FEATURE:
<221> NAME/KEY: MISC_FEATURE
<222> LOCATION: (31)..(37)
<223> OTHER INFORMATION: This region may encompass 3-7 residues
<220> FEATURE:
<221> NAME/KEY: MOD_RES
<222> LOCATION: (52)..(62)
<223> OTHER INFORMATION: Any amino acid
<220> FEATURE:
<221> NAME/KEY: MISC_FEATURE
<222> LOCATION: (52)..(62)
<223> OTHER INFORMATION: This region may encompass 7-11 residues
<220> FEATURE:
<221> NAME/KEY: MOD_RES
<222> LOCATION: (95)..(105)
<223> OTHER INFORMATION: Any amino acid
<220> FEATURE:
<221> NAME/KEY: MISC_FEATURE
<222> LOCATION: (95)..(105)
<223> OTHER INFORMATION: This region may encompass 7-11 residues
<220> FEATURE:
<221> NAME/KEY: MOD_RES
<222> LOCATION: (150)..(163)
<223> OTHER INFORMATION: Any amino acid
<220> FEATURE:
<221> NAME/KEY: MISC_FEATURE
<222> LOCATION: (150)..(163)
<223> OTHER INFORMATION: This region may encompass 9-14 residues
<220> FEATURE:
<221> NAME/KEY: MOD_RES
<222> LOCATION: (179)..(187)
<223> OTHER INFORMATION: Any amino acid
<220> FEATURE:
<221> NAME/KEY: MISC_FEATURE
<222> LOCATION: (179)..(187)
<223> OTHER INFORMATION: This region may encompass 5-9 residues
<220> FEATURE:
<221> NAME/KEY: MOD_RES
<222> LOCATION: (220)..(230)
<223> OTHER INFORMATION: Any amino acid
<220> FEATURE:
<221> NAME/KEY: MISC_FEATURE
<222> LOCATION: (220)..(230)
<223> OTHER INFORMATION: This region may encompass 7-11 residues
<220> FEATURE:
<223> OTHER INFORMATION: See specification as filed for detailed
description of substitutions and preferred embodiments

<400> SEQUENCE: 50

Gln Val Gln Leu Gln Gln Trp Gly Ala Gly Leu Leu Lys Pro Ser Glu
1 5 10 15

Thr Leu Arg Leu Thr Cys Ala Val Tyr Gly Gly Ser Phe Thr Xaa Xaa
20 25 30

Xaa Xaa Xaa Xaa Xaa Trp Ile Arg Gln Pro Pro Gly Lys Gly Leu Glu
35 40 45

Trp Ile Gly Xaa Xaa Xaa Xaa Xaa Xaa Xaa Xaa Xaa Xaa Xaa Arg Val
50 55 60

Thr Ile Ser Val Asp Thr Ser Lys Asn Gln Phe Ser Leu Gln Leu Asn
65 70 75 80

Ser Val Thr Ala Ala Asp Thr Ala Ile Tyr Tyr Cys Thr Ser Xaa Xaa
85 90 95

Xaa Xaa Xaa Xaa Xaa Xaa Xaa Xaa Xaa Trp Lys Gly Asp Val Trp Gly
100 105 110

Lys Gly Thr Thr Val Thr Val Ser Ser Gly Gly Gly Gly Ser Glu Ile
115 120 125

Val Met Thr Gln Ser Pro Gly Thr Leu Ser Leu Ser Pro Gly Glu Arg
130 135 140

Ala Thr Leu Ser Cys Xaa Xaa Xaa Xaa Xaa Xaa Xaa Xaa Xaa Xaa Xaa
145 150 155 160

Xaa Xaa Xaa Trp Phe Gln Gln Lys Pro Gly Gln Ala Pro Arg Leu Leu
165 170 175

Ile Tyr Xaa Xaa Xaa Xaa Xaa Xaa Xaa Xaa Gly Phe Pro Asp Arg
180 185 190

Phe Ser Gly Ser Gly Ser Gly Thr Asp Phe Thr Leu Thr Ile Thr Arg
195 200 205

Leu Glu Pro Glu Asp Phe Ala Met Tyr Tyr Cys Xaa Xaa Xaa Xaa Xaa
210 215 220

Xaa Xaa Xaa Xaa Xaa Xaa Phe Gly Gln Gly Thr Lys Leu Glu Ile Lys
225 230 235 240

Gly Gly Gly Gly Ser Gly Gly Gly Gly Ser Gly Gly Gly Gly Ser Thr
245 250 255

Asp Gln Cys Asp Asn Phe Pro Gln Met Leu Arg Asp Leu Arg Asp Ala
260 265 270

Phe Ser Arg Val Lys Thr Phe Phe Gln Thr Lys Asp Glu Leu Asp Asn
275 280 285

Leu Leu Leu Lys Glu Ser Leu Leu Glu Asp Phe Lys Gly Tyr Leu Gly
290 295 300

Cys Gln Ala Leu Ser Glu Met Ile Gln Phe Tyr Leu Glu Glu Val Met
305 310 315 320

```
Pro Gln Ala Glu Asn Gln Asp Pro Glu Ala Lys Asp His Val Asn Ser
                325                 330                 335

Leu Gly Glu Asn Leu Lys Thr Leu Arg Leu Arg Leu Arg Arg Cys His
            340                 345                 350

Arg Phe Leu Pro Cys Glu Asn Lys Ser Lys Ala Val Glu Gln Ile Lys
        355                 360                 365

Asn Ala Phe Asn Lys Leu Gln Glu Lys Gly Ile Tyr Lys Ala Met Ser
    370                 375                 380

Glu Phe Asp Ile Phe Ile Asn Tyr Ile Glu Ala Tyr Met Thr Ile Lys
385                 390                 395                 400

Ala Arg


<210> SEQ ID NO 51
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (192)..(198)
<223> OTHER INFORMATION: Any amino acid
<220> FEATURE:
<221> NAME/KEY: MISC_FEATURE
<222> LOCATION: (192)..(198)
<223> OTHER INFORMATION: This region may encompass 3-7 residues
<220> FEATURE:
<221> NAME/KEY: MOD_RES
<222> LOCATION: (213)..(223)
<223> OTHER INFORMATION: Any amino acid
<220> FEATURE:
<221> NAME/KEY: MISC_FEATURE
<222> LOCATION: (213)..(223)
<223> OTHER INFORMATION: This region may encompass 7-11 residues
<220> FEATURE:
<221> NAME/KEY: MOD_RES
<222> LOCATION: (256)..(266)
<223> OTHER INFORMATION: Any amino acid
<220> FEATURE:
<221> NAME/KEY: MISC_FEATURE
<222> LOCATION: (256)..(266)
<223> OTHER INFORMATION: This region may encompass 7-11 residues
<220> FEATURE:
<221> NAME/KEY: MOD_RES
<222> LOCATION: (311)..(324)
<223> OTHER INFORMATION: Any amino acid
<220> FEATURE:
<221> NAME/KEY: MISC_FEATURE
<222> LOCATION: (311)..(324)
<223> OTHER INFORMATION: This region may encompass 9-14 residues
<220> FEATURE:
<221> NAME/KEY: MOD_RES
<222> LOCATION: (340)..(348)
<223> OTHER INFORMATION: Any amino acid
<220> FEATURE:
<221> NAME/KEY: MISC_FEATURE
<222> LOCATION: (340)..(348)
<223> OTHER INFORMATION: This region may encompass 5-9 residues
<220> FEATURE:
<221> NAME/KEY: MOD_RES
<222> LOCATION: (381)..(391)
<223> OTHER INFORMATION: Any amino acid
<220> FEATURE:
<221> NAME/KEY: MISC_FEATURE
<222> LOCATION: (381)..(391)
<223> OTHER INFORMATION: This region may encompass 7-11 residues
<220> FEATURE:
<223> OTHER INFORMATION: See specification as filed for detailed
      description of substitutions and preferred embodiments

<400> SEQUENCE: 51
```

-continued

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Xaa
            180                 185                 190

Xaa Xaa Xaa Xaa Xaa Xaa Trp Ile Arg Gln Pro Pro Gly Lys Gly Leu
        195                 200                 205

Glu Trp Ile Gly Xaa Xaa Xaa Xaa Xaa Xaa Xaa Xaa Xaa Xaa Xaa Arg
    210                 215                 220

Val Thr Ile Ser Val Asp Thr Ser Lys Asn Gln Phe Ser Leu Gln Leu
225                 230                 235                 240

Asn Ser Val Thr Ala Ala Asp Thr Ala Ile Tyr Tyr Cys Thr Ser Xaa
                245                 250                 255

Xaa Xaa Xaa Xaa Xaa Xaa Xaa Xaa Xaa Xaa Trp Lys Gly Asp Val Trp
            260                 265                 270

Gly Lys Gly Thr Thr Val Thr Val Ser Ser Gly Gly Gly Gly Ser Glu
        275                 280                 285

Ile Val Met Thr Gln Ser Pro Gly Thr Leu Ser Leu Ser Pro Gly Glu
    290                 295                 300

Arg Ala Thr Leu Ser Cys Xaa Xaa Xaa Xaa Xaa Xaa Xaa Xaa Xaa Xaa
305                 310                 315                 320

Xaa Xaa Xaa Xaa Trp Phe Gln Gln Lys Pro Gly Gln Ala Pro Arg Leu
                325                 330                 335

Leu Ile Tyr Xaa Xaa Xaa Xaa Xaa Xaa Xaa Xaa Xaa Gly Phe Pro Asp
            340                 345                 350

Arg Phe Ser Gly Ser Gly Ser Gly Thr Asp Phe Thr Leu Thr Ile Thr
        355                 360                 365

Arg Leu Glu Pro Glu Asp Phe Ala Met Tyr Tyr Cys Xaa Xaa Xaa Xaa
    370                 375                 380

Xaa Xaa Xaa Xaa Xaa Xaa Xaa Phe Gly Gln Gly Thr Lys Leu Glu Ile
385                 390                 395                 400

Lys Asp Tyr Lys Asp Asp Asp Asp Lys
                405
```

<210> SEQ ID NO 52
<211> LENGTH: 569
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Gly Gly Gly Gly Ser Gly Gly Gly Gly Ser Glu Ile Val Met Thr
    290                 295                 300

Gln Ser Pro Gly Thr Leu Ser Leu Ser Pro Gly Glu Arg Ala Thr Leu
305                 310                 315                 320

Ser Cys Arg Ala Ser Gln Ser Val Pro Arg Asn Tyr Ile Gly Trp Phe
                325                 330                 335

Gln Gln Lys Pro Gly Gln Ala Pro Arg Leu Leu Ile Tyr Gly Ala Ser
            340                 345                 350

Ser Arg Ala Ala Gly Phe Pro Asp Arg Phe Ser Gly Ser Gly Ser Gly
        355                 360                 365
```

Thr Asp Phe Thr Leu Thr Ile Thr Arg Leu Glu Pro Glu Asp Phe Ala
370 375 380

Met Tyr Tyr Cys His Gln Tyr Asp Arg Leu Pro Tyr Thr Phe Gly Gln
385 390 395 400

Gly Thr Lys Leu Glu Ile Lys Gly Gly Gly Gly Ser Gly Gly Gly Gly
405 410 415

Ser Gly Gly Gly Gly Ser Thr Asp Gln Cys Asp Asn Phe Pro Gln Met
420 425 430

Leu Arg Asp Leu Arg Asp Ala Phe Ser Arg Val Lys Thr Phe Phe Gln
435 440 445

Thr Lys Asp Glu Leu Asp Asn Leu Leu Leu Lys Glu Ser Leu Leu Glu
450 455 460

Asp Phe Lys Gly Tyr Leu Gly Cys Gln Ala Leu Ser Glu Met Ile Gln
465 470 475 480

Phe Tyr Leu Glu Glu Val Met Pro Gln Ala Glu Asn Gln Asp Pro Glu
485 490 495

Ile Lys Asp His Val Asn Ser Leu Gly Glu Asn Leu Lys Thr Leu Arg
500 505 510

Leu Arg Leu Arg Arg Cys His Arg Phe Leu Pro Cys Glu Asn Lys Ser
515 520 525

Lys Ala Val Glu Gln Ile Lys Asn Ala Phe Asn Lys Leu Gln Glu Lys
530 535 540

Gly Ile Tyr Lys Ala Met Ser Glu Phe Asp Ile Phe Ile Asn Tyr Ile
545 550 555 560

Glu Ala Tyr Met Thr Ile Lys Ala Arg
565

<210> SEQ ID NO 53
<211> LENGTH: 563
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ile Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg Gly Gly Gly Gly Ser Gly Gly Gly Gly Ser Gly Gly Gly

```
145                 150                 155                 160

Gly Ser Gln Val Gln Leu Gln Gln Trp Gly Ala Gly Leu Leu Lys Pro
                165                 170                 175

Ser Glu Thr Leu Arg Leu Thr Cys Ala Val Tyr Gly Gly Ser Phe Thr
            180                 185                 190

Asn Tyr Gly Val His Trp Ile Arg Gln Pro Pro Gly Lys Gly Leu Glu
        195                 200                 205

Trp Ile Gly Val Ile Trp Ser Gly Gly Asn Thr Asp Tyr Asn Thr Pro
    210                 215                 220

Phe Thr Ser Arg Val Thr Ile Ser Val Asp Thr Ser Lys Asn Gln Phe
225                 230                 235                 240

Ser Leu Gln Leu Asn Ser Val Thr Ala Ala Asp Thr Ala Ile Tyr Tyr
                245                 250                 255

Cys Thr Ser Leu Thr Tyr Tyr Asp Tyr Glu Phe Ala Trp Gly Lys Gly
            260                 265                 270

Thr Thr Val Thr Val Ser Ser Gly Gly Gly Gly Ser Gly Gly Gly Gly
        275                 280                 285

Ser Gly Gly Gly Gly Ser Glu Ile Val Met Thr Gln Ser Pro Gly Thr
    290                 295                 300

Leu Ser Leu Ser Pro Gly Glu Arg Ala Thr Leu Ser Cys Arg Ala Ser
305                 310                 315                 320

Gln Ser Ile Gly Thr Asn Ile His Trp Phe Gln Gln Lys Pro Gly Gln
                325                 330                 335

Ala Pro Arg Leu Leu Ile Tyr Tyr Ala Ser Glu Ser Ile Ser Gly Phe
            340                 345                 350

Pro Asp Arg Phe Ser Gly Ser Gly Ser Gly Thr Asp Phe Thr Leu Thr
        355                 360                 365

Ile Thr Arg Leu Glu Pro Glu Asp Phe Ala Met Tyr Tyr Cys Gln Gln
    370                 375                 380

Asn Asn Asn Trp Pro Thr Thr Phe Gly Gln Gly Thr Lys Leu Glu Ile
385                 390                 395                 400

Lys Gly Gly Gly Gly Ser Gly Gly Gly Gly Ser Gly Gly Gly Gly Ser
                405                 410                 415

Thr Asp Gln Cys Asp Asn Phe Pro Gln Met Leu Arg Asp Leu Arg Asp
            420                 425                 430

Ala Phe Ser Arg Val Lys Thr Phe Phe Gln Thr Lys Asp Glu Leu Asp
        435                 440                 445

Asn Leu Leu Leu Lys Glu Ser Leu Leu Glu Asp Phe Lys Gly Tyr Leu
    450                 455                 460

Gly Cys Gln Ala Leu Ser Glu Met Ile Gln Phe Tyr Leu Glu Glu Val
465                 470                 475                 480

Met Pro Gln Ala Glu Asn Gln Asp Pro Glu Ile Lys Asp His Val Asn
                485                 490                 495

Ser Leu Gly Glu Asn Leu Lys Thr Leu Arg Leu Arg Leu Arg Arg Cys
            500                 505                 510

His Arg Phe Leu Pro Cys Glu Asn Lys Ser Lys Ala Val Glu Gln Ile
        515                 520                 525

Lys Asn Ala Phe Asn Lys Leu Gln Glu Lys Gly Ile Tyr Lys Ala Met
    530                 535                 540

Ser Glu Phe Asp Ile Phe Ile Asn Tyr Ile Glu Ala Tyr Met Thr Ile
545                 550                 555                 560

Lys Ala Arg
```

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Ser Ser Gly Gly Gly Gly Ser Gly Gly Gly Gly Ser Gly Gly Gly Gly Ser
1 5 10 15

<210> SEQ ID NO 55
<211> LENGTH: 147
<212> TYPE: PRT
<213> ORGANISM: Artificial Sequence
<220> FEATURE:
<223> OTHER INFORMATION: DV05 Protein

<400> SEQUENCE: 55

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ala Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg
145

<210> SEQ ID NO 56
<211> LENGTH: 441
<212> TYPE: DNA
<213> ORGANISM: Artificial Sequence
<220> FEATURE:
<223> OTHER INFORMATION: DV05 Nucleic acid
<220> FEATURE:
<221> NAME/KEY: misc_feature
<222> LOCATION: (225)..(225)
<223> OTHER INFORMATION: n is a, c, g, or t

<400> SEQUENCE: 56
accgaccagt gcgacaactt ccctcagatg ctgcgggacc tgagagatgc cttctccaga 60
gtgaaaacat tcttccagac caaggacgag ctggacaacc tgctgctgaa agagtccctg 120
ctggaagatt tcaagggcta cctgggctgt caggccctgt ccgagatgat ccagttctac 180
ctggaagaag tgatgcccca ggccgagaat caggaccccg aggcnaagga ccacgtgaac 240
tccctgggcg agaacctgaa aaccctgcgg ctgagactgc ggcggtgcca cagatttctg 300
ccctgcgaga acaagtccaa ggccgtggaa cagatcaaga acgccttcaa caagctgcaa 360
gagaagggca tctacaaggc catgagcgag ttcgacatct tcatcaacta catcgaggcc 420
tacatgacca tcaaggccag a 441

<210> SEQ ID NO 57
<211> LENGTH: 147
<212> TYPE: PRT
<213> ORGANISM: Artificial Sequence
<220> FEATURE:
<223> OTHER INFORMATION: DV06 Protein

<400> SEQUENCE: 57

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Val Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ile Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg
145

<210> SEQ ID NO 58
<211> LENGTH: 441
<212> TYPE: DNA
<213> ORGANISM: Artificial Sequence
<220> FEATURE:
<223> OTHER INFORMATION: DV06 Nucleic acid
<220> FEATURE:
<221> NAME/KEY: misc_feature
<222> LOCATION: (93)..(93)
<223> OTHER INFORMATION: n is a, c, g, or t

<400> SEQUENCE: 58
accgaccagt gcgacaactt ccctcagatg ctgcgggacc tgagagatgc cttctccaga 60
gtgaaaacat tcttccagac caaggacgag gtngacaacc tgctgctgaa agagtccctg 120
ctggaagatt tcaagggcta cctgggctgt caggccctgt ccgagatgat ccagttctac 180
ctggaagaag tgatgcccca ggccgagaat caggaccccg agatcaagga ccacgtgaac 240
tccctgggcg agaacctgaa aaccctgcgg ctgagactgc ggcggtgcca cagatttctg 300
ccctgcgaga acaagtccaa ggccgtggaa cagatcaaga acgccttcaa caagctgcaa 360
gagaagggca tctacaaggc catgagcgag ttcgacatct tcatcaacta catcgaggcc 420
tacatgacca tcaaggccag a 441

<210> SEQ ID NO 59
<211> LENGTH: 147
<212> TYPE: PRT

<213> ORGANISM: Artificial Sequence
<220> FEATURE:
<223> OTHER INFORMATION: DV07 Protein

<400> SEQUENCE: 59

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg
145
```

<210> SEQ ID NO 60
<211> LENGTH: 441
<212> TYPE: DNA
<213> ORGANISM: Artificial Sequence
<220> FEATURE:
<223> OTHER INFORMATION: DV07 Nucleic acid

<400> SEQUENCE: 60

```
accgaccagt gcgacaactt ccctcagatg ctgcgggacc tgagagatgc cttctccaga     60

gtgaaaacat tcttccagac caaggacgag ctggacaacc tgctgctgaa agagtccctg    120

ctggaagatt tcaagggcta cctgggctgt caggccctgt ccgagatgat ccagttctac    180

ctggaagaag tgatgcccca ggccgagaat caggaccccg agatcaagga ccacgtgaac    240

tccctgggcg agaacctgaa aaccctgcgg ctgagactgc ggcggtgcca cagatttctg    300

ccctgcgaga acaagtccaa ggccgtggaa cagatcaaga acgccttcaa caagctgcaa    360

gagaagggca tctacaaggc catgagcgag ttcgacatct tcatcaacta catcgaggcc    420

tacatgacca tcaaggccag a                                              441
```

<210> SEQ ID NO 61
<211> LENGTH: 565
<212> TYPE: PRT
<213> ORGANISM: Artificial Sequence
<220> FEATURE:
<223> OTHER INFORMATION: DEboDV07 Variant 1

<400> SEQUENCE: 61

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
```

-continued

```
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Ser Gly Phe Ser Leu Thr
            180                 185                 190

Asn Tyr Gly Val Asn Trp Ile Arg Gln Pro Pro Gly Lys Gly Leu Glu
        195                 200                 205

Trp Ile Gly Val Ile Trp Ser Gly Gly Asn Thr Asp Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
            260                 265                 270

Lys Gly Thr Thr Val Thr Val Ser Ser Gly Gly Gly Gly Ser Gly Gly
        275                 280                 285

Gly Gly Ser Gly Gly Gly Gly Ser Glu Ile Val Met Thr Gln Ser Pro
    290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile Gly Trp Phe Gln Gln Lys Pro
                325                 330                 335

Gly Gln Ala Pro Arg Leu Leu Ile Lys Tyr Ala Ser Glu Arg Ala Ala
            340                 345                 350

Gly Phe Pro Asp Arg Phe Ser Gly Ser Gly Ser Gly Thr Asp Phe Thr
        355                 360                 365

Leu Thr Ile Thr Arg Leu Glu Pro Glu Asp Phe Ala Met Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
        435                 440                 445

Leu Asp Asn Leu Leu Leu Lys Glu Ser Leu Leu Glu Asp Phe Lys Gly
    450                 455                 460
```

```
Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
                565


<210> SEQ ID NO 62
<211> LENGTH: 1698
<212> TYPE: DNA
<213> ORGANISM: Artificial Sequence
<220> FEATURE:
<223> OTHER INFORMATION: DEboDV07 Variant 1 Nucleic acid

<400> SEQUENCE: 62

accgaccagt gcgacaactt ccctcagatg ctgcgggacc tgagagatgc cttctccaga      60

gtgaaaacat tcttccagac caaggacgag ctggacaacc tgctgctgaa agagtccctg     120

ctggaagatt tcaagggcta cctgggctgt caggccctgt ccgagatgat ccagttctac     180

ctggaagaag tgatgcccca ggccgagaat caggaccccg agatcaagga ccacgtgaac     240

tccctgggcg agaacctgaa aaccctgcgg ctgagactgc ggcggtgcca cagatttctg     300

ccctgcgaga acaagtccaa ggccgtggaa cagatcaaga acgccttcaa caagctgcaa     360

gagaagggca tctacaaggc catgagcgag ttcgacatct tcatcaacta catcgaggcc     420

tacatgacca tcaaggccag aggcggcgga ggatctggcg gaggtggaag cggaggcggt     480

ggatctcagg ttcagttgca gcaatggggc gctggcctgc tgaagccttc tgagacactg     540

tctctgacct gcgccgtgtc cggcttctct ctgaccaatt acggcgtgaa ctggattcgg     600

cagcctcctg gcaaaggcct ggaatggatc ggagtgattt ggagcggcgg caacaccgac     660

tacaacccca gtctgaaggg cagagtggcc atctccgtgg acacctccaa gaaccagttc     720

tccctgagac tgaactccgt gaccgccgct gataccgcca tctactactg tgctagagcc     780

ctgacctact acgactacga gttcgcctat tggggcaagg gcaccaccgt gactgttagt     840

agtggtggtg gcggtagtgg cggaggcggc tcaggcggtg gtggatctga aatcgtgatg     900

acccagtctc ctggcactct gtctctgtct cccggcgaga gagctaccct gtcttgtaga     960

gcctctcagt ccatcggcac caacatcggc tggttccagc agaagcctgg acaggctccc    1020

cggctgctga ttaagtacgc ctctgagaga gccgctggct tccctgacag attctccggc    1080

tctggctctg gcaccgactt caccctgacc atcaccagac tggaacccga ggacttcgct    1140

atgtactact gccagcagaa caacaactgg cccaccacct ttggccaggg caccaagctg    1200

gaaatcaaag gtggcggtgg ttcaggtggc ggaggaagcg gcggaggcgg atctacagat    1260

cagtgtgaca attttcccca aatgctgagg gatctgcggg acgccttcag ccgggtcaag    1320

acattttttc agacaaagga tgaactcgat aacctcttgc tcaaagagag cctgctcgag    1380

gactttaagg gatatctggg atgccaggct ctgagcgaaa tgattcagtt ttatctcgag    1440
```

gaagtcatgc ctcaagcaga gaaccaggat ccagagatta aggatcatgt gaatagcctc 1500
ggggagaacc tcaagacact gagactccgg ctgagaagat gccaccggtt tctgccttgt 1560
gaaaacaaaa gcaaggctgt cgagcagatt aagaatgctt ttaacaaact ccaagaaaaa 1620
gggatctata aggctatgtc tgagtttgat atctttatca attatatcga agcttatatg 1680
actattaagg cccggtag 1698

<210> SEQ ID NO 63
<211> LENGTH: 565
<212> TYPE: PRT
<213> ORGANISM: Artificial Sequence
<220> FEATURE:
<223> OTHER INFORMATION: DEboDV07 Variant 2

<400> SEQUENCE: 63

Thr Asp Gln Cys Asp Asn Phe Pro Gln Met Leu Arg Asp Leu Arg Asp
1 5 10 15

Ala Phe Ser Arg Val Lys Thr Phe Phe Gln Thr Lys Asp Glu Leu Asp
20 25 30

Asn Leu Leu Leu Lys Glu Ser Leu Leu Glu Asp Phe Lys Gly Tyr Leu
35 40 45

Gly Cys Gln Ala Leu Ser Glu Met Ile Gln Phe Tyr Leu Glu Glu Val
50 55 60

Met Pro Gln Ala Glu Asn Gln Asp Pro Glu Ile Lys Asp His Val Asn
65 70 75 80

Ser Leu Gly Glu Asn Leu Lys Thr Leu Arg Leu Arg Leu Arg Arg Cys
85 90 95

His Arg Phe Leu Pro Cys Glu Asn Lys Ser Lys Ala Val Glu Gln Ile
100 105 110

Lys Asn Ala Phe Asn Lys Leu Gln Glu Lys Gly Ile Tyr Lys Ala Met
115 120 125

Ser Glu Phe Asp Ile Phe Ile Asn Tyr Ile Glu Ala Tyr Met Thr Ile
130 135 140

Lys Ala Arg Gly Gly Gly Gly Ser Gly Gly Gly Gly Ser Gly Gly Gly
145 150 155 160

Gly Ser Gln Val Gln Leu Gln Gln Trp Gly Ala Gly Leu Leu Lys Pro
165 170 175

Ser Glu Thr Leu Ser Leu Thr Cys Ala Val Tyr Gly Phe Ser Leu Thr
180 185 190

Asn Tyr Gly Val His Trp Ile Arg Gln Pro Pro Gly Lys Gly Leu Glu
195 200 205

Trp Ile Gly Val Ile Trp Ser Gly Gly Asn Thr Asp Tyr Asn Thr Pro
210 215 220

Phe Thr Ser Arg Val Ala Ile Ser Val Asp Thr Ser Lys Asn Gln Phe
225 230 235 240

Ser Leu Arg Leu Asn Ser Val Thr Ala Ala Asp Thr Ala Ile Tyr Tyr
245 250 255

Cys Thr Ser Ala Leu Thr Tyr Tyr Asp Tyr Glu Phe Ala Tyr Trp Gly
260 265 270

Lys Gly Thr Thr Val Thr Val Ser Ser Gly Gly Gly Gly Ser Gly Gly
275 280 285

Gly Gly Ser Gly Gly Gly Gly Ser Glu Ile Val Met Thr Gln Ser Pro
290 295 300

Gly Thr Leu Ser Leu Ser Pro Gly Glu Arg Ala Thr Leu Ser Cys Arg

```
305                 310                 315                 320

Ala Ser Gln Ser Ile Gly Thr Asn Ile His Trp Phe Gln Gln Lys Pro
                325                 330                 335

Gly Gln Ala Pro Arg Leu Leu Ile Tyr Tyr Ala Ser Glu Ser Ile Ser
            340                 345                 350

Gly Phe Pro Asp Arg Phe Ser Gly Ser Gly Ser Gly Thr Asp Phe Thr
        355                 360                 365

Leu Thr Ile Thr Arg Leu Glu Pro Glu Asp Phe Ala Met Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
        435                 440                 445

Leu Asp Asn Leu Leu Leu Lys Glu Ser Leu Leu Glu Asp Phe Lys Gly
    450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
                565
```

<210> SEQ ID NO 64
<211> LENGTH: 1770
<212> TYPE: DNA
<213> ORGANISM: Artificial Sequence
<220> FEATURE:
<223> OTHER INFORMATION: DEboDV07 Variant 2 Nucleic acid

<400> SEQUENCE: 64

```
gctagcgccg ccaccatggg atggtctttg atcctgctgt tcctggtggc cgtggctacc     60

agagtgcatt ctaccgacca gtgcgacaac ttccctcaga tgctgcggga cctgagagat    120

gccttctcca gagtgaaaac attcttccag accaaggacg agctggacaa cctgctgctg    180

aaagagtccc tgctggaaga tttcaagggc tacctgggct gtcaggccct gtccgagatg    240

atccagttct acctggaaga agtgatgccc caggccgaga atcaggaccc cgagatcaag    300

gaccacgtga actccctggg cgagaacctg aaaaccctgc ggctgagact gcggcggtgc    360

cacagatttc tgccctgcga gaacaagtcc aaggccgtgg aacagatcaa gaacgccttc    420

aacaagctgc aagagaaggg catctacaag gccatgagcg agttcgacat cttcatcaac    480

tacatcgagg cctacatgac catcaaggcc agaggcggcg gaggatctgg cggaggtgga    540

agcggaggcg gtggatctca ggttcagttg cagcaatggg gcgctggcct gctgaagcct    600
```

```
tctgagacac tgtctctgac ctgcgccgtg tacggcttct ccctgaccaa ttatggcgtg    660

cactggatca gacagcctcc aggcaaaggc ctggaatgga tcggagtgat ttggagcggc    720

ggcaacaccg actacaacac cccttttcacc tctagagtgg ccatctccgt ggacacctcc   780

aagaaccagt tcagcctgag actgaactcc gtgaccgccg ctgataccgc catctactac    840

tgcacctccg ctctgaccta ctacgactac gagttcgcct actggggcaa gggcaccaca    900

gtgactgtta gtagtggtgg cggaggtagc ggtggtggtg gtagtggcgg tggcggatct    960

gagatcgtga tgacccaatc tcctggcact ctgtctctgt ctcccggcga gagagctacc   1020

ctgtcttgta gagcctctca gtccatcggc accaacatcc actggttcca gcagaagcct   1080

ggacaggccc ctagactgct gatctactac gcctccgaga gcatcagcgg cttccctgac   1140

agattctccg gctctggctc tggcaccgac ttcaccctga caatcacccg gctggaacct   1200

gaggacttcg ctatgtacta ctgccagcag aacaacaact ggcccaccac ctttggccag   1260

ggcaccaagc tggaaatcaa aggcggaggc ggcagtggcg gcggtggctc cggcggaggc   1320

ggatctacag atcagtgtga caattttccc caaatgctga gggatctgcg ggacgccttc   1380

agccgggtca agacattttt tcagacaaag gatgaactcg ataacctctt gctcaaagag   1440

agcctgctcg aggacttcaa aggatatctg ggatgccagg ctctgagcga aatgattcag   1500

ttttatctcg aggaagtcat gccacaagca gagaaccagg atccagagat taaggatcat   1560

gtgaatagcc tcggggagaa cctcaagaca ctgagactcc ggctgagaag atgccaccgg   1620

tttctgcctt gtgaaaacaa aagcaaggct gtcgagcaga ttaagaatgc ttttaacaaa   1680

ctccaagaaa aagggatcta taaggctatg tctgagtttg atatctttat caattatatc   1740

gaagcttata tgactattaa ggcccggtag                                    1770
```

<210> SEQ ID NO 65
<211> LENGTH: 565
<212> TYPE: PRT
<213> ORGANISM: Artificial Sequence
<220> FEATURE:
<223> OTHER INFORMATION: DEboDV07 Variant 3

<400> SEQUENCE: 65

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
```

-continued

```
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Phe Ser Leu Thr
            180                 185                 190

Asn Tyr Gly Val His Trp Ile Arg Gln Pro Pro Gly Lys Gly Leu Glu
        195                 200                 205

Trp Leu Gly Val Ile Trp Ser Gly Gly Asn Thr Asp Tyr Asn Thr Pro
    210                 215                 220

Phe Thr Ser Arg Val Ala Ile Ser Lys Asp Asn Ser Lys Asn Gln Val
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
            260                 265                 270

Lys Gly Thr Thr Val Thr Val Ser Ser Gly Gly Gly Gly Ser Gly Gly
        275                 280                 285

Gly Gly Ser Gly Gly Gly Gly Ser Glu Ile Val Leu Thr Gln Ser Pro
    290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile His Trp Tyr Gln Gln Lys Pro
                325                 330                 335

Gly Gln Ala Pro Arg Leu Leu Ile Lys Tyr Ala Ser Glu Ser Ile Ser
            340                 345                 350

Gly Phe Pro Asp Arg Phe Ser Gly Ser Gly Ser Gly Thr Asp Phe Thr
        355                 360                 365

Leu Thr Ile Thr Arg Leu Glu Pro Glu Asp Phe Ala Met Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
        435                 440                 445

Leu Asp Asn Leu Leu Leu Lys Glu Ser Leu Leu Glu Asp Phe Lys Gly
    450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
                565
```

<210> SEQ ID NO 66
<211> LENGTH: 1698
<212> TYPE: DNA
<213> ORGANISM: Artificial Sequence
<220> FEATURE:
<223> OTHER INFORMATION: DEboDV07 Variant 3 Nucleic acid

<400> SEQUENCE: 66
accgaccagt gcgacaactt ccctcagatg ctgcgggacc tgagagatgc cttctccaga 60
gtgaaaacat tcttccagac caaggacgag ctggacaacc tgctgctgaa agagtccctg 120
ctggaagatt tcaagggcta cctgggctgt caggccctgt ccgagatgat ccagttctac 180
ctggaagaag tgatgcccca ggccgagaat caggaccccg agatcaagga ccacgtgaac 240
tccctgggcg agaacctgaa aaccctgcgg ctgagactgc ggcggtgcca cagatttctg 300
ccctgcgaga acaagtccaa ggccgtggaa cagatcaaga acgccttcaa caagctgcaa 360
gagaagggca tctacaaggc catgagcgag ttcgacatct tcatcaacta catcgaggcc 420
tacatgacca tcaaggccag aggcggcgga ggatctggcg gaggtggaag cggaggcggt 480
ggatctcagg ttcagttgca gcaatggggc gctggcctgc tgaagccttc tgagacactg 540
tctctgacct gcgccgtgta cggcttctcc ctgaccaatt atggcgtgca ctggatcaga 600
cagcctccag gcaaaggcct ggaatggctg ggagtgattt ggagcggcgg caacaccgac 660
tacaacaccc ctttcacctc tagagtggcc atctccaagg acaactccaa gaaccaggtg 720
tccctgagac tgaactccgt gaccgctgcc gataccgcca tctactactg tgctagagcc 780
ctgacctact acgactacga gttcgcctat tggggcaagg gcaccaccgt gactgttagt 840
agtggtggtg gcggtagtgg cggaggcggc tcaggcggtg gtggatctga aattgtgctg 900
acccagtctc ctggcactct gtctttgagc cctggcgaga gagctaccct gtcctgtaga 960
gcctctcagt ccatcggcac caacatccac tggtatcagc agaagcctgg acaggcccct 1020
cggctgctga ttaagtacgc ctccgagtcc atcagcggct tccctgacag attctccggc 1080
tctggctctg gcaccgactt caccctgaca atcacccggc tggaacctga ggacttcgct 1140
atgtactact gccagcagaa caacaactgg cccaccacct ttggccaggg caccaagctg 1200
gaaatcaaag gtggcggtgg ttcaggtggc ggaggaagcg gcggaggcgg atctacagat 1260
cagtgtgaca attttcccca aatgctgagg gatctgcggg acgccttcag ccgggtcaag 1320 acatttttc agacaaagga tgaactcgat aacctcttgc tcaaagagag cctgctcgag 1380
gacttcaaag gatatctggg atgccaggct ctgagcgaaa tgattcagtt ttatctcgag 1440
gaagtcatgc ctcaagcaga gaaccaggat ccagagatta aggatcatgt gaatagcctc 1500
ggggagaacc tcaagacact gagactccgg ctgagaagat gccaccggtt tctgccttgt 1560
gaaaacaaaa gcaaggctgt cgagcagatt aagaatgctt ttaacaaatt gcaagaaaaa 1620
gggatctata aggctatgtc tgagtttgat atctttatca attatatcga agcttatatg 1680
actattaagg cccggtag 1698

<210> SEQ ID NO 67
<211> LENGTH: 565
<212> TYPE: PRT
<213> ORGANISM: Artificial Sequence
<220> FEATURE:
<223> OTHER INFORMATION: DEboDV07 Variant 4

<400> SEQUENCE: 67

-continued

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Thr Val Ser Gly Phe Ser Leu Thr
            180                 185                 190

Asn Tyr Gly Val His Trp Val Arg Gln Pro Pro Gly Lys Gly Leu Glu
        195                 200                 205

Trp Leu Gly Val Ile Trp Ser Gly Gly Asn Thr Asp Tyr Asn Thr Pro
    210                 215                 220

Phe Thr Ser Arg Val Ala Ile Ser Lys Asp Asn Ser Lys Asn Gln Val
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
            260                 265                 270

Lys Gly Thr Thr Val Thr Val Ser Ser Gly Gly Gly Gly Ser Gly Gly
        275                 280                 285

Gly Gly Ser Gly Gly Gly Gly Ser Glu Ile Val Leu Thr Gln Ser Pro
    290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile His Trp Tyr Gln Gln Lys Pro
                325                 330                 335

Gly Gln Ala Pro Arg Leu Leu Ile Lys Tyr Ala Ser Glu Ser Ile Ser
            340                 345                 350

Gly Ile Pro Asp Arg Phe Ser Gly Ser Gly Ser Gly Thr Asp Phe Thr
        355                 360                 365

Leu Thr Ile Thr Arg Leu Glu Pro Glu Asp Phe Ala Asp Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
```

```
            420                 425                 430

Arg Asp Ala Phe Ser Arg Val Lys Thr Phe Phe Gln Thr Lys Asp Glu
        435                 440                 445

Leu Asp Asn Leu Leu Leu Lys Glu Ser Leu Leu Glu Asp Phe Lys Gly
    450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
                565


<210> SEQ ID NO 68
<211> LENGTH: 1695
<212> TYPE: DNA
<213> ORGANISM: Artificial Sequence
<220> FEATURE:
<223> OTHER INFORMATION: DEboDV07 Variant 4 Nucleic acid

<400> SEQUENCE: 68

accgaccagt gcgacaactt ccctcagatg ctgcgggacc tgagagatgc cttctccaga     60

gtgaaaacat tcttccagac caaggacgag ctggacaacc tgctgctgaa agagtccctg    120

ctggaagatt tcaagggcta cctgggctgt caggccctgt ccgagatgat ccagttctac    180

ctggaagaag tgatgcccca ggccgagaat caggaccccg agatcaagga ccacgtgaac    240

tccctgggcg agaacctgaa aaccctgcgg ctgagactgc ggcggtgcca cagatttctg    300

ccctgcgaga acaagtccaa ggccgtggaa cagatcaaga acgccttcaa caagctgcaa    360

gagaagggca tctacaaggc catgagcgag ttcgacatct tcatcaacta catcgaggcc    420

tacatgacca tcaaggccag aggcggcgga ggatctggcg gaggtggaag cggaggcggt    480

ggatctcagg ttcagttgca gcaatggggc gctggcctgc tgaagccttc tgagacactg    540

tctctgacct gcaccgtgtc cggcttctcc ctgaccaatt atggcgtgca ctgggtccga    600

cagcctccag gcaaaggatt ggaatggctg ggagtgattt ggagcggcgg caacaccgac    660

tacaacaccc ctttcacctc tagagtggcc atctccaagg acaactccaa gaaccaggtg    720

tccctgagac tgaactccgt gaccgctgcc gataccgcca tctactactg tgctagagcc    780

ctgacctact acgactacga gttcgcctat tggggcaagg gcaccaccgt gactgttagt    840

agtggtggtg gcggtagtgg cggaggcggc tcaggcggtg gtggatctga aattgtgctg    900

acccagtctc ctggcactct gtctttgagc cctggcgaga gagctaccct gtcctgtaga    960

gcctctcagt ccatcggcac caacatccac tggtatcagc agaagcctgg acaggcccct   1020

cggctgctga ttaagtacgc ctccgagtcc atcagcggca tccctgacag attctccggc   1080

tctggctctg gcaccgactt caccctgaca atcacccggc tggaacctga ggacttcgcc   1140

gactactact gccagcagaa caacaactgg cccaccacct ttggccaggg caccaagctg   1200
```

-continued

```
gaaatcaaag gtggcggtgg ttcaggtggc ggaggaagcg gcggaggcgg atctacagat   1260
cagtgtgaca attttcccca aatgctgagg gatctgcggg acgccttcag ccgggtcaag   1320
acattttttc agacaaagga tgaactcgat aacctcttgc tcaaagagag cctgctcgag   1380
gacttcaaag gatatctggg atgccaggct ctgagcgaaa tgattcagtt ttatctcgag   1440
gaagtcatgc ctcaagcaga gaaccaggat ccagagatta aggatcatgt gaatagcctc   1500
ggggagaacc tcaagacact gagactccgg ctgagaagat gccaccggtt tctgccttgt   1560
gaaaacaaaa gcaaggctgt cgagcagatt aagaatgctt ttaacaaatt gcaagaaaaa   1620
gggatctata aggctatgtc tgagtttgat atctttatca attatatcga agcttatatg   1680
actattaagg cccgg                                                    1695
```